US007655787B2

(12) United States Patent
Guo et al.

(10) Patent No.: US 7,655,787 B2
(45) Date of Patent: Feb. 2, 2010

(54) PRNA CHIMERA

(75) Inventors: Peixuan Guo, West Lafayette, IN (US); Stephen M. Hoeprich, North Canton, OH (US); Dan Shu, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 261 days.

(21) Appl. No.: 10/373,612

(22) Filed: Feb. 24, 2003

(65) Prior Publication Data

US 2004/0126771 A1 Jul. 1, 2004

Related U.S. Application Data

(63) Continuation-in-part of application No. PCT/US01/26333, filed on Aug. 23, 2001.

(60) Provisional application No. 60/433,697, filed on Dec. 16, 2002, provisional application No. 60/227,393, filed on Aug. 23, 2000.

(51) Int. Cl.
*C07H 21/04* (2006.01)

(52) U.S. Cl. .................. 536/24.5; 536/24.31; 536/24.1; 435/325; 435/375; 514/44

(58) Field of Classification Search ........................ None
See application file for complete search history.

(56) References Cited

U.S. PATENT DOCUMENTS

| 5,998,148 A * | 12/1999 | Bennett et al. .................. 435/6 |
| 6,448,083 B1 | 9/2002 | Larocca et al. |
| 6,808,926 B1 * | 10/2004 | Wu et al. ..................... 435/468 |
| 2001/0049111 A1 | 12/2001 | Windhab et al. |
| 2002/0150917 A1 | 10/2002 | Weidenhammer et al. |
| 2004/0157304 A1 | 8/2004 | Guo |
| 2005/0266416 A1 | 12/2005 | Guo |

FOREIGN PATENT DOCUMENTS

| WO | WO 93/24133 | 12/1993 |
| WO | WO 99/51755 | 10/1999 |
| WO | WO 99/51755 A3 | 10/1999 |
| WO | WO 02/16596 A2 | 2/2002 |
| WO | WO 02/16596 A3 | 2/2002 |
| WO | WO 2005/003293 A2 | 1/2005 |
| WO | WO 2005/003293 A3 | 1/2005 |
| WO | WO 2005/035760 A2 | 4/2005 |
| WO | WO 2005/035760 A3 | 4/2005 |
| WO | WO 2007/016507 A2 | 2/2007 |
| WO | WO 2007/016507 A3 | 2/2007 |

OTHER PUBLICATIONS

Nebel, M.E. Identifying Good Predictions of RNA Secondary Structure. Pacific Symposium on Biocomputing 9: 423-434 (2004).*

Zhang et al. Circularly Permuted Viral pRNA Active and Specific in the Packaging of Bateriophage phi29 DNA. Virology 1995, vol. 207:442-451. Academic Press Inc.*

Bailey et al., "Phylogenetic analysis and secondary structure of the *Bacillus subtilis* bacteriophage RNA required for DNA packaging," *J. Biol. Chem.*, 1990; 265:22365-70.

Betrand et al., "The expression cassette determines the functional activity of ribozymes in mammalian cells by controlling their intracellular localization," *RNA*, 1997; 3:75-88.

Bramlage et al.,"HIV-1 as a target for synthetic ribozyne-mediated inhibition of gene expression: site selection and inhibition in cell culture," *Nucleic Acids Res.*, 2000; 28(21):4059-4067.

Cech et al., "Selecting apt RNAs for NMR," *RNA*, 1996; 2, 625-627.

Chen et al., "Magnesium-induced conformational change of packaging RNA for procapsid recognition and binding during phage phi29 DNA encapsidation," *J. Virol.*, 1997; 71:495-500.

Chen et al., "Sequential Action of Six Virus-Encloded DNA-Packaging RNAs during Phage φ29 Genomic DNA Translocation," *J. Virol.*, 1997; 71(5):3864-3871.

Chen et al., "Sequence requirement for hand-in-hand interaction in formation of pRNA dimers and hexamers to gear phi29 DNA translocation motor," *RNA*, 1999; 5:805-18.

Chen et al., "A dimer as a building block in assembly RNA: A hexamer that gears bacterial virus phi29 DNA-translocating machinery," *J. Biol. Chem.*, 2000; 275(23):17510-16.

Coburn et al., "Potent and Specific Inhibition of Human Immunodeficiency Virus Type 1 Replication by RNA Interference," *J. Virol.*, 2002; 76(18):9225-9231.

Cotten et al., "High-efficiency receptor-mediated delivery of small and large (48 kilobase gene constructs using the endosome-disruption activity of defective or chemically inactivated adenovirus particles," *Proc. Natl. Acad. Sci. U.S.A.*, 1992; 89:6094-6098.

Curiel et al., "Adenovirus enhancement of transferrin-polylysine-mediated gene delivery," *Proc. Natl. Acad. Sci. U.S.A.*, 1991; 88:8850-8854.

Dieckmann et al., "Solution structure of an ATP-binding RNA aptamer reveals a novel fold," *RNA*, 1996; 2, 628-640.

Garver et al., "Mapping the Inter-RNA Interaction of Bacterial Virus Phi29 Packaging RNA by Site-specific Photoaffinity Cross-linking," *J. Biol. Chem.*, 2000; 275(4):2817-24.

Garver et al., "Boundary of pRNA functional domains and minimum pRNA sequence requirement for specific connector binding and DNA packaging of phage phi29," *RNA*, 1997; 3:1068-79.

Guo et al., "A defined system for in vitro packaging of DNA-gp3 of the *Bacillus subtilis* bacteriophage φ29," *Proc. Nat'l Acad. Sci. US*, 1986; 83, 3505-3509.

Guo, "Structure and function of phi29 hexameric RNA that drive viral DNA packaging motor: Review," *Prog. in Nucl. Acid Res. & Mole. Biol.*, 2002; 72:415-472.

Hendrix, "Symmetry mismatch and DNA packaging in large bacteriophages," *Proc. Natl. Acad. Sci. USA*, 1978, 75(10):4779-4783.

(Continued)

*Primary Examiner*—Kimberly Chong
(74) *Attorney, Agent, or Firm*—Seed IP Law Group PLLC

(57) ABSTRACT

A circularly permuted chimeric pRNA molecule carrying a stabilized biologically active RNA, such as a ribozyme.

18 Claims, 21 Drawing Sheets

OTHER PUBLICATIONS

Hoeprich et al., "Computer modeling of three-dimensional structure of DNA-packaging RNA (pRNA) monomer, dimer, and hexamer of Phi29 DNA packaging motor," *J. Biol. Chem.*, 2002; 277(23):20794-803.

Hoeprich et al., "Bacterial virus phi29 pRNA as a hammerhead ribozyme escort to destroy hepatitis B virus," *Gene Therapy*, 2003; 10(15):1258-1267.

Hong et al., "Adenovirus type 5 fiber knob binds to MHC class I α2 domain at the surface of human epithelial and B lymphoblastoid cells," *EMBO J.*, 1997; 16(9):2294-2306.

Huang, "Efficient incorporation of CoA, NAD, FAD into RNA by in vitro transcription," *Nucleic Acids Res.*, 2003; 31(3):e8.

Jaeger et al., "Improved predictions of secondary structures for RNA," *Proc. Natl. Acad. Sci. USA*, 1989; 86:7706-7710.

Kashani-Sabet, et al., "Identification of gene function and functional pathways by systemic plasmid-based ribozyme targeting in adult mice," *Proc. Natl. Acad. Sci. USA*, Mar. 19, 2002; 99(6):3878-3883.

Lee et al., "In Vitro Assembly of Infectious of Double-Stranded DNA Phage φ29 from Cloned Gene Products and Synthetic Nucleic Acids," *J. Virol.* 1995;69(8):5018-5023.

Lee et al., "Sequential Interactions of Structural Proteins in Phage φ29 Procapsid Assembly," *J. Virol.* 1995; 69(8):5024-5032.

Mastrobattista et al., "Functional Characterization of an Endosome-disruptive Peptide and Its Application in Cytosolic Delivery of Immunoliposome-entrapped Proteins," *J. Biol.Chem.*, 2002; 277(30):27135-27143.

Mat-Arip et al., "Three-dimensional interaction of phy29 pRNA dimer probed by chemical modification interference, cryo-AFM, and cross-linking," *J. Biol. Chem.*, 2001; 276(31):32575-32584.

McManus et al., "Gene silencing using micro-RNA designed hairpins," *RNA*, 2002; 8:842-850.

Moore et al., "Structural transformations accompanying the assembly of bacteriophage P22 portal protein rings in vitro," *J. Biol. Chem.*, 2001, 276:6779-6788.

Ojwang et al., "Inhibition of human immunodeficiency virus type 1 expression by a hairpin ribozyme," *Proc. Natl Acad. Sci. U.S.A.*, 1992; 89:10802-10806.

Perriman et al., "Effective ribozyme delivery in plant cells," *Proc. Natl. Acad. Sci. USA*, 1995; 92:6175-9.

Plank et al., "The influence of endosome-disruptive peptides on gene transfer using synthetic virus-like gene transfer systems," *J. Biol. Chem.*, 1994; 269:12918-12924.

Reid et al., "Characterization of the prohead-pRNA interaction of bacteriophage phi29," *J. Biol. Chem.*, 1994; 269:5157-62.

Reid et al., "Probing the structure of bacteriophage phi29 prohead RNA with specific mutations," *J. Biol. Chem.*, 1994; 269(28):18656-18661.

Scholthof, "Rapid delivery of foreign genes into plants by direct rub-inoculation with intact plasmid DNA of a tomato bushy stunt virus gene vector," *J. Viro.*, Sep. 1999; 73(9):7823-7829.

Shu et al., "A Viral RNA That Binds ATP and Contains a Motif Similar to an ATP-binding Aptamer from SELEX," *J. Biol. Chem*, 2003; 278(9):7119-7125.

Shu et al., "Construction of phi29 DNA-Packaging RNA Monomers, Dimers, and Trimers with Variable Sizes and Shapes as Potential Parts for Nanodevices," *J. Nanosci and Nanotech (JNN)*, 2003; 4:295-302.

Shu, "Only one pRNA hexamer but multiple copies of the DNA-packaging protein gp16 are needed for the motor to package bacterial virus phi29 genomic DNA," *Virology*, 309(1):108-113 (2003).

Shultzaberger et al., "Using sequence logos and information analysis of Lrp DNA binding sites to investigate discrepancies between natural selection and SELEX," *Nucleic Acids Res.*, 1999; 27(3):882-887.

Sui et al., "A DNA vector-based RNAi technology to suppress gene expression in mammalian cells," *Proc. Natl. Acad. Sci. U.S.A.*, 2002; 99(8):5515-5520.

Tao et al., "Assembly of a Tailed Bacterial Virus and Its Genome Release Studied in Three Dimensions," *Cell*, 1998, 95:431-437.

Trottier et al., "Approaches to determine stoichiometry of viral assembly components," *J. Virol.*, 1997; 71(1):487-94.

Trottier et al., "Complete inhibition of virion assembly in vivo with mutant pRNA essential for phage phi29 RNA packaging," *J. Virol.*, 1996; 70:55-61.

Trottier et al., "Probing the structure of monomers and dimers of the bacterial virus phi29 hexamer RNA complex by chemical modification," *RNA*, 2000; 6(9):1257-66.

Vaish et al., "Recent developments in the hammerhead ribozyme field," *Nucl. Acids Res.*, 1998; 26:5237-42.

Van Rossenberg et al., "Targeted Lysosome Disruptive Elements for Improvement of Parenchymal Liver Cell-specific Gene Delivery," *J. Biol. Chem.*, 2002; 277:45803-45810.

Wada et al., "Peptide ribonucleic acids (PRNA). 2. A novel strategy for active control of DNA recognition through borate ester formation," *J. Am. Chem. Soc.*, 2000; 122(29):6900-6910.

Wikoff et al., "Virus assembly: Imaging a molecular machine," *Current Biology*, 1999, 9(8):R296-R300.

Yu et al., "RNA interference by expression of short-interfering RNAs and hairpin RNAs in mammalian cells," *Proc. Natl. Acad. Sci U.S.A.*, 2002; 99(9):6047-6052.

Zhang et al., "Conformation of the helical structure of the 5'/3' termini of the essential DNA packaging pRNA of phage phi29," *RNA*, 1995; I:1041-1050.

Zhang et al., "In vitro selection of bacteriophage phi29 prohead RNA aptamers for prohead binding," *J. Biol. Chem.*, 1998; 273:2947-53.

Zhang et al., "Use of circular permutation to assess six bulges and four loops of DNA-packaging pRNA of bacteriophage phi29," *RNA*, 1997; 3:315-323.

Pečenková et al. "Molecular Phylogeny of φ9-Like Phages and Their Evolutionary Relatedness to Other Protein-Primed Replicating Phages and Other Phages Hosted by Gram-Positive Bacteria" *J Mol. Evol.* 1999;48:197-208.

Taira et al. "Construction of Several Kinds of Ribozymes: Their Reactivities and Utilities" *Gene Regulation: Biology of Antisense RNA and DNA*, New York, 1992:35-54.

European Supplemental Search Report issued in patent application EP 03816665.8; dated Jun. 12, 2007.

U.S. Appl. No. 10/539,241, filed Jun. 16, 2005, Guo et al.

Guo, P. "Biological and Biochemical Properties of the Small Viral RNA (pRNA) essential for the Packaging of the dsRNA of Phage phi29." 1994 *Seminars in Virology* 5:27-37.

Guo P., "Preface: A Special Issue on Bionanotechnology," 2005 *J. Nanosci. Nanotech.* 5(12): 1964-1982.

Shu D, Moll W, and Guo P. "Construction of an Imitating Nanomotor Driven by Six ATP-binding RNAs of Bacterial Virus Phi29." 2005 *Electrochemical Society 2004 Proceedings—Nanoscale Devices, Materials, and Biological Systems: Fundamental and Applications*. vol. 2004-13:639-652.

Abrahams et al., "Structure at 2.8 A resolution of F1-ATPase from bovine heart mitochondria," *Nature*, 1994; 370:621-628.

Anderson and Grimes, "Chapter 7: The phi29 DNA Packaging Motor: Seeking the Mechanism," in Catalano (Ed.) *Viral Genome Packaging Machines: Genetics, Structure, and Mechanism* Kluwer Academic/Plenum Publishers: New York, NY; Apr. 15, 2005. pp. 1-15.

Chen, C., et al., "New approaches to stoichiometry determination and mechanism investigation on RNA involved in intermediate reactions," 1997 *Nucleic Acid Symp Series*. 36:190-193.

Cotten et al., "Receptor mediated transport of DNA into eukaryotic cells," in Wu (Ed.) *Methods in Enzymology: Recombinant DNA*., vol. 217. Academic Press: San Diego, CA; 1993. Title page, publisher's page, and pp. 618-644.

Davis et al., "Identifying consensus patterns and secondary structure in SELEX sequence sets," in Abelson (Ed.) *Methods in Enzymology: Combinatorial Chemistry*, vol. 267. Academic Press: San Diego, CA; 1996. Title page, publisher's page, and pp. 302-314.

Gold, "The SELEX process: a surprising source of therapeutic and diagnostic compounds," *Harvey Lect.*, 1995; 91:47-57.

Guo S. et al., "Gene cloning, purification, and stoichiometry quantification of phi29 anti-receptor gp12 with potential use as a special ligand for gene delivery," 2003 *Gene* 315:145-152.

Guo, Y. et al., "Construction and 3-D modeling of connector arrays with tetragonal to decagonal transition induced by pRNA of phi29 DNA-packaging motor," 2005*J. Nanosci. and Nanotech.* 5:856-863.

Hoeprich, Stephan Michael. "Bacterial virus phi29 pRNA modeling and its use as a hammerhead ribozyme escort to destroy hepatitis B virus and other targets," Doctoral Dissertation. Purdue University; Adviser: Peixuan Guo. Cover date, Dec. 2004.

Huang, Lisa Peiqun. "Biochemical characterization of phi29 DNA packaging enzyme gp16," Doctoral Dissertation. Purdue University; Adviser: Peixuan Guo. Cover date, May 2003.

Huang et al., "Use of acetone to attain highly active and soluble DNA packaging protein gp16 ph phi29 for ATPase assay," 2003 *Virology* 312(2):449-457.

Lee et al., "Interaction of gp16 with pRNA and DNA for genome packaging by the motor of bacterial virus phi29," 2006 *J. Mol. Bio.* 356:589-599.

Moll et al., "Translocation of nicked but not gapped DNA by the packaging motor of bacteriophage phi29," 2005 *J. Mol. Bio.* 351:100-107.

Shu et al., "Bottom-up assembly of RNA arrays and superstructure as potential parts in nanotechnology," 2004 *Nano. Lett.* 4(9):1717-1723.

Shu et al., "A simple mathematical formula for stoichiometry quantification of viral and nanobiological assemblage using slope log/log plot curves," 2004 *J. Virol. Meth.* 115:19-30.

Shu et al., "Counting of six pRNAs of phi29 DNA-packaging motor with customized single-molecule dual-view system," 2007 *EMBO J.* 26(2):527-537.

Wang et al., "Selection with SELEX Method of Small RNA Molecules Specifically Binding to Starch," *Acta Biochem. Et Biophys. Sinica*, 1998; 30:402-404. English language Abstract only.

Wen et al., "Study of transcription and cleavage in vitro of HDV with HBV-specific hammerhead ribozyme,"*Chinese Journal of Heptology*, Mar. 1999; 7(1):11-2. English language Abstract only.

Zhen et al., "In vitro selection and affinity function of the aptamers to *Bacillus anthracis* spores by SELEX," *Acta Biochem. Et Biophys. Sinica*, 2002; 34:635-642. English language Abstract only.

Aggarwal et al., "Biodegradable Alginate Microspheres as a Delivery System for Naked DNA," *Can. J. Vet. Res*, 1999; 63:148-152.

Bazinet et al., "The DNA translocating vertex of dsDNA bacteriophage," *Ann. Rev. Microbiol.*, 1985;39:109-129.

Becerril et al., "Toward selection of internalizing antibodies from phage libraries," *Biochem. Biophys. Res. Commun.*, 1999; 255:386-393.

Bergelson et al., "Isolation of a common receptor for Coxsackie B viruses and adenoviruses 2 and 5," *Science*, 1997;275(5304):1320-1323.

Bilbao et al., "57: Targeted adenoviral vectors for cancer gene therapy," in Walden (Ed.) *Gene Therapy of Cancer*, 1998; Plenum Press: New York, NY: Title page, publisher's page, and pp. 365-374.

Bjornsti et al., "Morphogenesis of bacteriophage phi 29 of *Bacillus subtilis*: DNA-gp3 intermediate in in vivo and in vitro assembly," *J. Virol.*, Feb. 1982;41:508-517.

Bjornsti et al., "Morphogenesis of bacteriophage phi 29 of *Bacillus subtilits*: prohead restoration for DNA-gp3 packaging and assembly," *J. Virol.*, Mar. 1985;53(3):858-861.

Black, "DNA Packaging in dsDNA bacteriophages," *Ann. Rev. Microbiol.*, 1989;43:267-292.

Boutin, "Purdue researchers connect life's blueprints with it energy source," Feb. 4, 2003; *Purdue News* [online], [retrieved on Mar. 21, 2003]. Retrieved from the Internet:<URL:http://www.news.uns.purdue.edu/html4ever/030204.Guo.ATP.html>; 5 pgs.

Bouvet, "42: Determination of Nucleic Acid Recognition Sequences by SELEX," in Moss (Ed.) *Methods in Molecular Biology: DNA-Protein Interactions; Principles and Protocols 2nd Edition*, 2001; vol. 148; Humana Press: Totowa, NJ. pp. 603-610.

Brummelkamp et al., "A System for Stable Expression of Short Interfering RNAs in Mammalian Cells," *Science*, Apr. 19, 2002; 296:550-553.

Burnell, "Nanotech finds biological inspiration," Oct. 12, 2002; *The Washington Times* [online], [retrieved on Mar. 21, 2003]. Retrieved from the Internet:<URL:http://www.washtimes.com/upi-breaking/20021012-122115-2395r.htm>; 2 pgs.

Carazo et al., "Three-dimensional reconstruction of the connector of bacteriophage phi29 at 1.8 nm resolution," *J. Mol. Biol.*, Dec. 20, 1986; 192(4):853-867.

Carmichael, "Silencing viruses with RNA," *Nature*, Jul. 25, 2002; 418(6896):379-80.

Carrascosa et al., "A precursor of the neck appendage protein of *B. subtilis* phage phi 29," *FEBS Lett.*, 1974; 44(3):317-321.

Chang et al., "The structure of an RNA "kissing" hairpin complex of the HIV TAR hairpin loop and its complement," *J. Mol. Biol.*, May 30, 1997; 269(1):52-66.

Chowrira et al., "Novel guanosine requirement for catalysis by the hairpin ribozyme," *Nature*, Nov. 1991; 354:320-322.

Ciesiolka et al., "Selection of an RNA domain that binds $Zn^{2+}$," *RNA*, 1995; 1:538-50.

Coleman et al., "A novel immune system against bacteriophage infection using complementary RNA (micRNA)," *Nature*, 1985; 315:601-603.

Cotten et al., "Ribozyme mediated destruction of RNA in vivo," *EMBO J.*, 1989; 8(12):3861-3866.

Dennis, "Small RNAs: the genome's guiding hand?" *Nature*, Dec. 19-26, 2002 420(6917):732.

Doering et al., "Rotary DNA motors," *Biophysical Journal*, 1995; 69:2256-2267.

DuraScribe® T7 Transcription Kit/DuraScribe® SP6 Transcription Kit. Product Datasheet. Epicentre Biotechnologies: Madison, WI; Available online [Retrieved Apr. 21, 2006]. Retrieved from the Internet: <http://www.epibio.com/item.asp?id=408>; 4 pgs.

Earnshaw et al., "DNA packaging by the double-stranded DNA bacteriophages," *Cell*, 1980; 21:319-331.

Elbashir et al., "Duplexes of 21-nucleotide RNAs mediate RNA interference in cultured mammalian cells," *Nature*, May 24, 2001; 411(6836):494-498.

Ellington et al., "In vitro selection of RNA molecules that bind specific ligands," *Nature*, 1990; 346:818-22.

Ellington et al., "Selection in vitro of single-stranded DNA molecules that fold into specific ligand-binding structures," *Nature*, 1992; 355:850-2.

Feng et al., "Antiviral activity of a Hammerhead Ribozyme against HBV in HepG2.215 cells," *Sheng Wu Hua Xue Yu Sheng Wu Wu Li Xue Bao (Shanghai)*, 2002; 34(2):204-8. English Language Abstract only.

Feng et al., "Inhibition of hepatitis B virus by hammerhead ribozyme targeted to the poly(A) signal sequence in cultured cells," *Biol. Chem.*, 2001; 382:655-60.

Feng et al., "Inhibition of CCR5-Dependent HIV-1 Infection by Hairpin Ribozyme Gene Therapy against CC-Chemokine Receptor 5," *Virology*, 2000; 276:271-278.

Folini et al., "Inhibition of Telomerase Activity by a Hammerhead Ribozyme Targeting the RNA Component of Telomerase in Human Melanoma Cells," *J. Invest. Dermatol.*, Feb. 2000; 114(2):259-67.

Forster et al., "Self-cleavage of virusoid RNA is performed by the proposed 55-nucleotide active site," *Cell*, Jul. 3, 1987; 50:9-16.

Gao et al., "Tumor-specific expression of anti-*mdr1* ribozyme selectively restores chemosensitivity in multidrug-resistant colon-adenocarcinoma cells," *Int. J. Cancer*, Jul. 30, 1999; 82(3):346-52.

García et al., "Assembly of the Tail Protein of the *Bacillus subtilis* phage phi29," *Virology*, Feb. 1983; 125:18-30.

Gibson et al., "Induction of apoptosis in oral cancer cells by an anti-bcl-2 ribozyme delivered by an adenovirus vecor," *Clinical Cancer Research*, Jan. 2000; 6(1):213-22.

Giordano et al., "Intraviron Targeting of a Functional Anti-Human Immunodeficiency Virus Ribozyme Directed to *pol*," *Virology*, Feb. 2000; 267(2):174-84.

Gitlin et al., "Short interfering RNA confers intracellular antiviral immunity in human cells," *Nature*, Jul. 25, 2002; 418(6896):430-4.

Goila et al., "Sequence specific cleavage of the HIV-1 coreceptor CCR5 gene by a hammer-head ribozyme and a DNA-enzyme: inhibition of the coreceptor function by DNA-enzyme," *FEBS Letters*, 1998; 436:233-238.

Grimes et al., "Bacteriophage phi 29 DNA packaging," *Adv. Virus Res.*, 2002; 58:255-294.

Guasch et al., "Detailed Architecture of a DNA Translocating Machine: The High-resolution Structure of the Bacteriophage phi29 Connector Particle," *Journal of Molecular Biology*, 2002; 315:663-676.

Guo, P. et al., "Characterization of the small RNA of the bacteriophage phi29 DNA packaging machine," *Nucl. Acids Res.*, 1987; 15:7081-90.

Guo, P. et al., "Prohead and DNA-gp3-dependent ATPase activity of the DNA packaging protein gp16 of bacteriophage phi 29," *J. Mol. Biol.*, Sep. 20, 1987; 197(2):229-236.

Guo, P. et al., "A small viral RNA is required for in vitro packaging of bacteriophage phi29 DNA," *Science*, 1987; 236:690-4.

Guo, P. "Introduction: Principles, perspectives, and potential applications in viral assembly," *Seminars in Virology (Editor's Introduction)*, 1994, 5(1):1-3.

Guo, P. et al., "Inter-RNA interaction of phage phi29 RNA to from a hexameric complex for viral DNA transportation," *Mol. Cell.*, 1998; 2:149-55.

Guo, P. et al., "Methods for structural and functional analysis of an RNA hexamer of bacterial virus phi29 DNA packaging motor," *Acta Biochimicaet Biophysica Sinica*, 2002; 34(5):533-543. Available online [retrieved Jul. 3, 2007]. Retrieved from the Internet: <http://www.abbs.info/fulltxt/eng/34050533.htm>; 27 pgs.

Guo, P. et al., "Construction of a viral DNA-packaging nano-motor of phi29." Oral Presentation Abstract. 10$^{th}$ Foresight Conference of Nanotechnology. Bethesda, MD. Oct. 11-13,2002. Abstract available online [retrieved Jul. 2, 2007]. Retrieved from the Internet: <http://www.foresight.org/Conference/MNT10/Abstracts/Guo/index.html>; 2 pgs.

Guo, P. et al., "Viral Motors," Oral Presentation. Nanotechnology 2003: Big things in Little Packages; American Association for the Advancement of Science; Denver, CO. Feb. 13-14, 2003. Meeting Schedule available online [retrieved Jul. 2, 2007]. Retrieved from the Internet: <http://www.aaas.org/meetings/2003/MPE_13.shtml>; 3 pgs.

Guo P., "RNA nanotechnology: engineering, assembly, and applications in detection, gene delivery and therapy," 2005*J. Nanosci. Nanotech.* 5(12): 1964-1982.

Guo, P., "Chapter 13: Bacterial virus phi29 DNA-packaging motor and its potential applications in gene therapy and nanotechnology," in Vo-Dinh (Ed.) Methods in Molecular Biology: Protein Nanotechnology; Humana Press: Totowa, New Jersey. 2005. Title page and pp. 285-324.

Guo, P. et al., "Viral nanomotors for packagingof dsDNA and dsRNA," 2007 *Mol. Microbiol.* 64(4):886-903.

Guo, Peixuan "sRNA of Phage phi29 Essential for DNA Packaging," Grant Abstract, Grant No. 1RO1GM048159-01 [online].National Institute of Health—National Institute of General Medical Sciences, project dates Aug. 1, 1992 to Jul. 31, 1996 [retrieved on Jul. 2, 2007]. Retrieved from the Internet: <URL:http://crisp.cit.nih.gov/crisp/CRISP_LIB.getdoc?textkey=3307636&p_grant_num=1R01GM048159-01&p_query=&ticket=40535116&p_audit_session_id=249250764&p_keywords=>; 2 pgs.

Guo, Peixuan "sRNA of Phage phi29 Essential for DNA Packaging," Grant Abstract, Grant No. 5RO1GM048159-02 [online].National Institute of Health—National Institute of General Medical Sciences, project dates Aug. 1, 1992 to Jul. 31, 1996 [retrieved on Jul. 2, 2007 ]. Retrieved from the Internet: <URL:http://crisp.cit.nih.gov/crisp/CRISP_LIB.getdoc?textkey=3307637&p_grant_num=5R01GM048159-02&p_query=&ticket=40535116&p_audit_session_id=249250764&p_keywords=>; 2 pgs.

Guo, Peixuan "sRNA of Phage phi29 Essential for DNA Packaging," Grant Abstract, Grant No. 5RO1GM048159-03 [online].National Institute of Health—National Institute of General Medical Sciences, project dates Aug. 1, 1992 to Jul. 31, 1996 [retrieved on Jul. 2, 2007]. Retrieved from the Internet: <URL:http://crisp.cit.nih.gov/crisp/CRISP_LIB.getdoc?textkey=2185637&p_grant_num=5R01GM048159-03&p_query=&ticket=40535116&p_audit_session_id=249250764&p_keywords=>; 2 pgs.

Guo, Peixuan "sRNA of Phage phi29 Essential for DNA Packaging," Grant Abstract, Grant No. 5RO1GM048159-04 [online].National Institute of Health—National Institute of General Medical Sciences, project dates Aug. 1, 1992 to Apr. 30, 1997 [retrieved on Jul. 2, 2007]. Retrieved from the Internet: <URL:http://crisp.cit.nih.gov/crisp/CRISP_LIB.getdoc?textkey=2185638&p_grant_num=5R01GM048159-04&p_query=&ticket=40535116&p_audit_session_id=249250764&p_keywords=>; 1 pg.

Guo, Peixuan "Biochemical Study on Phage phi29 pRNA for DNA Packaging," Grant Abstract, Grant No. 2R21GM048159-05A1 [online].National Institute of Health—National Institute of General Medical Sciences, project dates Aug. 1, 1992 to Apr. 30, 1999 [retrieved on Jul. 2, 2007]. Retrieved from the Internet: <URL:http://crisp.cit.nih.gov/crisp/CRISP_LIB.getdoc?textkey=2502527&p_grant_num=2R21GM048159-05A1&p_query=&ticket=40535116&p_audit_session_id=249250764&p_keywords=>; 2 pgs.

Guo, Peixuan "Biochemical Study on Phage phi29 pRNA for DNA Packaging," Grant Abstract, Grant No. 5R21GM048159-06 [online]. National Institute of Health—National Institute of General Medical Sciences, project dates Aug. 1, 1992 to Apr. 30, 2000 [retrieved on Jul. 2, 2007]. Retrieved from the Internet: <URL:http://crisp.cit.nih.gov/crisp/CRISP_LIB.getdoc?textkey=2701575&p_grant_num=5R21GM048159-06&p_query=&ticket=40535116&p_audit_session_id=249250764&p_keywords=>; 2 pgs.

Guo, Peixuan "Stoichiometry Quantification—Complex Biological System," Grant Abstract, Grant No. 1RO1GM060529-01 [online]. National Institute of Health—National Institute of General Medical Sciences, project dates May 1, 2000 to Apr. 30, 2003 [retrieved on Jul. 2, 2007]. Retrieved from the Internet: <URL:http://crisp.cit.nih.gov/crisp/CRISP_LIB.getdoc?textkey=6038263&p_grant_num=1R01GM060529-01&p_query=&ticket=40535116&p_audit_session_id=249250764&p_keywords=>; 2 pgs.

Guo, Peixuan "Stoichiometry Quantification—Complex Biological System," Grant Abstract, Grant No. 5RO1GM060529-02 [online]. National Institute of Health—National Institute of General Medical Sciences, project dates May 1, 2000 to Apr. 30, 2003 [retrieved on Jul. 2, 2007]. Retrieved from the Internet: <URL:http://crisp.cit.nih.gov/crisp/CRISP_LIB.getdoc?textkey=6387064&p_grant_num=5R0IGM060529-02&p_query=&ticket=40535116&p_audit_session_id-249250764&p_keywords=>; 2 pgs.

Guo, Peixuan "Stoichiometry Quantification—Complex Biological System," Grant Abstract, Grant No. 5RO1GM060529-03 [online]. National Institute of Health—National Institute of General Medical Sciences, project dates May 1, 2000 to Apr. 30, 2005 [retrieved on Jul. 2, 2007]. Retrieved from the Internet: <URL:http://crisp.cit.nih.gov/crisp/CRISP_LIB.getdoc?textkey=6520145&p_grant_num=5R01GM060529-03&p_query=&ticket=40535116&p_audit_session _id=249250764&p_keywords=>; 2 pgs.

Guo, Peixuan "Structure/Function of phi29 hexameric pRNA," Grant Abstract, Grant No. IRO1GM059944-01 [online].National Institute of Health—National Institute of General Medical Sciences, project dates Aug. 1, 1999 to Jul. 31, 2003 [retrieved on Jul. 3, 2007]. Retrieved from the Internet: <http://crisp.cit.nih.gov/crisp/CRISP_LIB.getdoc?textkey=2897282&p_grant_num=1R01GM059944-01&p_query=&ticket=40611991&p_audit_session_id= 249382720&p_keywords=> ; 2 pgs.

Guo, Peixuan "Structure/Function of phi29 hexameric pRNA," Grant Abstract, Grant No. 5RO1GM059944-02 [online].National Institute of Health—National Institute of General Medical Sciences, project dates Aug. 1, 1999 to Jul. 31, 2003 [retrieved on Jul. 3, 2007]. Retrieved from the Internet: <http://crisp.cit.nih.gov/crisp/CRISP_LIB.getdoc?textkey=6181986&p_grant_num=5R01GM059944-02&p_query=&ticket=40611991&p_audit_session_id=249382720&p_keywords=>; 2 pgs.

Guo, Peixuan "Structure/Function of phi29 hexameric pRNA," Grant Abstract, Grant No. 5RO1GM059944-03 [online].National Institute of Health—National Institute of General Medical Sciences, project dates Aug. 1, 1999 to Jul. 31, 2003 [retrieved on Jul. 3, 2007]. Retrieved from the Internet: <http://crisp.cit.nih.gov/crisp/CRISP_LIB.getdoc?textkey=6386619&p_grant_num=5R01GM059944-03&p_query=&ticket=40611991&p_audit_session_id=249382720&p_keywords=>; 2 pgs.

Guo, Peixuan "Structure/Function of phi29 hexameric pRNA," Grant Abstract, Grant No. 5RO1GM059944-04 [online].National Institute of Health—National Institute of General Medical Sciences, project dates Aug. 31, 1999 to Aug. 31, 2005 [retrieved on Mar. 20, 2003]. Retrieved from the Internet: <URL:http://www.commons.cit.hih.gov/crisp3/CRISP-LIB.getdoc?textkey=6526211>; 2 pgs.

Guo, Peixuan "Structure/Function of phi29 hexameric pRNA," Grant Abstract, Grant No. 3RO1GM059944-04S1 [online].National Institute of Health—National Institute of General Medical Sciences, project dates Aug. 1, 1999 to Aug. 31, 2005 [retrieved on Jul. 3, 2007]. Retrieved from the Internet: <http://crisp.cit.nih.gov/crisp/CRISP_LIB.getdoc?textkey=6794869&p_grant_num=3R01GM059944-04S1&p_query=& ticket=40611991&p_audit_session_id=249382720& p_keywords=>; 2 pgs.

Guo, Peixuan "Structure/Function of phi29 hexameric pRNA," Grant Abstract, Grant No. 2RO1GM059944-05A2 [online].National Institute of Health—National Institute of General Medical Sciences, project dates Aug. 1, 1999 to Nov. 30, 2009 [retrieved on Jul. 3, 2007]. Retrieved from the Internet: <http://crisp.cit.nih.gov/crisp/CRISP_LIB.getdoc?textkey=6871533&p_grant_num=2R01GM059944-05A2&p_query=&ticket=40611991&p_audit_session_id=249382720&p_keywords=>; 2 pgs.

Guo, Peixuan "Structure/Function of phi29 hexameric pRNA," Grant Abstract, Grant No. 5RO1GM059944-06 [online].National Institute of Health—National Institute of General Medical Sciences, project dates Aug. 1, 1999 to Nov. 30, 2009 [retrieved on Jul. 3, 2007]. Retrieved from the Internet: <http://crisp.cit.nih.gov/crisp/CRISP_LIB.getdoc?textkey=7119621&p_grant_num=5R01GM059944-06&p_query=&ticket=40611991&p_audit_session_id=249382720&p_keywords=>; 1 pg.

Guo, Peixuan "ATP-Induced Conformational Changes of pRNA During Phage 029 DNA Packaging," Grant Abstract, Grant #MCB-9723923 [online]. National Science Foundation, project dates Sep. 1, 1997 to Aug. 31, 2001 [retrieved on Mar. 20, 2003]. Retrieved from the Internet: <URL:http://www.fastlane.nsf.gov/servlet/showaward?award=9723923>; 2 pgs.

Guo, S. et al., "Delivery of siRNA and ribozyme for gene therapy by 35-nm nanoparticles of phi29 motor pRNA," Poster Abstract No. 2641. 206th Meeting of the Electrochemical Society, Inc. 2004 Joint International Meeting: Oct. 3-8, 2004 in Honolulu, HI. Available online [retrieved Jul. 3, 2007]. Retrieved from the Internet: <http://www.electrochem.org/dl/ma/206/pdfs/2641.pdf>; 1pg.

Guo S. et al,. "Specific delivery of therapeutic RNA to cancer cells via the dimerization mechanism of phi29 motor pRNA," 2005 *Human Gene Therapy* 16(9):1097-1109S.

Guo S. et al., "Construction of folate-conjugated pRNA of bacteriophage phi29 DNA packaging motor for delivery of chimeric siRNA to nasopharyngeal carcinoma cells," 2006 *Gene Therapy* 13:814-820.

Ha et al., "Initiation and re-initiation of DNA unwinding by the *Escherichia coli* Rep helicase," *Nature*, 2002; 419:638-641.

Han et al., "Ribozyme-mediated resistance to rice dwarf virus and the transgene silencing in the progeny of transgenic rice plants," *Transgenic Res.*, 2000; 9:195-203.

Hendrix, "Bacteriophage DNA Packaging: RNA Gears in a DNA Transport Machine," *Cell*, 1998; 94:147-50.

Hess et al., "Molecular shuttles based on motor proteins: active transport in synthetic environments," *Reviews in Mol. Biotech.*, 2001; 82:67-85.

Homann et al., "Uptake and Intracellular Transport of RNA Aptamers in African Trypanosomes Suggest Therapeutic "Piggy-Back" Approach," *Bioorganic & Medicinal Chemistry*Oct. 2001; 9:2571-2580.

Horster et al., "Recombinant AAV-2 harboring gfp-antisense/ribozyme fusion sequences monitor transduction, gene expression, and show anti-HIV-1 efficacy," *Gene Ther.*, Jul. 1999; 6(7):1231-8.

Hua et al., "Coupling of kinesin steps to ATP hydrolysis," *Nature*, 1997; 388:390-393.

Hutvágner et al., "A microRNA in a Multiple-Turnover RNAi Enzyme Complex," *Science*, Sep. 20, 2002; 297:2056-2060.

Inoue et al, "Myosin Ixb is a single-headed minus-end-directed processive motor," *Nat. Cell Biol.*, 2002; 4:302-306.

Irie et al., "Therapeutic efficacy of an adenovirus-mediated anti-H-ras ribozyme in experimental bladder cancer," *Antisense Nucleic Acid Drug Dev.*, Aug. 1999; 9(4):341-9.

Jacque et al., "Modulation of HIV-1 replication by RNA interference," *Nature*, Jul. 25, 2002; 418(6896):435-8.

Jackson et al., "Inhibition of HIV-1 Replication by an Anit-tat Hammerhead Ribozyme," *Biochem Biophys Res. Commun.*, 1998; 245:81-84.

Jaeger et al., "Predicting optimal and suboptimal secondary structure for RNA," in Doolittle (Ed.) *Meth. Enzymol. Molecular Evolution: Computer Analysis of Protein and Nucleic Acid Sequences* vol. 183. Academic Press: San Diego, CA; 1990. Title page and pp. 281-306.

Jayasena "Aptamers: An emerging class of molecules that rival antibodies in diagnostics," 1999 *Clin. Chem.* 45(9):1628-1650.

Jiang et al., "Structural basis of RNA folding and recognition in an AMP-RNA aptamer complex," *Nature*, Jul. 11, 1996; 382:183-186.

Jiménez et al., "Computer graphic display method for visualizing three-dimensional biological structures," *Science*, May 30, 1986; 232:1113-1115.

Kaneda et al., "The induction of apoptosis in HeLa cells by the loss of LBP-p40," *Cell Death Differ.*, Jan. 5, 1998; 5(1):20-8.

Khaled et al,. "Controllable self-assembly of nanoparticles for specific delivery of muliple therapeutic molecules to cancer cells using RNA nanotechnology," 2005 *Nano. Lett.* 5:1797-1808.

Kinosita, Jr. et al., "$F_1$-ATPase: A Rotary Motor Made of a Single Molecule," *Cell*, 1998; 93:21-24.

Kitazono et al., "Multidrug Resistance and the Lung Resistance-Related Protein in Human Colon Carcinoma SW-620 Cells," *J. Natl. Cancer Inst.*, Oct. 6, 1999; 91(19):1647-53.

Klebba et al., "Retrovirally expressed anti-HIV ribozymes confer a selective survival advantage on CD4+ T cells in vitro," *Gene Ther.*, Mar. 2000; 7(5):408-416.

Klug et al., "All you wanted to know about SELEX," *Molecular Biology Reports*, 1994; 20:97-107.

Knecht et al., "Antisense RNA inactivation of myosin heavy chain gene expression in Dictyostelium discoideum," *Science*, May 1987; 236:1081-1086.

Kobayashi et al., "Retrovirus-mediated transfer of anti-MDR1 hammerhead ribozymes into multidrug-resistant human leukemia cells: screening for effective target sites," *Int. J. Cancer*, Jun. 11, 1999; 81(6):944-50.

Kraus et al., "Cutting Edge: Novel RNA Ligands Able to Bind CD4 Antigen and Inhibit $CD4^+$ T Lymphocyte Function," *J. Immunol.*, 1998; 160:5209-5212.

Laughrea et al., "Kissing-Loop Model of HIV-1 Genome Dimerization: HIV-1 RNAs Can Assume Alternative Dimeric Forms, and All Sequences Upstream or Downstream of Hairpin 248-271 Are Dispensable for Dimer Formation," *Biochemistry*, 1996; 35(5):1589-1598.

Lee et al., "A Highly Sensitive System for the In Vitro Assembly of Bacteriophage phi29 of *Bacillus subtilis*," *Virology*, 1994; 202:1039-1042.

Lee et al., "Generation and characterization of hammerhead ribozymes targeting rodent metallothionein-I and -II ribonucleic acid," *Toxicology and Applied Pharmacology*, Dec. 15, 1999; 161(3):294-301.

Lee et al., "Functional colocalization of ribozymes and target mRNAs in *Drosophila* oocytes," *FASEB J.*, 2001; 15:2390-2400.

Lewis, "Conference showcases nondevices progress," Nanodot [online], [retrieved on Mar. 21, 2003]. Retrieved from the Internet:<URL:http://nanodot.org/article.pl?sid=02/11/03055252>; 2 pgs.

Li et al., "Induction and Suppression of RNA Silencing by an Animal Virus," *Science*, May 17, 2002; 296:1319-1321.

Lim et al., "Biodegradable, Endosome Disruptive, and Cationic Network-type Polymer as a Highly Efficient and Nontoxic Gene Delivery Carrier," *Bioconjugate Chem.*, 2002; 13(5):952-957.

Liu et al., "Ribozyme-mediated suppression of platelet type 12 lipoxygenase in human erythroleukemia cells," *Cancer Gene Therapy*, May 2000; 7(5):671-5.

Liu et al., "Episomal expression of a hammerhead ribozyme directed against plum pox virus," *Virus Res.*, 2000; 68:15-23.

Liu et al., "Ribozyme ablation demonstrates that the cardiac subtype of the voltage-sensitive calcium channel is the molecular transducer of 1, 25-dihydroxyvitamin D(3)-stimulated calcium influx in osteoblastic cells," *J. Biol. Chem.*, Mar. 24, 2000; 275(12):8711-8718.

Macejak et al., "Adenovirus-Mediated Expression of a Ribozyme to c-*myb* mRNA Inhibits Smooth Muscle Cell Proliferation and Neointima Formation In Vivo," *J. Virol.*, Sep. 1999; 73(9):7745-51.

Mastrangelo et al., "ATP-dependent assembly of double hexamers of SV40 T antigen at the viral origin of DNA replication," *Nature*, 1989; 338:658-662.

Mathews et al., "Expanded sequence dependence of thermodynamic parameters improves prediction of RNA secondary structure," *Journal of Molecular Biology*, May 1999; 288(5):911-940.

McCaffrey et al., "Gene expression: RNA interference in adult mice," *Nature*, Jul. 4, 2002; 418(6893):38-9.

Mercatanti et al., "A method for prediction of accessible sites on an mRNA sequence for target selection of hammerhead ribozymes," *J. Computational Biol.*, 2002; 9:641-653.

Merlo et al., "Ribozymes Targeted to Stearoyl-ACP delta9 Desaturase mRNA Produce Heritable Increases of Stearic Acid in Transgenic Maize Leaves," *Plant Cell*, 1998; 10:1603-21.

Mindich, "Precise Packaging of the Three Genomic Segments of the Double-Stranded-RNA Bacteriophage phi6," *Microbiol. Mol. Biol. Rev.*, 1999; 63:149-160.

Moll et al., "Engineering of bacterial virus phi29 motor pRNA as self-assembling nanomolecular buliding blocks to form conjugates, supramolecular structures and three dimensional arrays," Poster Abstract No. 2617. 206$^{th}$ Meeting of the Electrochemical Society, Inc. 2004 Joint International Meeting: Oct. 3-8, 2004 in Honolulu, HI. Available online [retrieved Jul. 3, 2007]. Retrieved from the Internet: <http://www.electrochem.org/dl/ma/206/pdfs/2617.pdf>; 1 pg.

Murchie et al., "Folding of the Hairpin Ribozyme in Its Natural Conformation Achieves Close Physical Proximity of the Loops," *Mol. Cell*, May 1998; 1:873-881.

Nicklin et al., "Selective Targeting of Gene Transfer to Vascular Endothelial Cells by Use of Peptides Isolated by Phage Display," *Circulation*, 2000; 102:231-237.

Nossal et al., "Bacteriophage T4 proteins replicate plasmids with a preformed R loop at the T4 ori(uvsY) replication origin in vitro," *Mol. Cell*, 2001; 7:31-41.

Ortin et al., "DNA-protein complex in circular DNA from phage phi-29," *Nature New Biol.*, Dec. 29, 1971; 234(52):275-277.

Ozaki et al., "Ribozyme-mediated specific gene replacement of the alpha 1-antitrypsin gene in human hepatoma cells," *J. Hepatol.*, Jul. 1999; 31(1):53-60.

Paddison et al., "Short hairpin RNAs (shRNAs) induce sequence-specific silencing in mammalian cells," *Genes Dev.*, 2002; 16(8):948-958.

Panyam et al., "Rapid endo-lysosomal escape of poly(DL-lactide-*co*-glycolide) nanoparticles: implications for drug and gene delivery," *Faseb J.*, 2002, 16:1217-1226.

Paul et al., "Effective expression of small interfering RNA in human cells," *Nature Biotechnology*, 2002; 20:505-508.

Pečenková et al., "Bacteriophage B103: complete DNA sequence of its genome and relationship to other *Bacillus* phages," *Gene*, 1997; 199:157-63.

Perdue et al., Characterization of Three Species of Nucleocapsids of Equine Herpesvirus Type-1 (EHV-1), *Virology*, 1975; 64:187-204.

Perlman et al., "Adenovirus-encoded hammerhead ribozyme to Bcl-2 inhibits neointimal hyperplasia and induces vascular smooth muscle cell apoptosis," *Cardiovasc. Res.*, 2000; 45(3):570-578.

Pilling et al., "The role of the toxicologic pathologist in the preclinical safety evaluatIon of biotechnology-derived pharmaceuticals," *Toxicologic Pathology*, Nov.-Dec. 1999; 27(6):678-88.

Potter et al., "Construction of Adenovirus for High Level Expression of Small RNAs in Mammalian Cells. *Application to a Bcl-2 ribozyme,*" *Mol. Biotechnol.*, Jun. 2000; 15(2):105-114.

Prevec et al., "A Recombinant Human Adenovirus Vaccine against Rabies," *J. Infect. Dis.*, 1990; 161(1):27-30.

Rayment et al., "Structure of the actin-myosin complex and its implications for muscle contraction," *Science*, 1993; 261:58-65.

"Rna: life's original seed and nanotechnology," *context weblog: sampling new cultural context* [online], [retrieved on Mar. 21, 2003]. Retrieved from the Internet <URL:http://straddle3.net/context/03/en/2003_02_06.html>; 1 pg.

Rock et al., "In Vitro Assays of Processive Myosin Motors," *Methods*, 2000; 22:373-381.

Ryu et al., "Torque-generating units of the flagellar motor of *Escherichia coli* have a high duty ratio," *Nature*, 2000; 403:444-447.

Sassanfar et al., "An RNA motif that binds ATP," *Nature*, 1993; 364:550-553.

Sarver et al., "Ribozymes as potential anti-HIV-1 therapeutic agents," *Science*, Mar. 9, 1990 ; 247:1222-1225.

Serwer, "Models of Bacteriophage DNA Packaging Motors," *J. Struct. Biol.*, 2003; 141:179-188.

Seth, "Mechanism of Adenovirus-Mediated Endosome Lysis: Role of the Intact Adenovirus Capsid Structure," *Biochem. Biophys. Res. Comm.*, Dec. 15, 1994; 205(2):1318-1324.

Shu et al., "Construction of a switchable 30-nm phi29 DNA packaging nanomotor driven by six ATP-binding RNAs," Poster Abstract No. 2618. 206$^{th}$ Meeting of the Electrochemical Society, Inc. 2004 Joint International Meeting: Oct. 3-8, 2004 in Honolulu, HI. Available online [retrieved Jul. 3, 2007]. Retrieved from the Internet: <http://www.electrochem.org/d1/ma/206/pdfs/2618.pdf>; 1 pg.

Simpson et al., "Structure of the bacteriophage $\phi$29 DNA packaging motor," *Nature*, 2000; 408:745-750.

Smith et al., "The bacteriophage phi29 portal motor can package DNA against a large internal force," *Nature*, Oct. 18, 2001; 413:748-752.

Soong et al., "Powering an inorganic nanodevice with a biomolecular motor," *Science*, 2000; 290:1555-1558.

Sosa et al., "ADP-induced rocking of the kinesin motor domain revealed by single-molecule florescence polarization microscopy," *Nat. Struct. Biol.*, 2001; 8:540-544.

*State Key Laboratory of Molecular Biology Institute of Biochemistry and Cell Biology. Chinese Academy of Sciences*, [online], [retrieved on Mar. 3, 2003]. Retrieved from the Internet: <URL:http://www.slmb.labs.gov.cn/newp4.html>; 2 pgs.

Sun et al., "Controlling bacteriophage phi29 DNA-packaging motor by addition of discharge of a peptide at N-terminus of connector protein that interacts with pRNA," 2006 Nucleic Acids Research 34(19):5482-5490.

Suzuki et al., "Adenovirus-mediated ribozyme targeting of HER-2/neu inhibits in vivo growth of breast cancer cells," *Gene Ther.*, Feb. 2000; 7(3):241-8.

Svoboda et al., "Force and velocity measured for single kinesin molecules," *Cell*, 1994; 77:773-784.

Tatusova et al., "Blast 2 Sequences, a new tool for comparing protein and nucleotide sequences," *FEMS Microbiol. Lett.*, May 15, 1999; 174(2):247-50.

Trottier et al., "DNA-packaging pRNA as target for complete inhibition of viral assembly in vitro and in vivo," *Nucleic Acids Symposium Series*, 1997; 36: 187-9.

Tuerk et al., "Systematic evolution of ligands by exponential enrichment: RNA ligands to bacteriophage T4 DNA polymerase," *Science*, Aug. 1990; 249(4968):505-510.

Vale et al., "Direct observation of single kinesin molecules moving along microtubules," *Nature*, 1996; 380:451-453.

Varambally et al., "The polycomb group protein EZH2 is involved in progression of prostate cancer," *Nature*, Oct. 10, 2002; 419:624-629.

Vinuela et al., "Structure and assembly of phage phi29," *Philosophical Transactions of the Royal Society of London—Series B: Biological Sciences*, 1976; 276:29-35.

Volpe et al., "Regulation of heterochromatic silencing and histone H3 lysine-9 methylation by RNAi," *Science*, 2002; 297:1833-1837.

Wang et al., "Retrovirus-mediated transfer of anti-MDR1 ribozymes fully restores chemosensitivity of P-glycoprotein-expressing human lymphoma cells," *Human Gene Therapy*, May 1, 1999; 10(7):1185-95.

Wichitwechkarn et al., "Mutant prohead RNAs in the in vitro packaging of bacteriophage phi29 DNA-gp3," *J. Mol. Biol.*, 1992; 223(4):991-8.

Wichitwechkarn et al., "Prohead RNA of bacteriophage phi29: size stiochiometry and biological activity," *Nucl. Acids Res.*, 1989; 17:3459-68.

Wong et al., "Allosteric effects of nucleotide cofactors on *Escherichia coli*rep helicase-DNA binding," *Science*, 1992; 256:350-355.

Wyszko et al., "The specific hydrolysis of HIV-1 TAR RNA element with the anti-TAR hammerhead ribozyme: structural and functional implications," *International Journal of Biological Macromolecules*, 2001; 28:373-380.

Xiao et al., "Binding of pRNA to the N-terminal fourth amino acids of connector protein of bacteriaphage phi29," 2005 *Nucl. Acids Res.* 33(8):2640-2649.

Yant et al., "Transposition from a gutless adeno-transposon vector stabilizes transgene expression in vivo," *Nat. Biotechnol.*, Oct. 2002; 20(10):999-1005.

Zern et al., "A novel SV40-based vector successfully transduces and expresses an alpha 1-antitrypsin ribozyme in a human hepatoma-derived cell line," *Gene Ther.*, Jan. 1999; 6(1):114-20.

Zhang, C. et al., "Chemical modification patterns of active and inactive as well as procapsid-bound and unbound DNA-packaging RNA of bacterial virus Phi29," *Virology*, Mar. 15, 2001; 281:281-93.

Zhang, C. et al., "The proximate 5' and 3' ends of the 120-base viral RNA (pRNA) are crucial for the packaging of bacteriophage phi29 DNA," *Virology*, 1994; 201:77-85.

Zhang, C. et al., "Inhibition of phage phi29 assembly by antisense oligonucleotides targeting viral pRNA essential for DNA packaging," *Virology*, 1995; 211:568-76.

Zhang, F. et al., "Function of hexameric RNA in packaging of bacteriophage phi29 DNA in vitro," *Mol. Cell.*, 1998; 2:141-147.

Zilberman et al., "Argonaute4 Control of Locus-Specific siRNA Accumulation and DNA and Histone Methylation," *Science*, Jan. 31, 2003; 299(5607):716-719.

Zuker, "On Finding All Suboptimal Foldings of an RNA Molecule," *Science*, Apr. 7, 1989; 244(4900):48-52.

\* cited by examiner

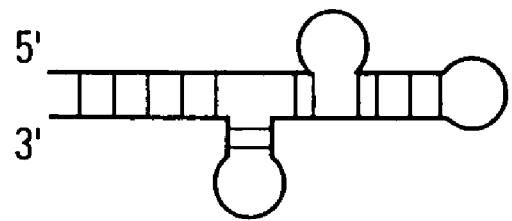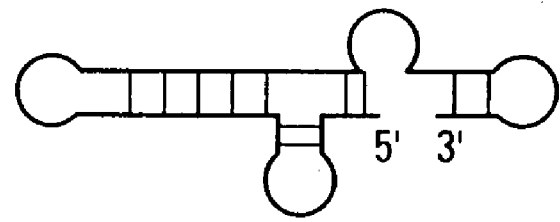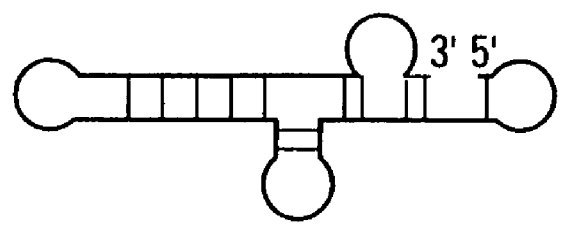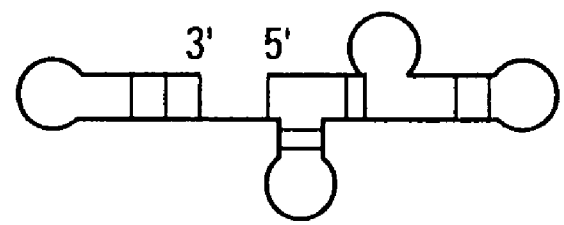
Fig. 5b

| Name of RNA | Activity | Sequence of 3' overhang | 3'overhang base number | Structure |
|---|---|---|---|---|
| Eco-pRNA | $10^8$ | AA GCC GAA UU (SEQ ID NO:19) | 10 bases | 3' overhang 10 bases |
| XbHi-pRNA | $10^8$ | AAGCCGAAUUCC AGCACACUGGCG GCCGUUACUAGU GGAUCCGAGCUC GGUACCAAGCU (SEQ ID NO:20) | 59 bases | 3' overhang 59 bases |
| 174-pRNA | $10^8$ | CCUUUACAUGC GACACAGACGAA GCGCUAAAACGU GGGAUUCUGUG UCGUUUU (SEQ ID NO:21) | 54 bases | 3' overhang 50 bases |
| Di-RNA | $10^8$ | UCAAUGGUACGG UACUUCCAUUGU CAUGUGUAUGUU GGGGAUUAAACC CUGAUUGAGUUC AGCCCACAUACU UUGUUGAUUGGU UGUCAAUCAUGG CAAAAGUGCACG CUACUUUGAUAA (SEQ ID NO:22) | 120 bases | 3' overhang 120 bases |

Fig. 10

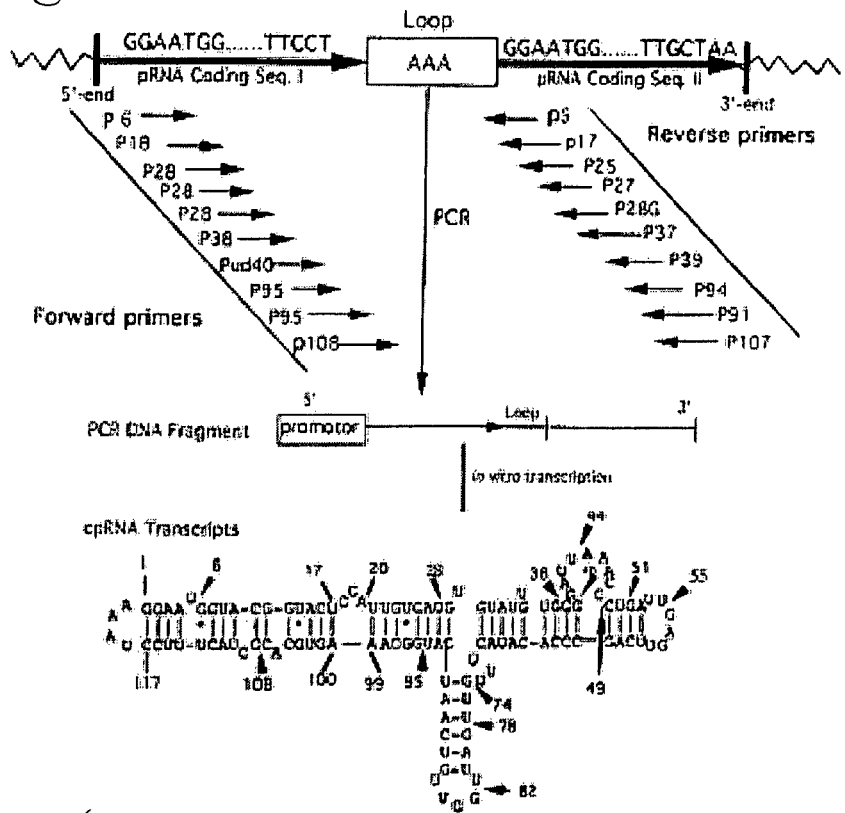
Fig. 11a  Small loop inserted
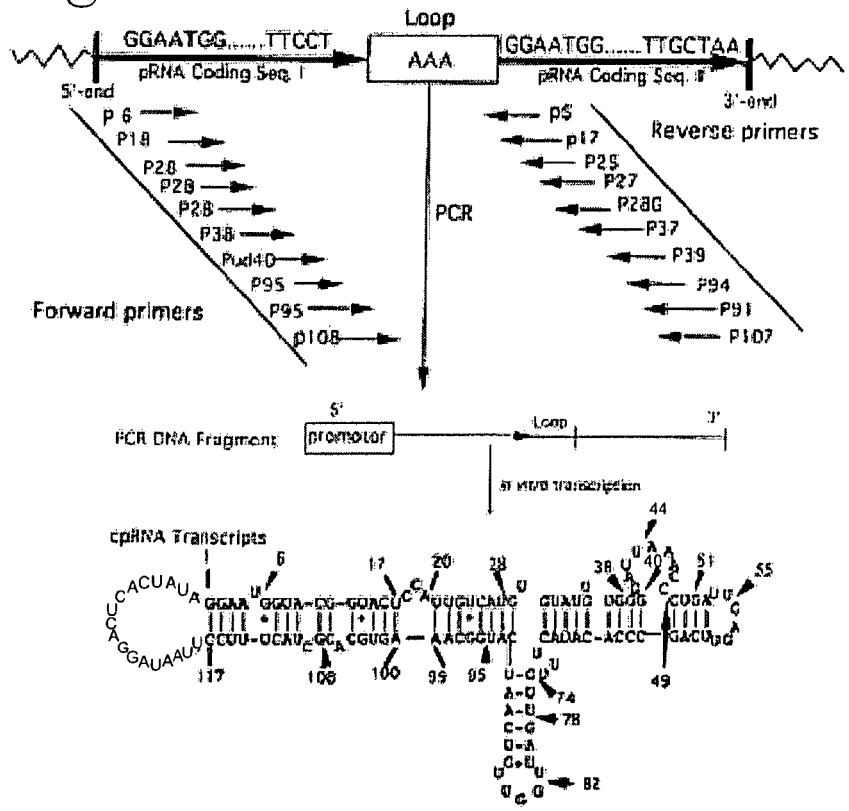
Fig. 11b  Large loop inserted

Fig. 13a

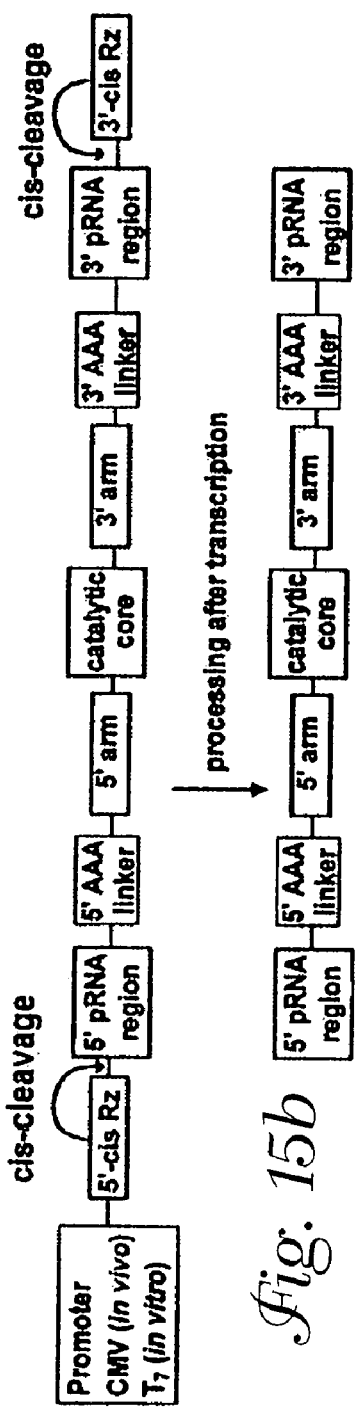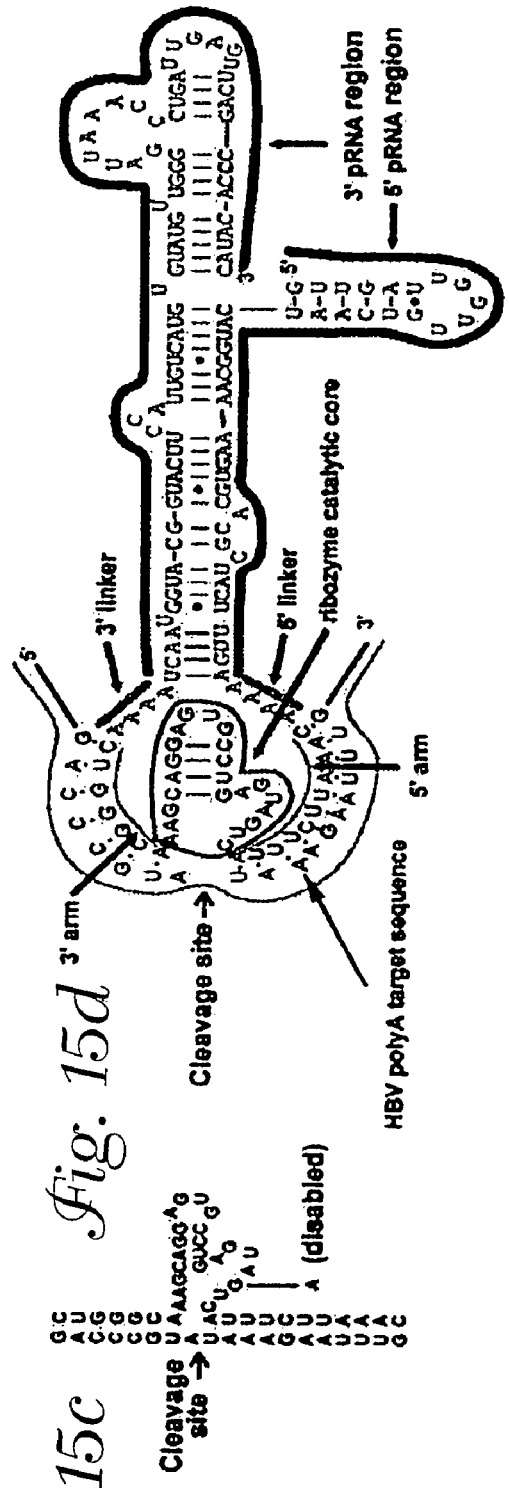

PRNA CHIMERA

This application claims the benefit of U.S. provisional patent application Ser. No. 60/433,697, filed Dec. 16, 2002, and also is a continuation-in-part patent application of PCT/US01/26333, filed Aug. 23, 2001, which claims the benefit of U.S. provisional patent application Ser. No. 60/227,393, filed Aug. 23, 2000, each of which patent applications is incorporated herein by reference in its entirety.

STATEMENT OF GOVERNMENT RIGHTS

This invention was made with government support under grants from the National Institutes of Health (Grant No. GM59944 and Grant No. GM48159) and the National Science Foundation (Grant No. MCB-9723923). The government has certain rights in this invention.

BACKGROUND

A ribozyme is an RNA molecule capable of cleaving a target RNA molecule, or carrying out other catalytic and enzymatic functions. Structurally, it is single-stranded RNA characterized by two "arms" positioned either side of a small loop. The ribozyme base pairs to a region on the target RNA that is complementary to the nucleotide sequence of its two arms. The loop region serves as an active catalytic center that performs the cleaving function on the target RNA (FIG. 1).

The use of ribozymes for treatment and prevention of diseases in plants, humans and animals has the potential to revolutionize biotechnology. Hammerhead ribozymes have, for example, been used to cleave RNA in transgenic plants and animals. However, despite numerous publications reporting the results of investigations in test tubes, reports on the successful use of hammerhead ribozymes in living organisms are relatively few (Perriman et al., *Proc. Natl. Acad. Sci. USA* 92:6175-6179 (1995)). Although it is clear that hammerhead ribozymes can cleave specific viral RNA or mRNA in test tubes, the efficiency of cleavage in cells is dramatically reduced due to instability and misfolding of the ribozyme in cells.

A major cause for the instability of ribozymes in an intracellular environment is degradation of the ribozyme by exonuclease present in the cells (Cotton et al., *EMBO J.* 8:3861-3866 (1989)). Exonucleases are enzymes that nonspecifically trim RNA from both ends. One method that has been used to block the intracellular degradation of ribozymes is to protect the ribozyme by connecting it at one end to a vector RNA, such as tRNA (Vaish et al., *Nucl. Acids Res.* 26:5237-5242 (1998)). However, due to refolding of the resulting chimera RNA, the ribozyme varied in efficiency compared to the unprotected ribozyme (Bertrand et al., *RNA* 3:75-88 (1997)). Tethering of a ribozyme to both ends of a tRNA has also been reported, but folding and/or activity was compromised (Vaish et al., *Nucl. Acids Res.* 26:5237-5242 (1998)).

The potential to treat disease by using ribozymes to cleave RNA involved in cancer and pathogen infection is tremendous. The availability of a stabilized ribozyme that is resistant to degradation and is correctly folded such that it remains active in an intracellular environment would pave the way for the development of many important medical therapies.

SUMMARY OF THE INVENTION

The invention provides a circularly permuted chimeric pRNA molecule carrying a stabilized, properly folded, biologically active moiety. The pRNA chimera is formed from a circularly permuted pRNA region, and a spacer region that includes the biologically active moiety. The biologically active moiety is not limited to any chemical structure but is preferably an RNA, such as a ribozyme, siRNA (small, interfering RNA) or an antisense RNA. The spacer region is covalently linked at its 5' and 3' ends to the pRNA region. Optionally, the spacer region includes first and second nucleotide strings interposed between the biologically active moiety and the pRNA region.

The invention circularly permuted chimeric pRNA of the invention can be monomeric or multimeric. When multimeric, the circularly permuted pRNA is preferably a dimer or a hexamer, allowing the multimeric complex to be polyvalent. In a polyvalent multimeric complex, the multiple biologically active moieties may be the same or different. The multimeric complex may advantageously contain one or more biologically active moieties that facilitate specific targeting to deliver one or more therapeutic agents carried at other valency sites by the circularly permuted pRNA, such as biological moieties involved in cell surface binding, membrane diffusion or endocytosis. For example, the SELEX approach has been commonly used to screen for RNA aptamers that bind cell surface markers (Ellington et al., *Nature* 346, 818-822 (1990); Tuerk et al., *Science* 249, 505-510 (1990)). Such RNA aptamers can be attached to one of more subunits of the pRNA dimer or hexamer for specific cell recognition during delivery of the therapeutic agent. Other biological active moieties that can be included in the multimeric complex include those involved in intracellular targeting and release of the therapeutic agent, and the like.

The pRNA region has a compact stable secondary structure characteristic of bacteriophage pRNA sequences. Thus, in one embodiment of the pRNA chimera, the pRNA region includes a circularly permuted pRNA of a bacteriophage selected from the group consisting of φ29, SF5', B103, PZA, M2, NF and GA1. In another embodiment of the pRNA chimera, the pRNA region includes:

(i) in the 5' to 3' direction beginning at the covalent linkage of the pRNA with the 3' end of the spacer region
  a first loop;
  a second loop; and
  a lower stem-loop structure comprising a bulge,
  a first stem section and a third loop;
(ii) a second stem section interposed between the spacer region and the stem-loop structure;
(iii) a third stem section interposed between the stem-loop structure and the first loop;
(iv) a fourth stem section interposed between the first loop and the second loop; and
(v) an opening defining 5' and 3' ends of the pRNA chimera, positioned anywhere within the pRNA region.

The invention also provides a method for making a pRNA chimera of the invention. A DNA encoding a pRNA chimera containing a pRNA region and a spacer region that includes a biologically active RNA is transcribed in vitro to yield the pRNA chimera. Optionally, the DNA encoding the pRNA chimera is generated using polymerase chain reaction on a DNA template, or the DNA is generated by cloning the DNA into a plasmid and replicating the plasmid.

The invention further provides a method for determining whether an RNA molecule interacts with a test molecule. A pRNA chimera that includes the RNA molecule of interest is immobilized on a substrate, then contacted with test molecule. Whether or not the test molecule interacts with the RNA of interest, such as by binding the RNA of interest, is then detected.

The invention also provides a DNA molecule that includes a nucleotide sequence that encodes a pRNA chimera containing a pRNA region and a spacer region that includes a biologically active RNA.

Also provided by the invention is a method for delivering a biologically active RNA to a cell, preferably a plant cell or an animal cell, such as human cell. In one embodiment, a DNA molecule having a nucleotide sequence that operably encodes a pRNA chimera of the invention is introduced into the cell and transcribed to yield the biologically active RNA. In another embodiment, the pRNA chimera is directly transfected into the cell. Alternatively, the chimeric RNA complex can be delivered to the cell via the incorporation of a RNA aptamers that specifically bind to cell surface markers (Ellington et al., Nature 346, 818-822 (1990); Tuerk et al., Science 249, 505-510 (1990)).

BRIEF DESCRIPTION OF THE FIGURES

FIG. 10 presents the impact of various extensions (SEQ ID NOs: 19-22) of the 3' end of the pRNA on viral activity as measured by plaque forming units.

FIG. 11 depicts the design and production of circularly permutated pRNAs. The DNA template in (a) (SEQ ID NO:2) uses a short (AAA) sequence, shown here with flanking sequences (SEQ ID NO:30), to join the native 5'/3' ends, while the template in (b) (SEQ ID NO:29) uses a longer sequence (SEQ ID NO:8), shown here with flanking sequences (SEQ ID NO:31), to join the native 5'/3' ends. New openings of the cpRNA are indicated by the wedges pointing to places in the transcript sequence. (See Zhang et al., RNA 3:315-323 (1997)).

FIG. 15 depicts the design and construction of plasmid encoding the self-process ribozyme targeting at the HBV polyA signal. (a) shows the design of plasmid encoding ribozyme pRNA-RzA. (b) shows the processed chimeric ribozyme after transcription and cis-cleavage. (c) shows the secondary structure of the hammerhead ribozyme (RzA) (SEQ ID NO:23) base paired to the HBV polyA target sequence (SEQ ID NO:24). An indicated change from "G" to "A" generated an inactive enzyme as negative control. (d) shows secondary structure of the ribozyme pRNA-RzA (SEQ ID NO:25) base paired to the HBV polyA substrate (SEQ ID NO:24).

DETAILED DESCRIPTION

Figure 1:
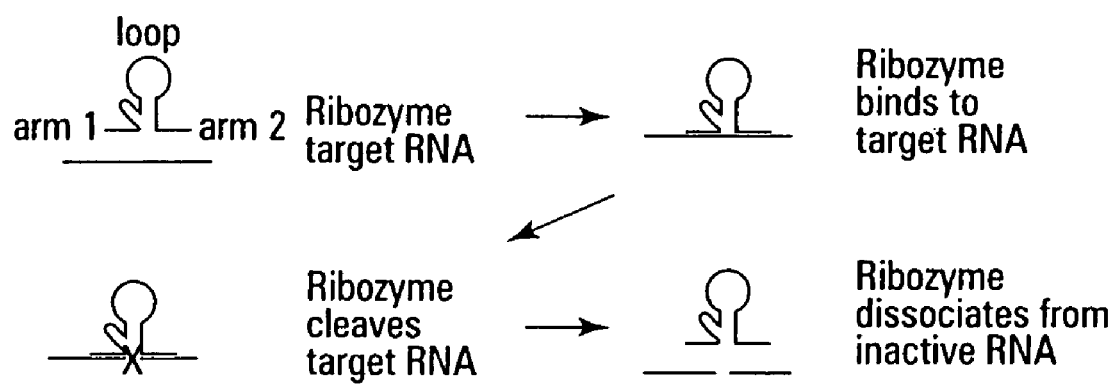
FIG. 1 is a schematic depiction of target RNA cleavage by a representative ribozyme.

Bacteriophage ϕ29 (phi29) is a double-stranded DNA virus. In 1987, one of the inventors, Dr. Peixuan Guo, discovered a viral-encoded 120 base RNA that plays a key role in bacteriophage ϕ29 DNA packaging (Guo et al. Science 236: 690-694 (1987)). This RNA is termed packaging RNA or "pRNA". It binds to viral procapsids at the portal vertex (the site where DNA enters the procapsid) (Guo et al., Nucl. Acids Res. 15:7081-7090 (1987)) and is not present in the mature ϕ29 virion.

Six copies of pRNA are needed to package one genomic DNA (Trottier et al., J. Virol. 70:55-61 (1996); Trottier et al., J. Virol. 71, 487-494 (1997); Guo et al., Mol. Cell. 2, 149-155 (1998)). DNA packaging is completely blocked when one of the six slots is occupied by one inactive pRNA with a mutation at the 5' or 3' end (Trottier et al., J. Virol. 70:55-61 (1996); Trottier et al., J. Virol. 71:487-494 (1997)). Bacteriophage ϕ29 pRNA is associated with procapsids during the DNA translocation process (Chen et al., J. Virol. 71:3864-3871 (1997)). Inhibition data also suggests that the pRNA plays an essential role in DNA translocation (Trottier et al., J. Virol.

71:487-494 (1997)); Trottier et al. *J. Virol.* 70:55-6 (1996)). A $Mg^{2+}$-induced conformational change of pRNA leads to its binding to the portal vertex (Chen et al. *J. Virol.* 71, 495-500 (1997)). The tertiary structure of the pRNA monomer and dimer has also reported (Zhang et al., *Virology* 81:281-93 (2001); Trottier et al., *RNA* 6(9):1257-1266 (2000); Chen et al. *J. Biol. Chem.* 275(23): 17510-17516 (2000); Garver et al., *J. Biol. Chem.* 275(4): 2817-2824 (2000)).

Recently, a computer model of the three-dimensional structure of a pRNA monomer has been constructed (Hoeprich and Guo, *J. Biol. Chem.* 277:20794-803 (2002)) based on experimental data derived from photo-affinity cross-linking (Garver and Guo, *RNA* 3:1068-79 (1997); Chen and Guo, *J Virol* 71:495-500(1997)); chemical modification and chemical modification interference (Mat-Arip et al., *J Biol Chem* 276:32575-84 (2001); Zhang et al., *Virology* 281:281-93 (2001); Trottier et al., *RNA* 6:1257-66 (2000)); complementary modification (Zhang et al., *RNA* 1:1041-50 (1995); Zhang et al., *Virology* 201:77-85 (1994); Zhang et al., *RNA* 3:315-22 (1997); Reid et al., *J Biol Chem* 269:18656-61 (1994); Wichitwechkarn et al., *Mol Biol* 223:991-98 (1992)); nuclease probing (Chen and Guo, *J Virol* 71:495-500 (1997); Reid et al., *J Biol Chem* 269:5157-62 (1994); Zhang et al., *Virology* 211:568-76 (1995)); oligo targeting competition assays (Trottier and Guo, *J Virol* 71:487-94 (1997); Trottier et al., *J Virol* 70:55-61(1996)) and cryo-atomic force microscopy (Mat-Arip et al., *J Biol Chem* 276:32575-84 (2001); Trottier et al., *RNA* 6:1257-66 (2000); Chen et al., *J Biol Chem* 275:17510-16 (2000)). pRNA hexamer docking with the connector crystal structure reveals a very impressive match with available biochemical, genetic, and physical data concerning the 3D structure of pRNA (Hoeprich and Guo, *J Biol Chem* 277:20794-803 (2002)).

Figure 2A:
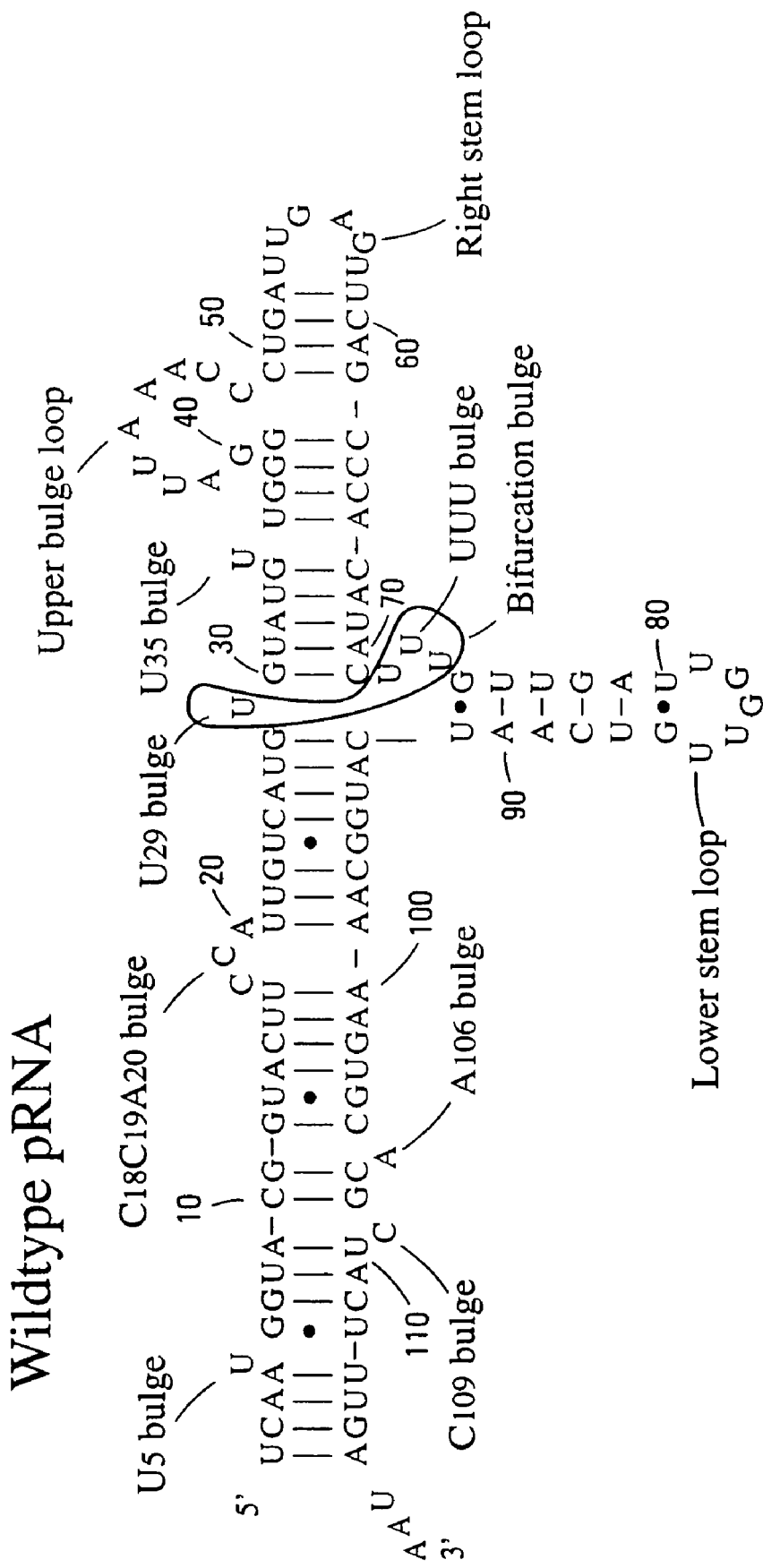
FIG. 2 depicts the nucleotide sequence (SEQ ID NO:1) and secondary structure of wild-type ϕ29 (phi29) pRNA indicating (a) the location and nomenclature of the loops and bulges (Zhang et al., RNA 3:315-323 (1997)); and (b) pRNA sequence and secondary structure (SEQ ID NO:27), showing the procapsid binding domain and the DNA packaging domain; the right and left-hand loops, the head loop, $U^{72}U^{73}U^{74}$ bulge, and the $C^{18}C^{19}A^{20}$ bulge are in boxes; the DNA-packaging domain (5'/3' ends) and the procapsid binding domain (the larger area) are shaded; the curved line points to the two interacting loops; note that the three base UAA 3' overhang shown in (a) is absent in this diagram.

The nucleotide sequence (SEQ ID NO: 1) of native full length φ29 pRNA (Guo et al., *Nucl. Acids Res.* 15:7081-7090 (1987)), as well as its predicted base-paired secondary structure, is shown in FIG. 2(a) (Zhang et al., *RNA* 3:315-323 (1997); Zhang et al., *Virology* 207:442-451 (1995)). The predicted secondary structure has been partially confirmed (Zhang et al., *RNA* 1:1041-1050 (1995); Reid et al., *J. Biol. Chem.* 269:18656-18661 (1994); Zhang et al., *Virology* 201: 77-85 (1994); Chen et al., *J. Virol.* 71: 495-500 (1997)).

Figure 2B:
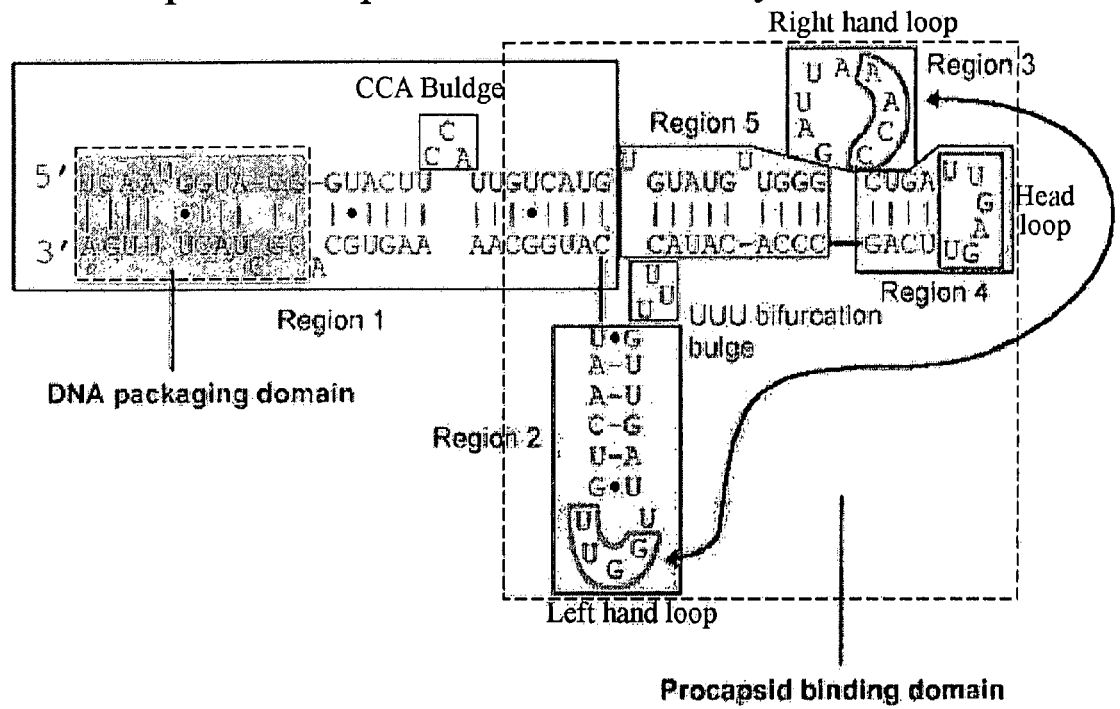

As shown in FIG. 2(b), the pRNA monomer contains two functional domains, the procapsid binding domain and the DNA translocating domain. The procapsid binding domain is located at the central part of the pRNA molecule at bases 23-97 (Garver et al., *RNA* 3:1068-79 (1997); Chen et al., *J Biol Chem* 275:17510-16 (2000)), while the DNA translocation domain is located at the 5'/3' paired ends. The 5' and 3' ends have been found to be proximate, and several kinds of circularly permuted pRNA have been constructed (Zhang et al., *RNA* 3:315-22 (1997); Zhang et al., *Virology* 207:442-51 (1995); Guo, *Prog in Nucl Acid Res & Mole Biol* 72:415-72 (2002)). These two domains are compact and fold independently, suggesting that exogenous RNA can be connected to the end of the pRNA without affecting pRNA folding and that phi29 pRNA could be used as a vector to escort and chaperone small therapeutic RNA molecules.

Phylogenetic analysis of pRNAs from phages SF5', B103, φ29, PZA, M2, NF and GA1 (Chen et al., *RNA* 5:805-818 (1999)) shows very low sequence identity and few conserved bases, yet the family of pRNAs appear to have strikingly similar and stable predicted secondary structures (FIG. 3). The pRNAs from bacteriophages 5F5', B103, φ29/PZA (SEQ ID NO:1), M2/NF, GA1 of *Bacillus subtilis* (Chen et al., *RNA* 5:805-818 (1999); and aptRNA are all predicted to have a secondary structure that exhibits essentially the same structural features as shown in FIG. 2 for φ29 pRNA (Chen et al., *RNA* 5:805-818 (1999)). All have native 5' and 3' ends at the left end of a stem structure (as shown in FIG. 3) and contain the same structural features positioned at the same relative locations.

The pRNA of these bacteriophages, sharing as they do a single stable secondary structure, provide the framework for the pRNA chimera of the invention.

Secondary structure in an RNA molecule is formed by base pairing among ribonucleotides. RNA base pairs commonly include G-C, A-T and U-G. Predictions of secondary structure are preferably made according to the method of Zuker and Jaeger, for example by using a program known by the trade designation RNASTRUCTURE 3.6, written by David H. Mathews (Mathews et al., *J. Mol. Biol.* 288:911-940 (1999); see also Zuker, *Science* 244:48-52 (1989); Jaeger et al., *Proc. Natl. Acad. Sci. USA* 86:7706-7710 (1989); Jaeger et al., *Meth. Enzymol.* 183:281-306 (1990)). This program is publicly available on the worldwide web at the homepage of the laboratory of Douglas Turner at the University of Rochester at rna.chem.rochester.edu/RNAstructure.html and runs on MS Windows 95, 98, ME, 2000 and NT4. The program is also publicly available on the worldwide web at Michael Zuker's homepage at Rensselaer Polytechnic Institute (bio-info.math.rpi.edu/~zukerm/home.html); his homepage offers online folding and a version of the algorithm that can be compiled on Silicon Graphics, Sun, or DEC Alpha workstations. The structure with the lowest energy (i.e., the optimal structure) is chosen.

Secondary structures of RNA can be characterized by stems, loops and bulges. A "stem" is a double-stranded section of two lengths of base-paired ribonucleotides. Stem sections contain at least 2 base pairs and are limited in size only by the length of the RNA molecule. A "loop" is a single-stranded section that typically includes at least 3 ribonucleotides and is also limited in size only by the length of the RNA molecule. In a "stem loop", the 5' and 3' ends of the loop coincide with the end of a base-paired stem section. In a "bulge loop", the loop emerges from along the length of a stem section. The 5' and 3' ends of a bulge loop are typically not base paired although they may potentially be (see, e.g., G40 and C48 of the bulge loop in the φ29 pRNA structure; FIG. 2). A "bulge" is an unpaired single stranded section of about 1 to about 6 ribonucleotides present along the length of (or between) stem sections. Note that there is no clear line between a large "bulge" and a small "bulge loop." Herein, where the term "bulge" is used, it also includes a small "bulge loop" (i.e., a bulge loop of less than about 7 ribonucleotides).

The secondary structure of an RNA molecule is determined by the nature and location of the base pairing options along its length. RNA secondary structure is degenerate; that is, different primary ribonucleotide sequences can yield the same base pairing configurations and hence the same secondary structure. In a way, it is akin to the way multiple amino acid sequences can produce the same secondary structure, for example an α-helix.

A single secondary structure is dictated by a number of different primary sequences in predictable and well-understood ways. For example, single or pairs of nucleotides can generally be added, removed, or substituted without altering the overall base pairing interactions within the RNA molecule and without interfering with its biological function. This is particularly true if one or a few base pairs of nucleotides are removed, added or substituted along double-stranded hybridized length of the molecule, or if one or more nucleotides is removed, added or substituted in the single-stranded loop regions. For example, although GC base pairs and AT base pairs differ slightly in their thermodynamic stability, one can generally be substituted for another at a site within the double-stranded length without altering the secondary structure of an RNA molecule. GC base pairs are preferred in the stem region due to their added stability. Changes in secondary structure as a result of addition, deletion or modification of nucleotides can be readily assessed by applying the secondary structure prediction algorithm of Zuker and Jaeger as described above. The pRNA region of the RNA chimera can accommodate substantial variation in primary sequence without an appreciable change in secondary structure.

The pRNA chimera of the invention consists essentially of a pRNA region having the secondary structure exemplified in FIG. 3 (and schematically depicted in FIG. 4, as detailed below), interrupted by (i.e., flanking) a heterologous spacer region that contains a biologically active moiety, such as a ribozyme. The secondary structure of the pRNA region of the pRNA chimera is the common secondary structure that characterizes the pRNA from bacteriophages φ29, SF5', B103, PZA, M2, NF and GA1. The spacer region is termed "heterologous" because all or a portion of its nucleotide sequence is engineered or it is obtained from an organism other than the bacteriophage. It is the presence of the heterologous spacer region that renders the construct "chimeric" for the purposes of this invention. The pRNA chimera is useful as a vehicle to carry and deliver a ribozyme or other biologically active moiety to a target molecule or location. Since both ends of the ribozyme are connected to pRNA, the linkage is expected to protect the sensitive ribozyme from degradation and to assist the biologically active moiety to fold appropriately.

Notably, the ability of the pRNA chimera to perform its intended function of protecting and carrying a biologically active moiety depends not on the primary nucleotide sequence of the pRNA region (the primary structure), but on the secondary structure (base pairing interactions) that the pRNA region assumes as a result of its primary ribonucleotide sequence. The "pRNA region" of the pRNA chimera is so termed because it has a secondary structure, although not necessarily an RNA sequence, characteristic of a native bacteriophage pRNA molecule. Therefore, unless otherwise specified, the term "pRNA region" as used herein includes naturally occurring (native) pRNA sequences, normaturally occurring (normative) sequences, and combinations thereof provided that they yield the secondary structure characteristic of naturally occurring (native) bacteriophage pRNA as described herein. Stated another way, the term "pRNA region" is not intended to be limited to only those particular nucleotide sequences native to pRNA. The pRNA region can thus contain any nucleotide sequence which results in the secondary structure shown in FIG. 4. Nucleotide sequences that fold into the aforesaid secondary structure include naturally occurring sequences, those that are derived by modifying naturally occurring pRNA sequences, and those that are designed de novo, as well as combinations thereof. One of skill in the art can readily determine whether a nucleotide sequence will fold into the secondary structure shown in FIG. 4 and described herein by applying a secondary structure algorithm, such as RNASTRUCTURE as described above, to the nucleotide sequence.

Examples of nucleotide sequences that, when folded, yield the secondary structure of the pRNA region of the pRNA chimera of the invention are shown in FIG. 3. They include pRNA sequences from bacteriophages SF5', B103, φ29/PZA, M2/NF, GA1 as well as the aptRNA.

In embodiments of the pRNA chimera wherein the pRNA region includes or is derived from a naturally occurring pRNA, the spacer region of the pRNA chimera is covalently linked to the pRNA region at what can be considered the "native" 5' and 3' ends of a pRNA sequence, thereby joining the native ends of the pRNA region. The pRNA region of the pRNA chimera is optionally truncated when compared to the native bacteriophage pRNA; in those embodiments, and that as a result the "native" 5' and 3' ends of the pRNA region simply refer to the nucleotides that terminate or comprise the actual end of the truncated native pRNA. An opening is formed in the pRNA region to linearize the resulting pRNA chimera, effecting a "circular permutation" of the pRNA as detailed below. It should nonetheless be understood that the term "circularly permuted pRNA region" is not limited to naturally occurring pRNAs that have been circularly permuted but instead is intended to have the broader meaning of RNA having a pRNA-like secondary structure as shown in FIG. 4(c), including an opening in the pRNA region that forms the 5' and 3' ends of the pRNA chimera.

Examples of pRNA chimera of the invention are those formed from the pRNAs of bacteriophages SF5, B103, φ29/PZA (SEQ ID NO:1), M2/NF, GA1 as well as aptRNA by joining the native 5' and 3' ends to the spacer region and introducing an opening elsewhere in the pRNA region, as described herein. Another example of a pRNA chimera of the invention is: 5'-GUUGAUN$_j$GUCAAUCAUGGCAA (SEQ ID NO:7)-spacer region-UUGUCAUGUGUAUGUUGGG-GAUUAN$_j$CUGAUUGAGUUCAGCCCACAUAC-3' (SEQ ID NO:32)

where N represents any nucleotide, without limitation and j is an integer between about 4 to about 8. Preferably j is 4 or 5. The spacer region is represented by $N_m$-B-$N_n$ where $N_n$ and $N_m$ are nucleotide strings that are optionally included in the spacer region, and B includes the biologically active moiety. Preferably, B is a ribonucleotide sequence that includes a biologically active RNA. Both m and n can be independently zero or any integer. Preferably, m and n are independently at least about 3, more preferably at least about 5, and most preferably at least about 10. Further, n and m are independently preferably at most about 300, more preferably at most about 50, and most preferably at most about 30.

Further, since the pRNA region of the pRNA chimera is defined by its secondary structure, still other examples of a pRNA chimera can be readily made by "mixing and matching" nucleotide fragments from, for example, SEQ ID NOs: 1, 2, 3, 7, 11, 12, 13, 14, 15, 16, 33, 34, 35, 36, 37 and 38 that fold into particular secondary structural features (bulges, loops, stem-loops, etc.) provided that the resulting nucleotide sequence folds into the overall secondary structure as shown in FIG. 4. For example, nucleotides encoding bulge loop 22 from bacteriophage SF5' pRNA (SEQ ID NO:11) could be substituted for the nucleotides encoding bulge loop 22 in the φ29 pRNA (SEQ ID NO:1) to yield a pRNA region as described herein. Likewise, any number of artificial sequences can be substituted into SEQ ID NOs: 1, 2, 3, 7, 11, 12, 13, 14, 15, 16, 33, 34, 35, 36, 37 and 38 to replace nucleotide sequences that fold into one or more structural features (or portions thereof) to form a pRNA region as described herein. See, for example, aptRNA (FIG. 3(f)) which was derived in that fashion from φ29 pRNA. The overarching principle is that the overall secondary structure of the pRNA region is the secondary structure common to the bacteriophage pRNAs, as schematically depicted in FIG. 4.

Importantly, the resulting pRNA chimera is not a circular molecule; rather, it is linearized due to a circular permutation of the pRNA region (Zhang et al., *RNA* 3:315-323 (1997); Zhang et al., *Virology* 207:442-451 (1995)). Briefly, an opening (i.e., a cleavage or break point) is provided in the pRNA region at any designated site to form the actual 5' and 3' ends of the RNA chimera. These 5' and 3' ends are at "normative" positions with respect to a naturally occurring linear pRNA.

Figure 5A:
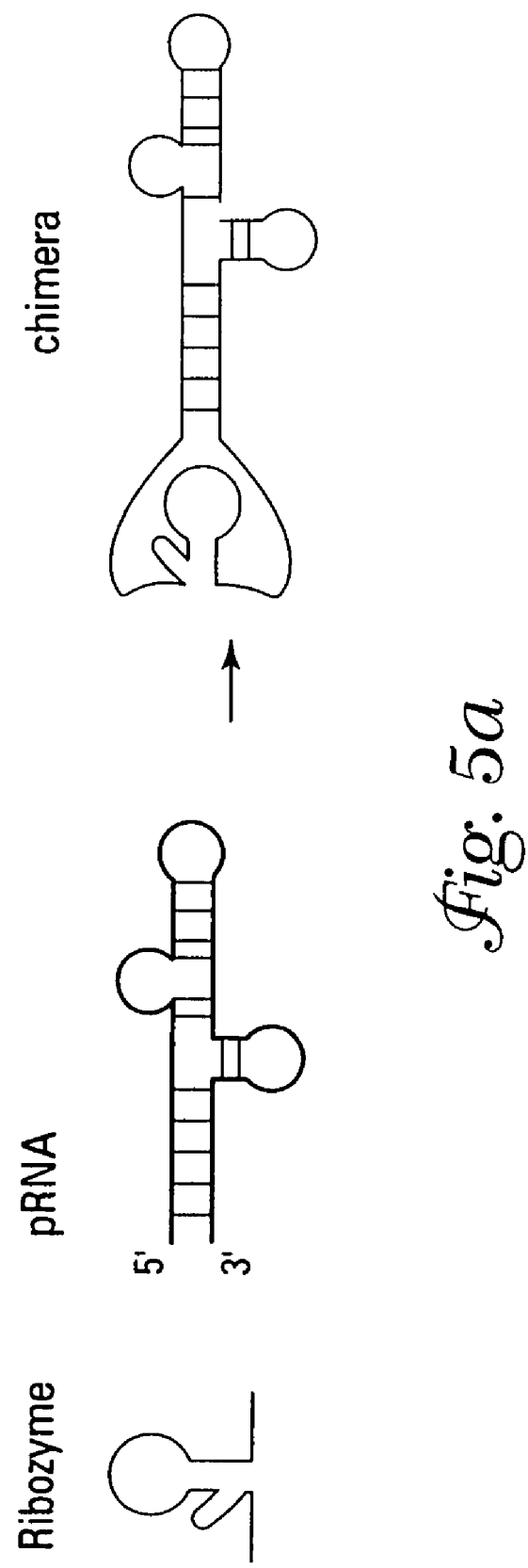
FIG. 5 is a schematic depiction of (a) the design of one embodiment of the pRNA chimera of the invention; and (b) exemplary circularly permuted pRNA (cpRNA) molecules showing various locations for the circle openings.

FIG. 5(a) shows how a pRNA chimera of the invention can be formed from a ribozyme and a pRNA region. The 5' and 3' ends of the pRNA can be engineered into any desired site on the circularly permuted pRNA chimera. FIG. 5(b) shows exemplary circularly permuted RNA molecules showing various locations for the circle openings.

Figure 4A:
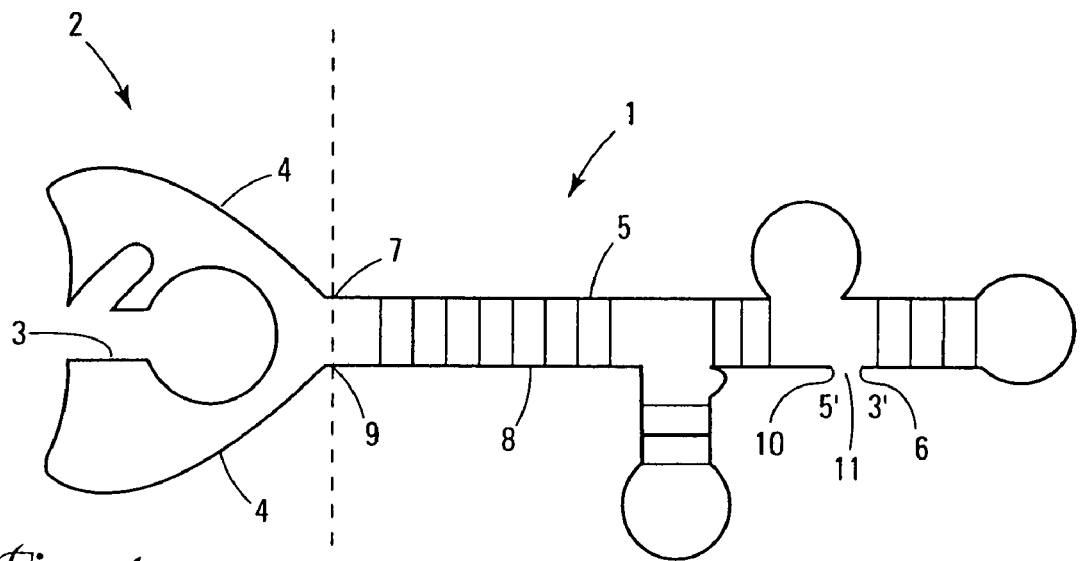
FIG. 4 is a schematic depiction of various structural features of a pRNA chimera of the invention: (a) a whole pRNA chimera; (b) a spacer region component; (c) a pRNA region component.

FIG. 4 depicts various structural features that characterize a pRNA chimera of the invention. As shown in FIG. 4(a), the linear molecule includes a pRNA region 1 and a spacer region 2. Spacer region 2 contains a biologically active moiety 3, in this case a ribozyme, flanked by ribonucleotide strings 4. The pRNA region 1 is bifurcated; it includes a first pRNA segment 5 having 3' end 6 and "native" 5' end 7, and a second pRNA segment 8 having "native" 3' end 9 and 5'end 10. Ends 6 and 10 are the actual terminal ends of the pRNA chimera. Opening 11 renders the molecule linear and can be positioned anywhere in pRNA region 1 by the relocation of ends 6 and 10.

Figure 4B:
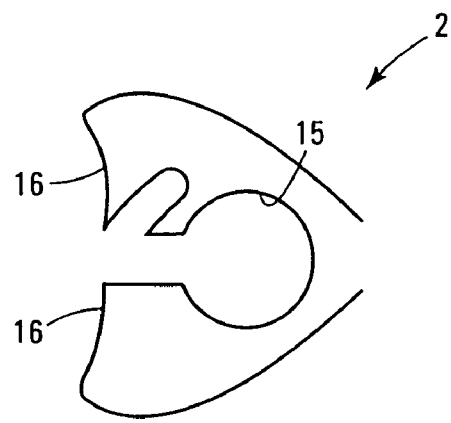
Figure 4C:
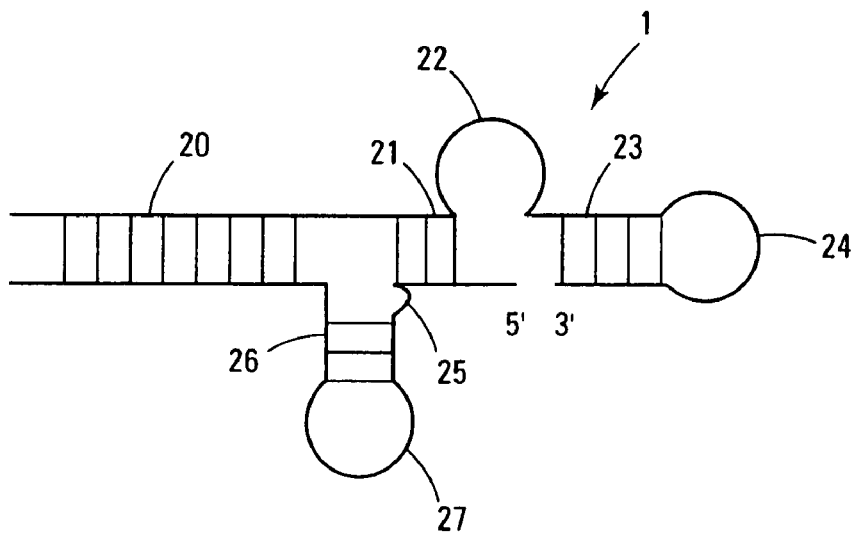

Spacer region 2 is shown in detail in FIG. 4(b). Ribozyme 3 is composed of a catalytic domain 15 flanked by target-binding sequences 16.

pRNA region 1 is shown in detail in FIG. 4(c). Overall, pRNA region 1 is characterized by a stem-loop secondary structure, wherein loop 24 is relatively small and the base-pairing in the stem (essentially stem sections 20, 21 and 23) is interrupted by structures on either side of loop 24. Bulge loop 22 is positioned 5' of loop 24. Positioned 3' of loop 24 is a stem-loop structure that contains bulge 25, stem 26 and loop 27.

Stem section 20 can be any number of ribonucleotides in length and can contain an unlimited number of bulges provided it is still able to base pair. Preferably, stem section 20 contains at least about 4, more preferably at least about 10 base pairs; further, it preferably it contains at most about 50, more preferably at most about 40 base pairs. Preferably stem section 20 contains about 0 to about 8 bulges; more preferably it contains about 0 to about 4 bulges.

Stem section 21 preferably contains 5-13 base pairs and 0-2 bulges.

Bulge loop 22 preferably contains 5-12 bases.

Stem section 23 preferably contains 3-12 base pairs and 0-2 bulges.

Loop 24 preferably contains 3-8 bases.

Bulge 25 preferably contains 0-5 bases.

Stem 26 preferably contains 4-8 base pairs and 0-2 bulges.

Loop 27 preferably contains 3-10 bases.

Tertiary interactions within an RNA molecule may result from nonlocal interactions of areas of the RNA molecule that are not near to each other in the primary sequence. Although native bacteriophage pRNA appears to exhibit tertiary interactions between bulge loop 22 and loop 27 (Chen et al., *RNA* 5:805-818 (1999); Guo et al, *Mol. Cell.* 2:149-155 (1998)) it should be understood that the pRNA chimera of the invention is not limited to RNA molecules exhibiting any particular tertiary interactions.

Figure 3A:
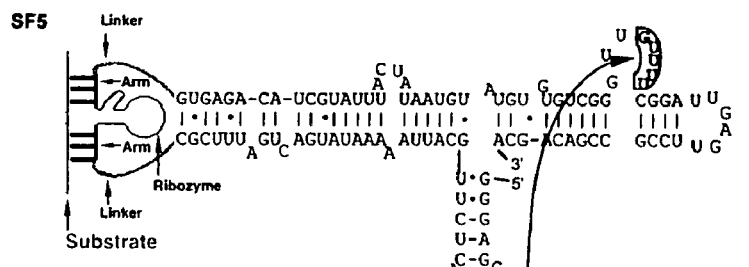
FIG. 3 depicts circularly permuted chimeric nucleotide sequences of several pRNAs: (a) bacteriophage SF5' (SEQ ID NOs:11 and 33), (b) bacteriophage B103 (SEQ ID NOs:12 and 34), (c) bacteriophages ϕ29 and PZA (SEQ ID NOs:13 and 35), (d) bacteriophage M2 and NF (SEQ ID NOs:14 and 36), (e) bacteriophage GA1 (SEQ ID NOs:15 and 37) (Chen et al., RNA 5:805-818 (1999), and (f) aptRNA (SEQ ID NOs: 16 and 38).
Figure 3B:
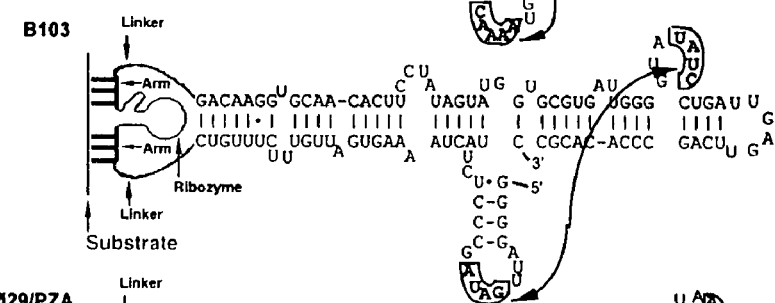
Figure 3C:
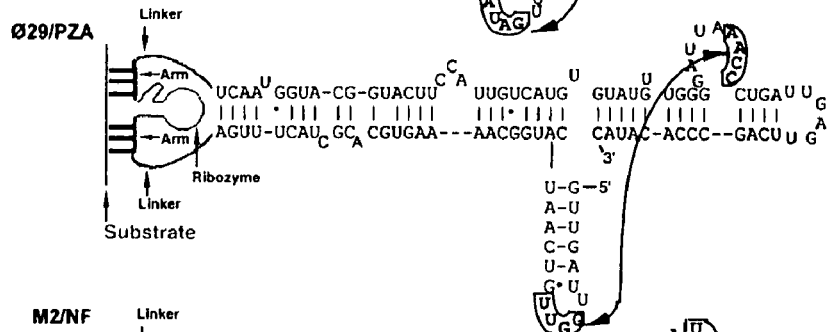
Figure 3D:
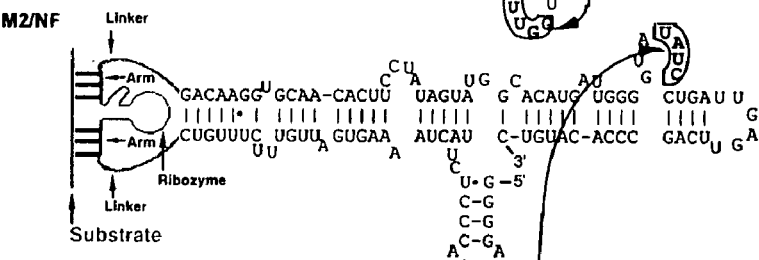
Figure 3E:
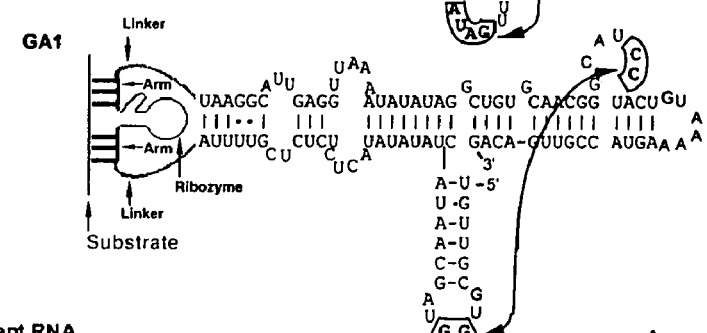
Figure 3F:
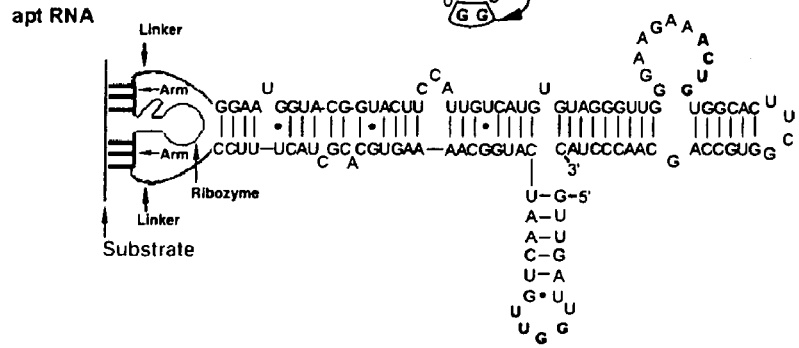

In one embodiment, the pRNA chimera of the invention contains at least 8, more preferably at least 15, most preferably at least 30 consecutive ribonucleotides found in native SF5' pRNA (FIG. 3(a)), B103 pRNA (FIG. 3(b)), φ29/PZA pRNA (FIG. 3(c)), M2/NF pRNA (FIG. 3(d)), GA1 pRNA (FIG. 3(e)), or aptRNA (FIG. 3(f)), preferably native φ29 pRNA. Most preferably, the pRNA region of the pRNA chimera contains at least a φ29 pRNA sequence that starts at ribonucleotide 23, preferably at ribonucleotide 20, and ends at ribonucleotide 95, preferably ribonucleotide 97, in the φ29 pRNA sequence (FIG. 2). In addition or in the alternative, the nucleotide sequence of the pRNA region of the pRNA chimera is preferably at least 60% identical to, more preferably 80% identical to, even more preferably 90% identical to, and most preferably 95% identical to the nucleotide sequence of a corresponding native SF5' pRNA (FIG. 3(a)), B103 pRNA (FIG. 3(b)), φ29/PZA pRNA (FIG. 3(c)), M2/NF pRNA (FIG. 3(d)), GA1 pRNA (FIG. 3(e)), or the aptRNA chimera (FIG. 3(f)), most preferably φ29 pRNA (particularly bases 20-97).

Percent identity is determined by aligning two polynucleotides to optimize the number of identical nucleotides along the lengths of their sequences; gaps in either or both sequences are permitted in making the alignment in order to optimize the number of shared nucleotides, although the nucleotides in each sequence must nonetheless remain in their proper order. For example, the two nucleotide sequences are readily compared using the Blastn program of the BLAST 2 search algorithm, as described by Tatusova et al. (*FEMS Microbiol Lett* 1999, 174:247-250). Preferably, the default values for all BLAST 2 search parameters are used, including reward for match=1, penalty for mismatch=−2, open gap penalty=5, extension gap penalty=2, gap x_dropoff=50, expect=10, wordsize=11, and filter on.

The covalent linkages between the biologically active moiety and the pRNA region can be direct or indirect but preferably are indirect. In an indirect linkage, the spacer region includes additional string(s) of ribonucleotides at one or both ends of the biologically active moiety. These ribonucleotide strings, if present, contain preferably at least about 3 ribonucleotides; and preferably contain at most about 300, more preferably at most about 30 ribonucleotides. Compositionally, the strings can contain any desired ribonucleotides, however it is preferably that ribonucleotide compositions are selected so as to prevent the ribonucleotide strings on either side of the biological moiety from base pairing with each other or with other parts of the pRNA chimera.

Exemplary biologically active moieties include, without limitation, DNA, RNA, DNA or RNA analogs, including a ribozyme, a siRNA, a RNA aptamer, or an antisense RNA, peptide nucleic acid (PNA), a peptide, a protein such as an antibody, a polysaccharide, a cofactor, or a combination thereof. Since siRNA is a double-stranded RNA, the effective siRNA moiety could include any sequence to replace the 5'/3' paired helical region. Preferably the biological activity of the biologically active moieties is an enzymatic activity or binding activity or both; for example, the biologically active moiety may function as or encode a ribozyme or other catalytic moiety.

The biologically active moiety is preferably a polynucleotide. It should be understood that the terms "nucleotide," "oligonucleotide," and "polynucleotide" as used herein encompass DNA, RNA, or combinations thereof, unless otherwise indicated. Further, the terms DNA and RNA should be understood to include not only naturally occurring nucleic acids, but also sequences containing nucleotide analogs or modified nucleotides, such as those that have been chemically or enzymatically modified, for example DNA phosphorothioates, RNA phosphorothioates, and 2'-O-methyl ribonucleotides. A preferred biologically active polynucleotide is a polyribonucleotide, more preferably the biologically active polynucleotide is a ribozyme such as a hammerhead ribozyme or a hairpin ribozyme. Antisense RNA and other bioactive RNAs are also preferred.

A ribozyme is generally characterized by:
arm 1-active enzyme center-arm 2 where arm 1 and arm 2 are sequences complementary to the target substrate to be cleaved by the ribozyme, and the active enzyme center is the catalytic center that cleaves the target RNA. The "arms" of the ribozyme typically contain at least about 7 nucleotides, preferably at least about 12 nucleotides; and typically contain at most about 100 nucleotides, preferably at most about 30 nucleotides. The nucleotide sequence of the arms can be engineered to hybridize to the nucleotide sequence of any desired target nucleic acid.

Advantageously, incorporating a biologically active polynucleotide, e.g., a ribozyme, into the pRNA chimera of the invention protects the ends of the ribozyme thereby rendering the it resistant to exonuclease degradation. Moreover, the secondary structure of pRNA is compact and very stable. A pRNA domain defined by nucleotides 30-91 of φ29 pRNA is especially stable.

The compactness and stability of pRNA allows the pRNA region and the ribozyme to fold independently. Proper folding of the inserted RNA is facilitated, thereby preserving its biological activity. The stable structure of the carrier pRNA region is retained as well. A major obstacle in designing molecules to deliver ribozymes, i.e., misfolding of the ribozyme and carrier region as a result of interactions between them, has thus been overcome by utilizing the very stable pRNA molecule as the carrier. That the activity of the ribozyme is retained in the circularly permuted pRNA chimera is especially significant because it means that the new 5' and 3' ends of the pRNA chimera can be positioned so as to "bury" them in the folded pRNA structure, thereby further protecting the pRNA chimera from degradation. These features suggest great promise for the use of the pRNA chimera of the invention as a ribozyme delivery vehicle in medical and veterinary applications.

As shown in the Examples below, circularly permuted pRNAs were constructed without impacting pRNA folding. In addition, connecting the pRNA 5'/3' ends with variable sequences did not disturb its folding and function. These unique features, which help prevent two common problems—exonuclease degradation and misfolding in the cell, make pRNA an ideal vector to carry therapeutic RNAs.

The pRNA chimera of the invention employs a "circular permutation" of a bacteriophage pRNA. A "circularly permuted" RNA molecule (cpRNA) is a linear RNA molecule in which the native 5' and 3' ends are covalently linked. The linkage can be direct, or it can be indirect by using a spacer region. Since a cpRNA molecule is linear, new normative 5' and 3' ends are created by forming an opening in the molecule (i.e., a discontinuity in the pRNA sequence) at a different location. The pRNA chimera of the invention is linear as a result of a normative opening in the bacteriophage pRNA framework at a designated site, which circularly permutes the bacteriophage framework and forms the actual 5' and 3' ends of the pRNA chimera. As already noted, the normative opening can be at any desired location in the pRNA region. Examples of selected locations in, for example in φ29 pRNA can be found in Zhang et al., *RNA* 3:315-323 (1997) and Zhang et al., *Virology* 207:442-451 (1995). See also Garver et al., *J. Biol. Chem.* 275:2817-2824 (2000); Chen et al., *J. Virology* 71:495-500 (1997); Trottier et al., *RNA* 6:1257-1266 (2000); and Zhang et al., *Virology* 281:281-293 (2001).

The pRNA chimera of the invention can be synthesized chemically or enzymatically using standard laboratory protocols. The pRNA region is preferably transcribed from a DNA template that encodes it, although if desired it can be synthesized chemically. If synthesized chemically, the pRNA region optionally contains normative nucleotides (e.g., derivatized or substituted nucleotides) and/or normative bonds analogous to the phosphodiester bonds that characterize naturally occurring nucleic acids.

Preferably the pRNA region is transcribed or synthesized as a single RNA molecule. In one embodiment of the method, the spacer region is chemically or enzymatically linked to the "native" ends of the pRNA region to form a circular chimeric molecule. The pRNA is then cleaved at a predetermined site to form the linear, circularly permuted pRNA chimera.

When the spacer region is RNA, another embodiment of the method includes transcribing the entire pRNA chimera from a single DNA template that encodes the entire chimeric molecule. In another embodiment of the method, the RNA spacer region is produced separately, either via transcription from its own template or by chemical synthesis, after which it is ligated to the pRNA region.

Also included in the invention is a DNA molecule that includes a nucleotide sequence that encodes the pRNA chimera of the invention. The spacer region of the encoded chimera is necessarily RNA in this aspect of the invention. The DNA molecule can be linear or circular. It can be double stranded or single stranded; if single stranded, its complement is included in the term "DNA molecule" as well. A DNA molecule for use in introducing a pRNA into a cell preferably contains regulatory elements such that the pRNA chimera is operably encoded. A pRNA chimera is "operably encoded" by a DNA molecule when the DNA molecule contains regulatory elements that allow the pRNA chimera to be produced by transcription of the DNA molecule inside the cell. Such regulatory elements include at least a promoter. Optionally, the DNA molecule includes additional regulatory motifs that promote transcription of the RNA chimera, such as, but not limited to, an enhancer. The DNA molecule can be introduced into the host cell using anionic or cationic lipid-mediated delivery or other standard transfection mechanisms including electroporation, adsorption, particle bombardment or microinjection, or through the use of a viral or retroviral vector.

It should be noted that the pRNA chimera can, if desired, be introduced into the host cell directly. For example, a product available under the trade designation TRANSMESSENGER TRANSFECTION REAGENT (available from Qiagen), which a lipid-based formulation that is used in conjunction with a specific RNA-condensing enhancer and an optimized buffer, can be used to transfect the pRNA chimera into eukaryotic cells.

Optionally, the DNA molecule can contain one or more features that allow it to integrate into the cell's genome. For example, it can be delivered in the form of a transposon, a retrotransposon, or an integrating vector; alternatively, it can contain sequences that are homologous to genomic sequences that allow it to integrate via homologous recombination. On the other hand, the DNA molecule can be designed to exist within a cell as nongenomic DNA, e.g., as a plasmid, cosmid, episome and the like.

Transcription from a DNA template encoding the entire chimeric RNA molecule can occur in vitro or within a cell. The cell can be in cell culture, or in an organism (in vivo) such as a plant or an animal, especially a human, or in a cell explanted from an organism (ex vivo).

Figure 6A:
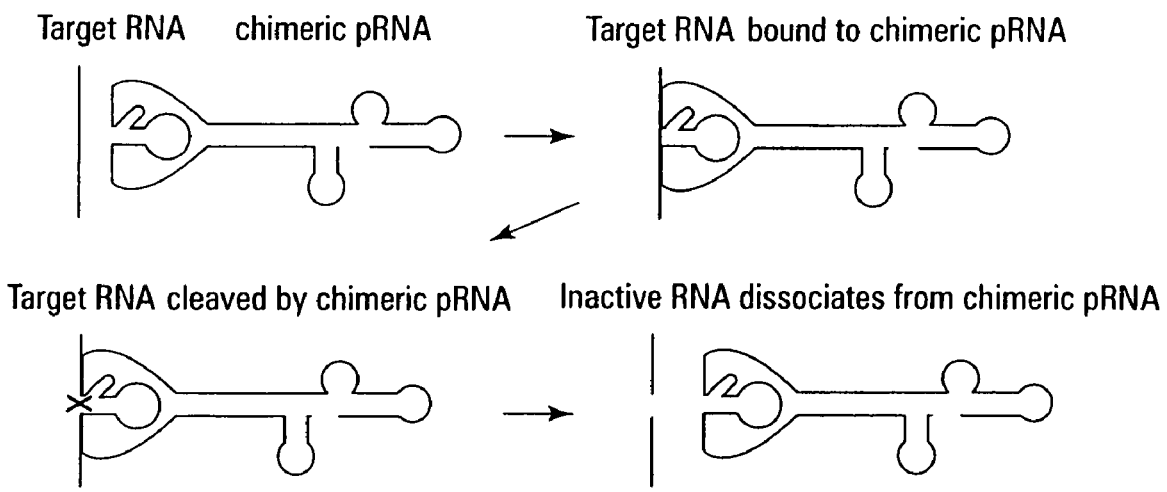
FIG. 6 depicts (a) a possible mechanism of pRNA-ribozyme cleavage activity; and (b) the structural arrangement of the chimeric pRNA/ribozyme complex.
Figure 6B:
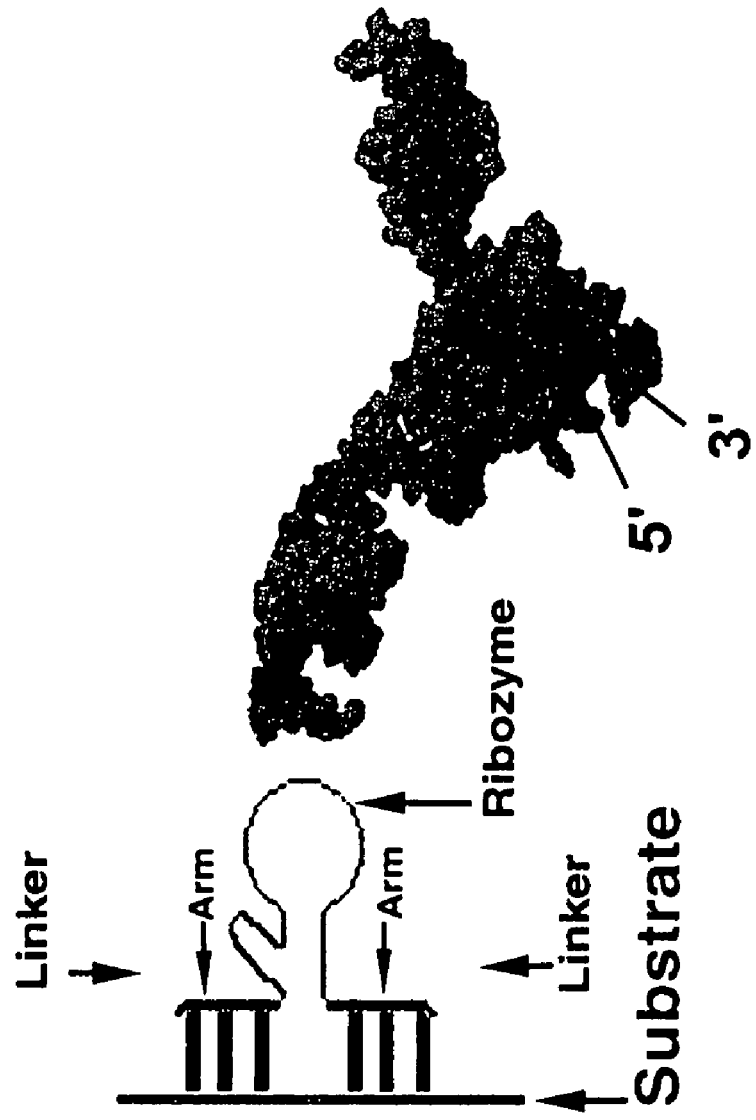
Figure 7A:
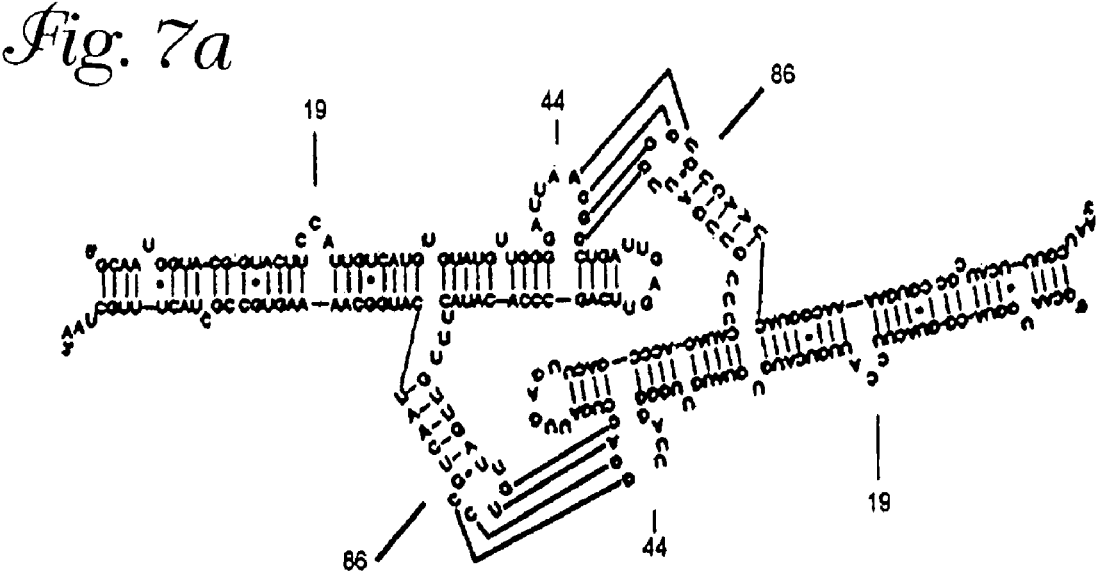
FIG. 7 depicts (a) the secondary structure of a pRNA dimer (SEQ ID NO:26) (Trottier et al., RNA 6:1257-66 (2000)) and (b) a three dimensional computer model of a pRNA dimer (Hoeprich and Guo, J Biol Chem 277:20794-803 (2002)). The lines between residues of the monomer subunits of the dimer in (a) show the bases of the left and right hand loops interact intermolecularly via hand-in-hand interaction (Guo et al., Mol Cell 2:149-55 (1998); Zhang et al., Mol Cell 2:141-47 (1998)).
Figure 7B:

Advantageously, the pRNA chimera of the invention can be used to deliver a biologically active RNA molecule to a target within a cell. A DNA molecule having nucleotide sequence that operably encodes a circularly permuted pRNA region and a spacer region is introduced into a cell. The spacer region includes a biologically active RNA, and transcription of the DNA to yields the biologically active RNA. The biologically active molecule thus delivered is preferably a ribozyme, and the target is preferably viral or mRNA associated with a gene whose expression it is desirable to reduce. FIG. 6(a) shows a proposed mechanism for cleavage of a target RNA by a pRNA ribozyme chimera. The ribozyme targeting the HBV polyA signal is connected to the native 5'/3' ends of the phi29 pRNA (FIG. 6(b)). An antisense RNA, which can target intracellular DNA or RNA, is also preferred as the biologically active molecule.

φ29 pRNA has a strong drive to form dimers (FIG. 7), and dimers are the building blocks of hexamers (Hoeprich and Guo, *J Biol Chem* 277:20794-20803 (2001); Mat-Arip et al., *J Biol Chem* 276:32575-32584 (2001); Trottier et al., *RNA* 6:1257-1266 (2000); Chen et al., *RNA* 5:805-818 (1999); Guo et al., *Mol Cell* 2:149-155 (1998); Zhang et al., *Mol Cell* 2:141-147 (1998); Hendrix, Cell 94:147-150 (1998)). The formation of monomers or dimers can be controlled by manipulating and controlling the sequences of the two interacting loops (Hoeprich and Guo., *J Biol Chem* 277:20794-20803 (2001); Mat-Arip et al., *J Biol Chem* 276:32575-32584 (2001); Trottier et al., *RNA* 6:1257-1266 (2000)); Chen et al., *RNA* 5:805-818 (1999); and Zhang et al., *Mol Cell* 2:141-147 (1998)). The formation of pRNA dimers (FIG. 7) might also assist in stabilizing pRNA/ribozyme chimera molecules. As long as the openings of the circularly permutated pRNAs are close to an area of dimer formation, the tertiary structure can help prevent exonucleases from accessing the ends of the RNA molecules.

Figure 8:
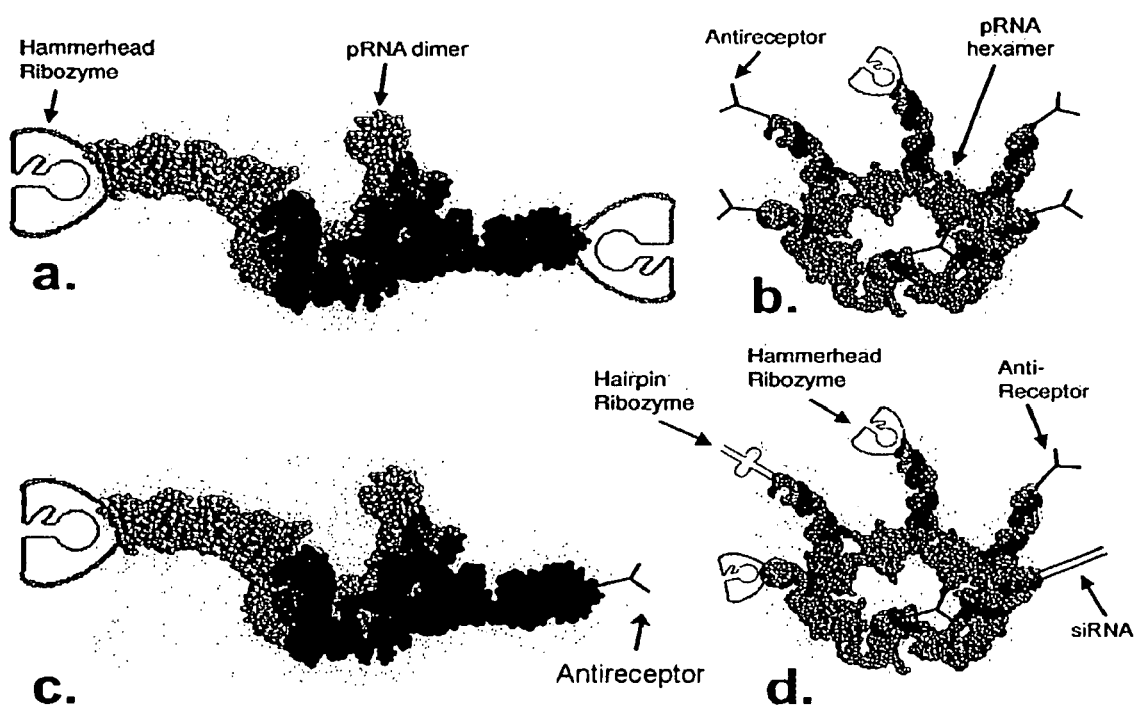
FIG. 8 (a-d) represent potential uses of the phi29 pRNA as polyvalent vector system for delivery of drugs and other bioactive agents, and therapy.

Importantly, formation of a dimer or a hexamer also facilitates the ability of the chimeric molecule to carry multiple therapeutic agents. A complex of two or more circularly permuted pRNA is termed herein a polyvalent multimeric pRNA. A dimeric complex will contain two spacer regions and hence two biologically active moieties. For example, one of the pRNA subunits of a hexamer could carry the hammerhead ribozyme, and the other pRNA subunit could carry a hairpin ribozyme or an antisense RNA (FIG. 8). Applications of multiple therapeutic agents might enhance the efficiency of the in vivo therapy.

The polyvalent multimeric pRNA could also be used to specifically target and deliver the therapeutic agent, such as a ribozyme. For example, one of the subunits can be used to carry an RNA aptamer or other molecule (such as an antibody) that interacts with a cell-surface receptor or other component of the cell membrane or cell wall. Binding of the dimer or hexamer pRNA to a specific receptor would, for example, enable the specific delivery of the pRNA complex to the cell via endocytosis.

Specific receptor-binding RNA molecules can, for example, be identified and isolated through SELEX (Systematic Evolution of Ligands by Exponential Enrichment) (Tuerk et al., *Science* 249:505-510 (1990); and Ellington et al., *Nature* 346:818-822 (1990)). Starting with a library containing random RNA sequences, in vitro evolution techniques allow for the selection of the RNA molecules that are able to bind a specific pre-identified substrate, such as a ligand or receptor (Ciesiolka et al., *RNA* 1:538-550 (1995); Klug and Famulok, *Molecular Biology Reports* 20:97-107 (1994). Receptor-binding ("anti-receptor") RNA can be inserted into the pRNA vector to form circularly permuted pRNA as described herein. The chimeric RNA carrying the hammerhead ribozyme and the chimeric RNA carrying the anti-receptor could be mixed to form dimers or higher order structures via inter-RNA loop/loop interaction as reported previously (Chen et al., *J Biol Chem* 275:17510-17516 (2000); Guo et al., *Mol Cell* 2:149-155 (1998); Zhang et al., *Mol Cell* 2:141-147 (1998); and Hendrix, *Cell* 94:147-150 (1998)).

In addition, the basic principles of the SELEX method can be employed to create RNA aptamers using the basic pRNA chimera design of the invention. RNA molecules useful for the identification of RNA aptamers that bind a pre-identified substrate contain a random sequence, preferably 25-100 bases, present at one end of the pRNA of the present invention, preferably connected where the native 5'/3' ends are. Optionally, linker sequences connecting the random sequence connected to both ends to the 5'/3' ends can be included. Such RNA molecules may be made by chemical or enzymatic synthesis. For instance, RNA molecules useful for the identification of RNA aptamers can be made using three primers; a template primer, a 3' end primer, and a 5' end primer (see FIG. 9). The DNA primers are designed and defined with reference to a pRNA sequence or its derivatives and counterparts. The template primer includes the random sequence flanked by two nucleotide sequences that bind the 3' and 5' end primers. Preferably, the flanking sequences represent the DNA equivalent of the native 5' and 3' ends of the wild-type pRNA. Preferably, each flanking sequence of the DNA template contains a nucleotide sequence having at least 14 bases that are complimentary to the sequences of primer one and two corresponding to the 5' and 3' ends of the pRNA.

Figure 9:
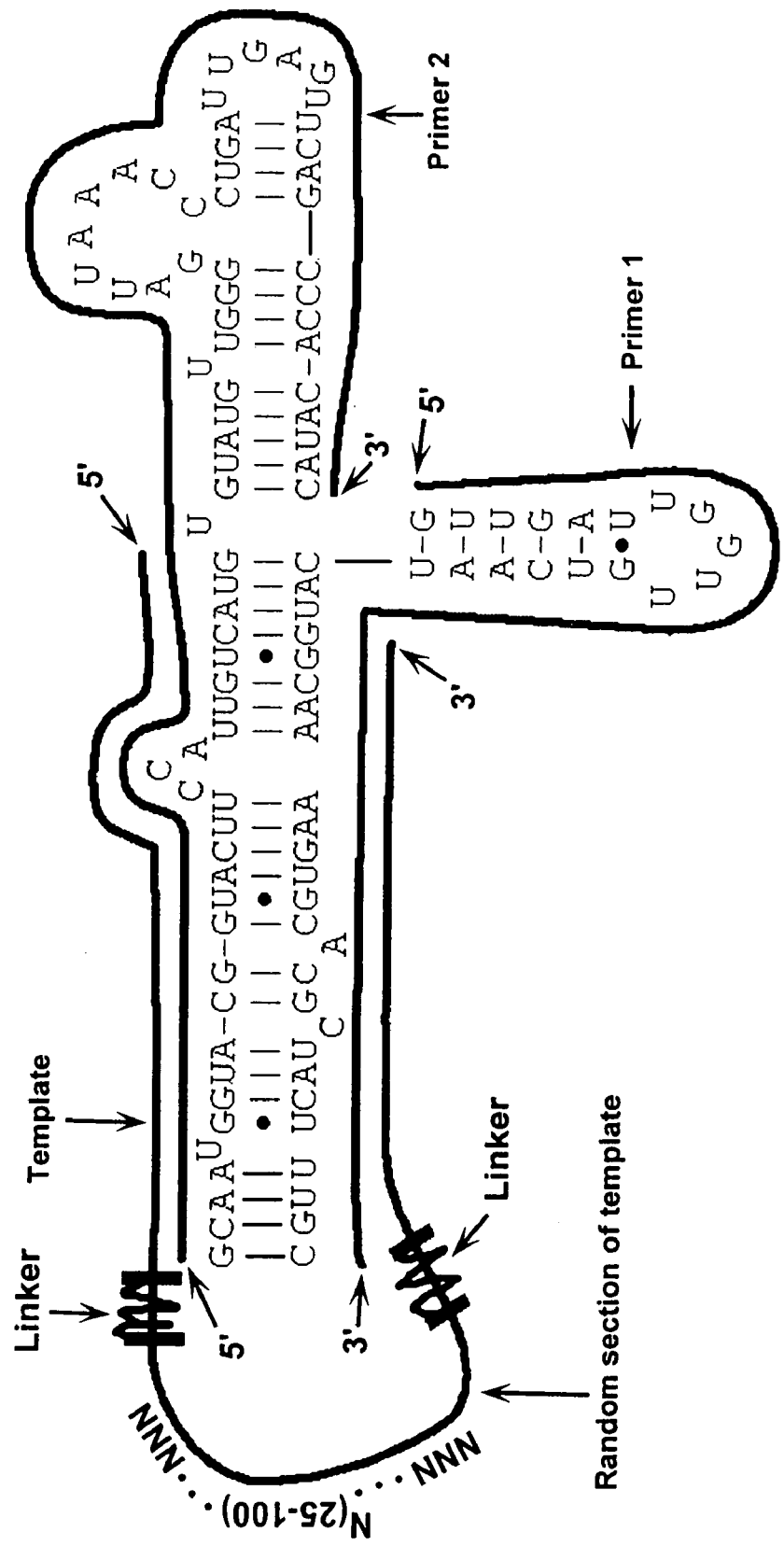
FIG. 9 depicts the use of circularly permuted pRNA (SEQ ID NO:28) in the SELEX method to identify RNA aptamers that bind to a pre-identified substrate. NNN ... N(25-100) ... NNN, random sequence of template; template, template primer; primer 1, 3' end primer; primer 2, 5' end primer.

The 3' and 5' end primers can be used to make by PCR the RNA molecules useful for the identification of RNA aptamers, and also for amplification in the SELEX method. The 3' end primer contains nucleotides that are complementary to an RNA sequence to make a 5' end of a wild-type pRNA sequence, beginning at or about at a wild-type 5' end and ending at any nascent 3'-end, e.g., base 71. Likewise, the 5, end primer contains the nucleotides that are complementary to an RNA sequence at the 3' end of a wild-type pRNA sequence, beginning at or about at a wild-type 3' end (around base 117) and ending at any nascent 5'-end, e.g., base 75 (FIG. 9). Taken together, the 5' and 3' end primers contain nucleotide sequences complementary to all or most of the wild-type pRNA sequence, such that after transcription the resultant RNA aptamer structure is that of a pRNA chimera of the invention. For example, if the 3' end primer terminates at base 71 of the wild-type pRNA, and the 5' end primer terminates at base 75 of the wild-type pRNA, only pRNA bases 72-74 will be missing from the pRNA chimera produced in the SELEX process and this will not affect the independent folding of the pRNA. The secondary structure of the resultant pRNA chimera is equivalent to the phi29 pRNA structure (see FIG. 3 for examples of equivalent structures). For example, the sequence of the 5'/3' helical region of the pRNA can vary, as long as it forms a paired double stranded region.

The RNA aptamer molecule resulting from this system, which binds the pre-identified substrate, will contain a newly selected RNA sequence connected to the original 5' and 3' end of the cp-pRNA, and will be ready for use in a variety of applications without further modification. Such RNA aptamer containing pRNA moiety will be able to bind a pre-identified substrate in variety of applications, including, but not limiting to, drug or gene delivery, and construction of nanodevices.

The phylogenetic analysis of pRNAs from *Bacillus subtilis* phages SF5, B103, phi29, PZA, M2, NF, and GA1 shown in FIG. 3 shows very low sequence identity and few conserved bases, yet the family of pRNAs appears to have similar predicted secondary structures (Pecenkova et al., *Gene* 199:157-163 (1997); Chen et al., *RNA* 5:805-818 (1999); Bailey et al., *J Biol Chem* 265:22365-22370 (1990)). All seven pRNAs of these phages contain both the right and left hand loops, which form a loop/loop interaction via W.C. base pairing. Complementary sequences within the two loops are found in each of these pRNAs. Therefore, these pRNAs could also be used as vector to carry small therapeutic RNA molecules (FIG. 3).

The results from these ribozyme-mediated suppression experiments could be applied to other cell types, including those of many plant and animal species. Transgenic plants and animals could then be developed for a variety of purposes, if the chimeric ribozyme-pRNA is incorporated into the genome of cells, animals or plants.

Surprisingly, conjugation of a ribozyme to a bifurcated pRNA region such that both ends of the ribozyme are covalently linked to the pRNA region does not render the ribozyme inactive, nor does it appear to interfere with the independent folding of the pRNA region or the ribozyme region. Because tethering of both ends of the ribozyme RNA is expected to also prevent degradation by exonuclease, the resulting pRNA-ribozyme chimera is expected to be useful to cleave undesired RNAs in plants and animals, including humans. Additionally, transgenic plants and animals with resistance to diseases can be developed by introducing DNA encoding the pRNA-ribozyme chimera into the genomic DNA of the cell.

The pRNA chimera of the invention is also useful in vitro, for example, for the characterization of RNA molecules. RNA molecules, particularly small RNA molecules, can be stabilized or "chaperoned" by inclusion in the spacer region of a pRNA chimera of the invention, which insures that they remain properly folded, active and exposed. For example, pRNA chimera containing an RNA of interest can be immobilized, covalently or noncovalently, on a substrate, such that the RNA of interest is presented. The immobilized pRNA chimera can then be contacted with test molecules, such as cellular extracts or components, to identify the constituents to which the RNA of interest binds or otherwise interacts. This is preferable to immobilizing the RNA of interest directly on the substrate, because direct immobilization can interfere with the folding of the RNA of interest and also block portions of the structure from contact with the test molecules. The pRNA chimera can also be used to stabilize RNAs in solution for use in binding assays, cleavage assays, diagnostics and the like.

EXAMPLES

The present invention is illustrated by the following examples. It is to be understood that the particular examples, materials, amounts, and procedures are to be interpreted broadly in accordance with the scope and spirit of the invention as set forth herein.

Example 1

Elongation of phi29 pRNA at the 3' End and Effect on Activity

To investigate whether additional burdens can be imposed on the pRNA, the 3' ends of the pRNA were extended with variable lengths.

The RNA products Eco-pRNA and XbHi-pRNA were produced by in vitro T7 RNA polymerase transcription using DNA templates from plasmid pCRTMII that were precleaved with EcoRI or XbaI/HindIII, respectively. To generate the plasmid pCRTM2, a PCR DNA fragment was produced with the primer pair P7/P11 to flank the pRNA coding sequence (Zhang et al., *Virology* 207:442-51 (1995)). The PCR fragment was then cloned into the PCR cloning vector pCRTMII (Invitrogen, Carlsbad, Calif.). DNA sequencing after colony isolation confirmed the presence of the PCR fragment in the plasmid. The RNA product 174-pRNA was either extracted from procapsids, as described by Guo et al. (*Science* 236:690-94 (1987)) and Wichitwechkarn et al. (*Nucl. Acids Res.* 17:3459-68 (1989)) or transcribed in vitro with a PCR DNA fragment generated using the plasmid pC13-12A(RNA) as template, following the method described in Wichitwechkarn et al. (*Mol Biol* 223:991-98 (1992)). The RNA product Di-RNA with a 120-base extension from the 3'-end of pRNA was transcribed in vitro with a PCR DNA fragment using cpD-NAT7, as described by Zhang et al. (*Virology* 207:442-51 (1995)) as template for a PCR reaction.

It was found that at least 120 bases could be added to the 3' end of the pRNA without significant interference of pRNA function (FIG. 10). Such additions included end labeling of pRNA with biotin, pCp, DIG and phosphate. Variable lengths of sequences added to the 3' end of pRNA had undetectable or minimal impact on viral activity. These results indicated that the 117-base pRNA folded independent of bases extended from its 3'-end.

Example 2

Circularly Permuted φ29 pRNA

Circularly permuted pRNA (cpRNA) from bacteriophage φ29 was synthesized by way of transcription from a DNA template. The feasibility of constructing circularly permuted RNAs lies in the close proximity of the native φ29 RNA 5' and 3' ends (Zhang et al., *Virology* 201:77-85 (1994)). φ29 pRNA 5' and 3' ends are in close proximity. Construction of biologically active circularly permuted pRNAs revealed that interruption of pRNA internal bases did not affect the global folding of pRNA.

To construct circularly permuted pRNA, two tandem pRNA-coding sequences separated by a 3-base or 17-base loop sequence were cloned into a plasmid (FIG. 11) (see, Zhang et al., *Virology* 207:442-451 (1995). Plasmids cpDNA3A (I) and cpDNAT7 (II) containing a tandem pRNA coding sequence were connected by 3- or 17-nucleotide synthetic loops, respectively. PCR was used to create dsDNA fragments with non-native 5'/3' ends. In vitro transcription was then performed to generate pRNAs with new 5'/3' ends. PCR primer pairs, such as P6/P5, complementary to various locations within pRNA coding sequences, were designed to synthesize PCR fragments for the transcription of cp-pRNAs. The PCR DNA fragments were directly used as templates for in vitro transcription with $SP_6$ RNA polymerase. The resulting linear cpRNA transcript linked the native 5'-end of pRNA with its 3' end by way of small loop: AAA in the case of DNA template cpDNA3A and UAAUACGACUCAGUAUA (SEQ ID NO:8) in the case of DNA template $cpDNAT_7$.

FIG. 11 shows generalized circularly permuted pRNA structure (SEQ ID NO:2) with arrows indicating various new openings (Zhang et al., *RNA* 3:315-323 (1997)). Wild-type sequences of 5'U1C2 and 3'A117G116 could be changed to G1G2 and C116C117, respectively, relative to wild-type pRNA to facilitate and enhance transcription by T7 RNA polymerase.

To our surprise we found that insertion of sequences to link the native 5' and 3' ends of the pRNA molecule and relocation of the 5' and 3' ends somewhere else on the molecule does not interfere with the pRNA activity, since the cpRNA was still able to catalyze φ29 assembly. Therefore, most of the internal bases could be used as new termini for constructing active cp-pRNA (Zhang et al., *Virology* 207:442-451 (1995); Zhang et al., *RNA* 3:315-322 (1997)).

Since linking the 3' and 5' ends of the pRNA with nucleotide sequences of variable lengths did not affect the pRNA activity, this is an indication that pRNA and the linking sequence fold independently. These findings imply that a ribozyme could be placed between the 3' and 5' ends of the PRNA could be able to fold without being influenced by the sequence and folding of pRNA.

Example 3

In Vitro Activity of pRNA-Ribozyme Chimera

The loop used to connect the native termini of the pRNA in Example 2 did not itself possess any biological activity. However, we wondered whether an RNA sequence with biological activity would retain its activity if tethered at both ends to pRNA. It was decided to test a hammerhead ribozyme as the loop sequence.

Figure 12:
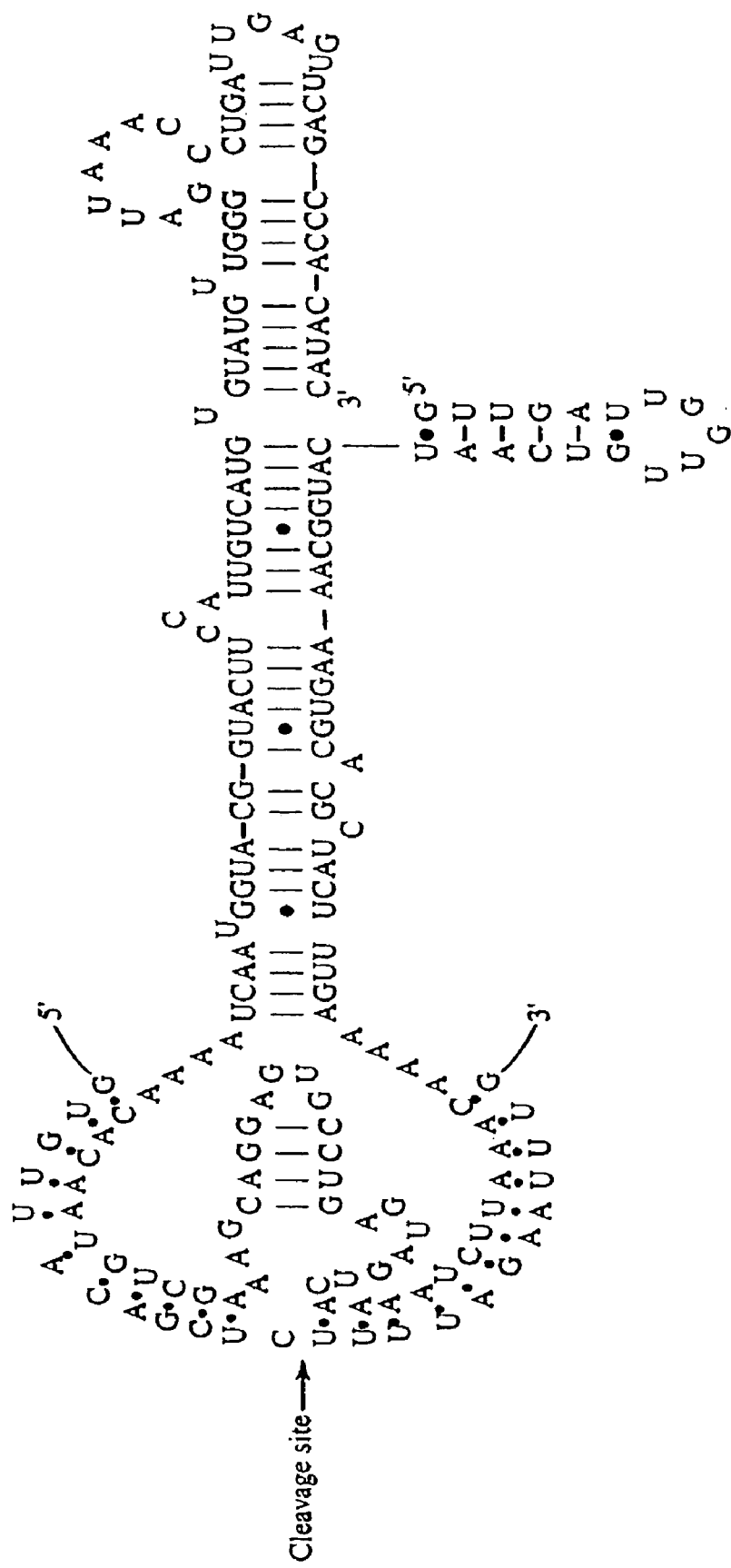
FIG. 12 depicts an RNA chimera (SEQ ID NO:3) bound to a portion of the U7snRNA substrate (SEQ ID NO:4).

An in vitro model system (FIG. 12) as previously described in Cotton et al. (*EMBO J.* 8:3861-3866 (1989)) was modified and used as a control to test the functionality of a pRNA-ribozyme chimera. U7snRNA (SEQ ID NO:4) was selected as the target RNA. A chimeric RNA molecule, pRNA-RzU7 (SEQ ID NO:3), was synthesized. This system was used to determine whether the pRNA could harbor other hammerhead ribozymes to function in substrate cleavage (Cotten and Birnstiel, *EMBO J* 8:3861-3866 (1989)).

RNAs were prepared as described previously by Zhang et al. (*Virology* 201:77-85 (1994)). Briefly, DNA oligonucleotides were synthesized with the desired sequences and used to produce double-stranded DNA by PCR. The DNA products containing the T7 promoter were cloned into plasmids or used as substrate for direct in vitro transcription. The antisense DNA encoding the U7 substrate and the DNA encoding ribozyme RzU7 were mixed with the T7 sense promoter prior to transcription. The dsDNA encoding ribozyme RzU7-pRNA and T7 promoter were made by PCR. RNA was synthesized with T7 RNA polymerase by run-off transcription and purified from polyacrylamide gels. Sequences of the plasmids and PCR products were confirmed by DNA sequencing.

Figure 13A:
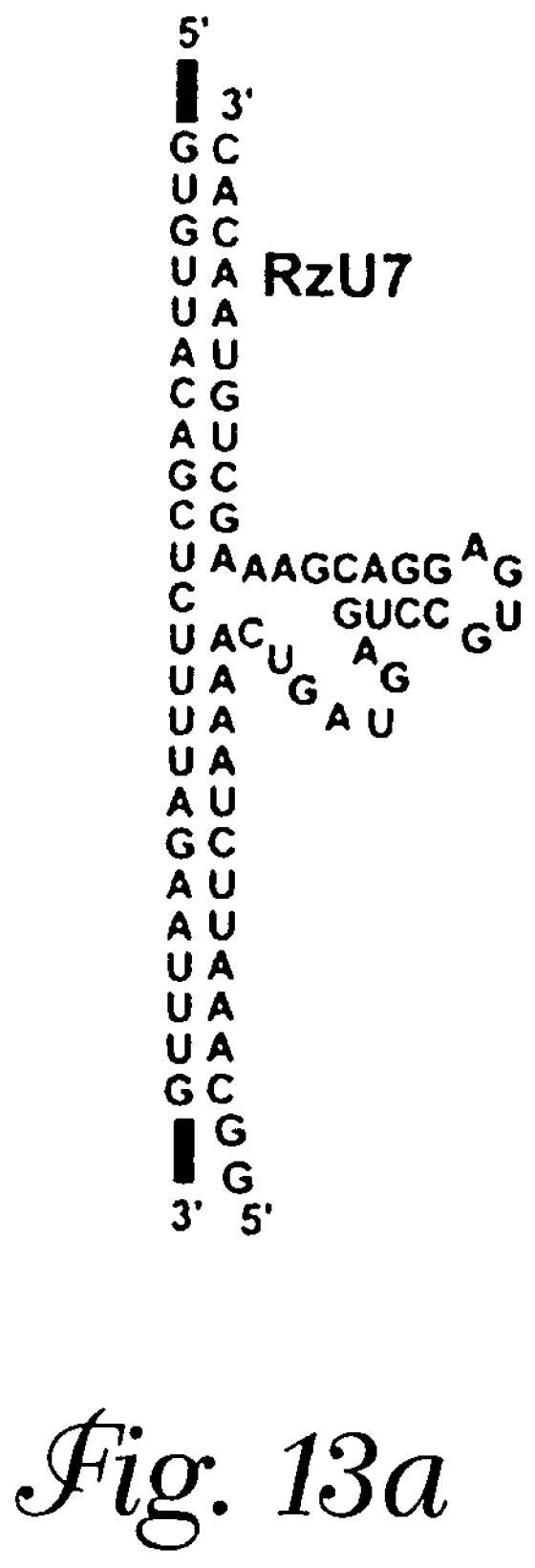

The relative abilities of the U7-targeting ribozyme (47 bases), RzU7, and the U7-targeting pRNA-ribozyme (168 bases), RzU7-pRNA, to cleave an U7snRNA fragment were compared. The ribozyme cleavage reaction was done as a control experiment to demonstrate that ribozyme reactions work correctly without any modifications. The results reveal that the RzU7-pRNA ribozyme was able to cleave the substrate with results comparable to the control RzU7 ribozyme (FIG. 13). Extended investigation revealed that specific hammerhead ribozymes harbored by pRNA, were able to cleave other respective substrates.

The RNAs used in these experiments were generated by T7 polymerase in vitro transcription either using PCR or by cloning into a plasmid. The transcription products are as follows:

T7 transcription of pRNA-RzU7 yields the 168mer:

5'GUUGAUUGGUUGUCAAUCAUGGCAAAAGUGCACGCUACUUUGAAAAAC

AAAUUCUAAAACUGAUGAGUCCGUGAGGACGAAAGCUGUAACACAAAAUGC

AAUGGUACGGUACUUCCAUUGUCAUGUGUAUGUUGGGAUUAAACCCUGAU

UGAGUUCAGCCCACAUACA3'.
(SEQ ID NO:3 with additional A at 3' end)

T7 transcription of U7 template yields the 94mer:

5'GGGAAAGCUUAUAGUGUUACAGCUCUUUUAGAAUUUGUCUAGCAGGUUU

UCUGACUUCGGUCGGAAAACGCCUAACGUUGCAUGCCUGCAGGUC3'
(SEQ ID NO:9)

T7 transcription of RzU7 template yields the 47mer:

5'GGCAAAUUCUAAAACUGAUGAGUCCGUGAGGACGAAAGCUGUAACA

C3'.(SEQ ID NO:10)

The abilities of RzU7 (47 bases) (SEQ ID NO: 10) and pRNA-RzU7 (168 bases) (SEQ ID NO:3) to cleave U7snRNA (SEQ ID NO:9) were compared. The RzU7 cleavage reaction was done as a control experiment to demonstrate that ribozyme reactions work correctly without any modifications. The cleavage reaction using pRNA-RzU7 was done to confirm that pRNA could be successfully used as a carrier molecule for ribozymes.

The U7-targeting ribozyme RzU7 and the ribozyme RzU7-pRNA cleavage reactions were performed at 37° C. for 90 minutes in the presence of 20 mM Tris pH 7.5, 20 mM MgCl$_2$, and 150 mM NaCl. Control reactions were performed by substituting water for RNAs. The samples were dialyzed against TE (10 mM Tris, 1 mM EDTA, pH 8.0) for 30 minutes on a Millipore 0.025 μm VS type membrane. 2× loading buffer (8 M urea, TBE, 0.08% bromophenol blue, 0.08% xylene cyanol) was added to the samples prior to loading them on a 15% PAGE/8M urea denaturing gel in TBE (0.09 M Tris-borate, 0.002 M EDTA). The gel was stained with ethidium bromide and visualized using EAGLE EYE II (Stratagene).

Figure 13B:
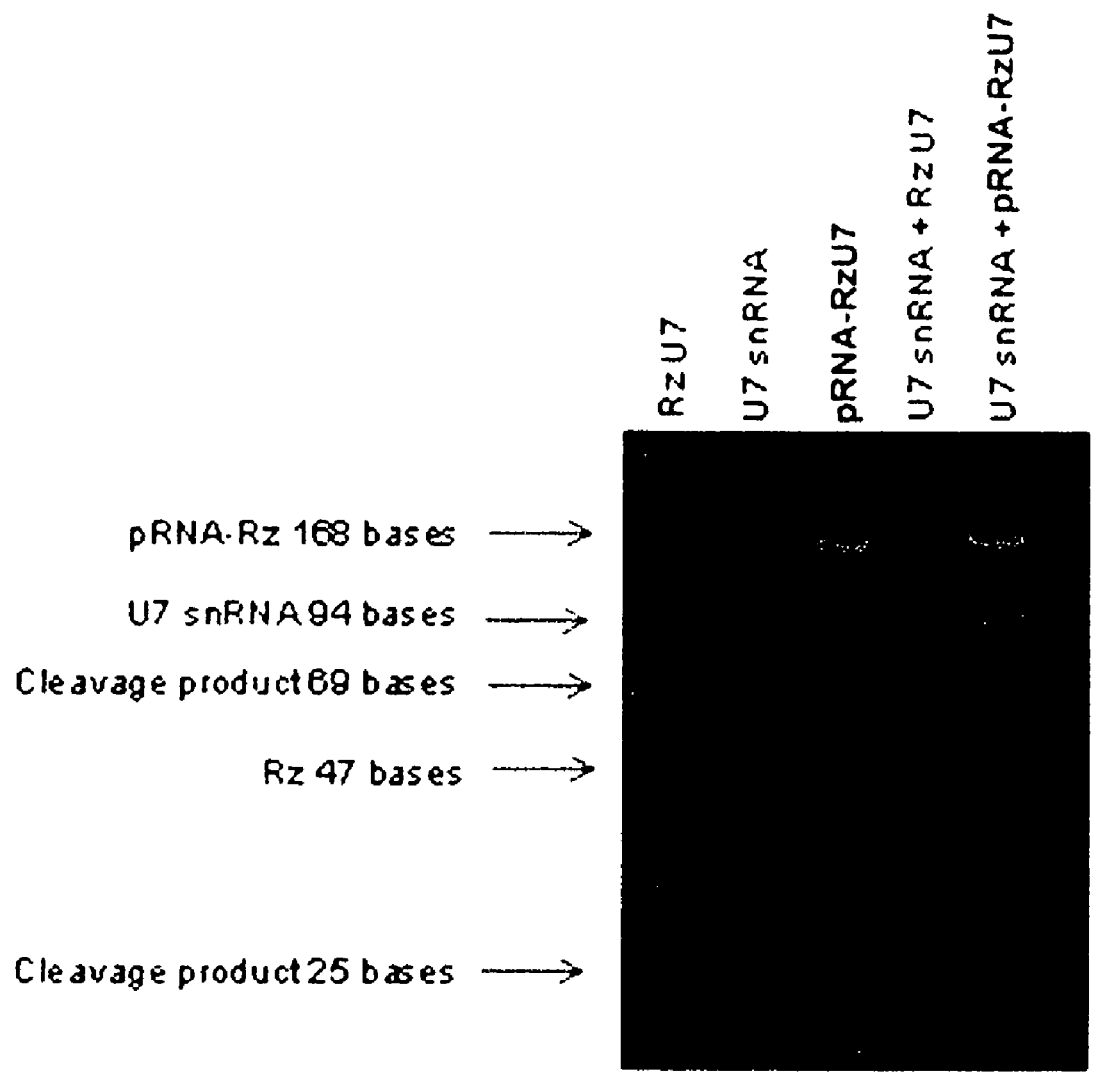
FIG. 13 depicts in vitro cleavage of substrates by chimeric ribozyme carried by pRNA. (a) Schematic showing secondary structure of RzU7, the U7 snRNA targeting ribozyme (SEQ ID NO: 10), base-pairing with its substrate (SEQ ID NO:4). (b) Denaturing urea gel showing cleavage of the substrate U7snRNA into its expected 69mer and 25mer cleavage products by both the ribozyme RzU7 and the chimera ribozyme PRNA-RzU7.

FIG. 13(b) shows the successful results of the cleavage reaction. The predicted 69mer and 25mer cleavage products can be seen.

This experiment confirmed successfully using pRNA as a carrier molecule for ribozymes. The finding that the hammerhead ribozyme retains activity in the pRNA-RzU7 construct has important implications. Independent folding of pRNA apparently and advantageously allows the ribozyme to fold into the correct structure and perform its function in cleaving target RNA. Furthermore, since both ends of the ribozyme are connected to pRNA, the linkage is expected to protect the ribozyme from exonuclease digestion in the cell. Thus, the ribozyme will be stable after expression in the transgenic plants or animals, solving a persistent problem that has stood in the way of therapeutic use of ribozymes.

Example 4

In Vitro Activity of pRNA-Ribozyme Chimera Against Hepatitis B Virus

Hepatitis is a serious disease that is prevalent in many countries worldwide. Hepatitis B virus (HBV) is one causative agent of this disease. HBV is an RNA virus. The RNA genome of HBV was used as target to test the functionality of a chimera pRNA-ribozyme. This work is important because it provides potential for the treatment of this serious infectious disease.

A pRNA-based vector based on bacteriophage φ29 was designed to carry hammerhead ribozymes that cleave the hepatitis B virus (HBV) polyA signal. This hammerhead ribozyme designed by Feng et al. (*Biol. Chem.* 382:655-660

(2001)) cleaves a 137-nucleotide HBV-polyA substrate into two fragments of 70 and 67 nucleotides.

We tested two versions of this ribozyme: pRNA-RzA, which contained a pRNA moiety, and RzA, which did not. The in vitro plasmid pRNA-RzA encoding the chimera ribozyme was constructed by using restriction enzymes XbaI and KpnI to remove the sequence encoding the unmodified ribozyme from the plasmid pRzA, which encoded the ribozyme targeting the HBV polyA signal (Feng et al., *Biol Chem* 382:655-60 (2001)). Then, a dsDNA fragment made by PCR that encoded the 188 nucleotide chimeric ribozyme was ligated into plasmid pRzA that had been double-digested with Xba I and Kpn I (FIG. 15). The HBV-targeting ribozyme was connected to the 5' and 3' ends of pRNA, and the pRNA was reorganized into a circularly permuted form. Two cis-cleaving ribozymes were added to flank the pRNA and HBV-targeting ribozyme.

RNAs were prepared as described previously by Zhang et al. (*Virology* 201:77-85 (1994)). Briefly, DNA oligonucleotides were synthesized with the desired sequences and used to produce double-stranded DNA by PCR. The DNA products containing the T7 promoter were cloned into plasmids or used as substrate for direct in vitro transcription. The in vitro plasmid pTZS encoding the HBV polyA (Feng et al., *Biol Chem* 382:655-660(2001)) substrate was linearized with BglII. The in vitro plasmids encoding the HBV polyA substrate targeting ribozyme RzA and the pRNA chimera ribozyme pRNA-RzA were linearized with EcoRI. RNA was produced by in vitro transcription with T7 polymerase using a linear DNA as a template for run-off transcripts. Sequences of the plasmids and PCR products were confirmed by DNA sequencing.

The product of the cis-cleaved transcript, ribozyme pRNA-RzA, was the 188mer:

5'GCUAGUUCUAGAGUUGAUUGGUUGUCAAUCAUGGCAAAAGUGCACGCUA

CUUUGCAAAACAAAUUCUUUACUGAUGAGUCCGUGAGGACGAAACGGGUCA

AAAGCAAUGGUACGGUACUUCCAUUGUCAUGUGUAUGUUGGGGAUUAAACC

CUGAUUGAGUUCAGCCCACAUACGGUACCUCGACGUC3'
(SEQ ID NO:17)

The transcribed ribozyme, RzA, is the 66mer:

5'GCUAGUUCUAGACAAAUUCUUUACUGAUGAGUCCGUGAGGACGAAACG

GGUCGGUACCUCGACGUC3' (SEQ ID NO:18)

The entire cassette of the in vitro plasmid was under the control of a T7 promoter. During transcription of the cassette, the transcript self-cleaved to produce a chimeric ribozyme (pRNA-RzA) containing the HBV-targeting ribozyme that was connected to the pRNA (FIG. 15).

The cleavage reaction was performed at 37° C. for 60 minutes in the presence of 20 mM Tris pH 7.5, and 20 mM $MgCl_2$. pRNA-RzA (0.539 nmol) was used to cleave HBV-polyA-(0.117 nmol). Control reactions were performed by substituting water for certain RNA. The RNA for which water was substituted was omitted from the name of the control. For example, the pRNA-RzA control has no HBV-polyA. The samples were dialyzed against TE (10 mM Tris, 1 mM EDTA, pH 8.0) for 30 minutes on a Millipore 0.025 μm VS type membrane. 2× loading buffer (8 M urea, TBE, 0.08% bromophenol blue, 0.08% xylene cyanol) was added to the samples prior to loading them on a 15% PAGE/8 M urea denaturing gel in TBE (0.09 M Tris-borate, 0.002 M EDTA). The gel was run at 100 volts until the xylene cyanol was 1.5 cm from the bottom of the gel. The gel was stained with ethidium bromide and visualized using EAGLE EYE II by Stratagene.

A dsDNA fragment encoding the pRNA chimera, pRNA-RzA (Table 1), was made by PCR. The pRNA-RzA ribozyme and the HBV-polyA substrate RNA were generated by in vitro transcription with T7 polymerase, using linear DNA as a template for run-off transcripts. This pRNA-RzA ribozyme transcription product then underwent two cis-cleavage reactions to free itself from extraneous RNA flanking sequences. "Cis-cleavage" means a cleavage reaction where both the ribozyme and the substrate are part of the same molecule. These two cis-cleavages were achieved by two ribozymes that flanked the chimera sequence. One cis-ribozyme (63 nt) was 5' to the chimera, while the other cis-ribozyme (46 nt) was 3' to the chimera (FIG. 15)). The cis-cleavage reactions predominantly occurred during the time the pRNA-RzA ribozyme was transcribed (FIG. 15).

TABLE 1

Plasmids, oligos and PCR products used for the assay of ribozyme activities

| Name | Function | Promoter | Target or Purpose | Contains pRNA |
|---|---|---|---|---|
| cpDNA3A (plasmid) | Circularly permutated pRNA, in vitro | $SP_6$ | Production of cpRNA | Yes |
| cpDNAT$_7$ (plasmid) | Circularly permutated pRNA, in vitro | $SP_6$ | Construction of chimeric ribozme | Yes |

TABLE 1-continued

Plasmids, oligos and PCR products used for the assay of ribozyme activities

| Name | Function | Promoter | Target or Purpose | Contains pRNA |
|---|---|---|---|---|
| pRNA-RzA (plasmid) | Ribozyme, in vitro | $T_7$ | HBV polyA | Yes |
| pRzA (plasmid) | Ribozyme, in vitro | $T_7$ | HBV polyA | No |
| pTZS (plasmid) | Substrate, in vitro | $T_7$ | HBV polyA | No |
| pRNA-CRzA (plasmid) | Ribozyme, tissue culture | CMV | HBV polyA | Yes |
| pCRzA (plasmid) | Ribozyme, tissue culture | CMV | HBV polyA | No |
| pCdRzA (plasmid) | Disabled ribozyme, tissue culture | CMV | HBV polyA | No |
| p3.6II (plasmid) | HBV genomic RNAs, tissue culture |  | HBV polyA | No |

TABLE 1-continued

Plasmids, oligos and PCR products used for the assay of ribozyme activities

| Name | Function | Promoter | Target or Purpose | Contains pRNA |
|---|---|---|---|---|
| U7 (oligos) | Substrate, in vitro | $T_7$ | U7 | No |
| RzU7 (oligos) | Ribozyme, in vitro | $T_7$ | U7 | No |
| PRNA-RzU7 (PCR) | Ribozyme, in vitro | $T_7$ | U7 | Yes |
| 12-LOX (oligos) | Substrate, in vitro | $T_7$ | 12-LOX | No |
| Rz12lox (oligos) | Ribozyme, in vitro | $T_7$ | 12-LOX | No |
| PRNA-Rz12lox (PCR) | Ribozyme, in vitro | $T_7$ | 12-LOX | Yes |

The processed product of the cis-cleaved transcript, a 188mer, was a major band in the gel and was purified. Examination of the gels used to purify pRNA-RzA ribozyme under UV light produced three distinct shadows. The slowly migrating band was the pRNA-RzA ribozyme. The other two bands that migrated much more quickly were the 5' and 3'-cis cleaving ribozymes. This indicates that the cis-cleavage is complete.

Figure 14:
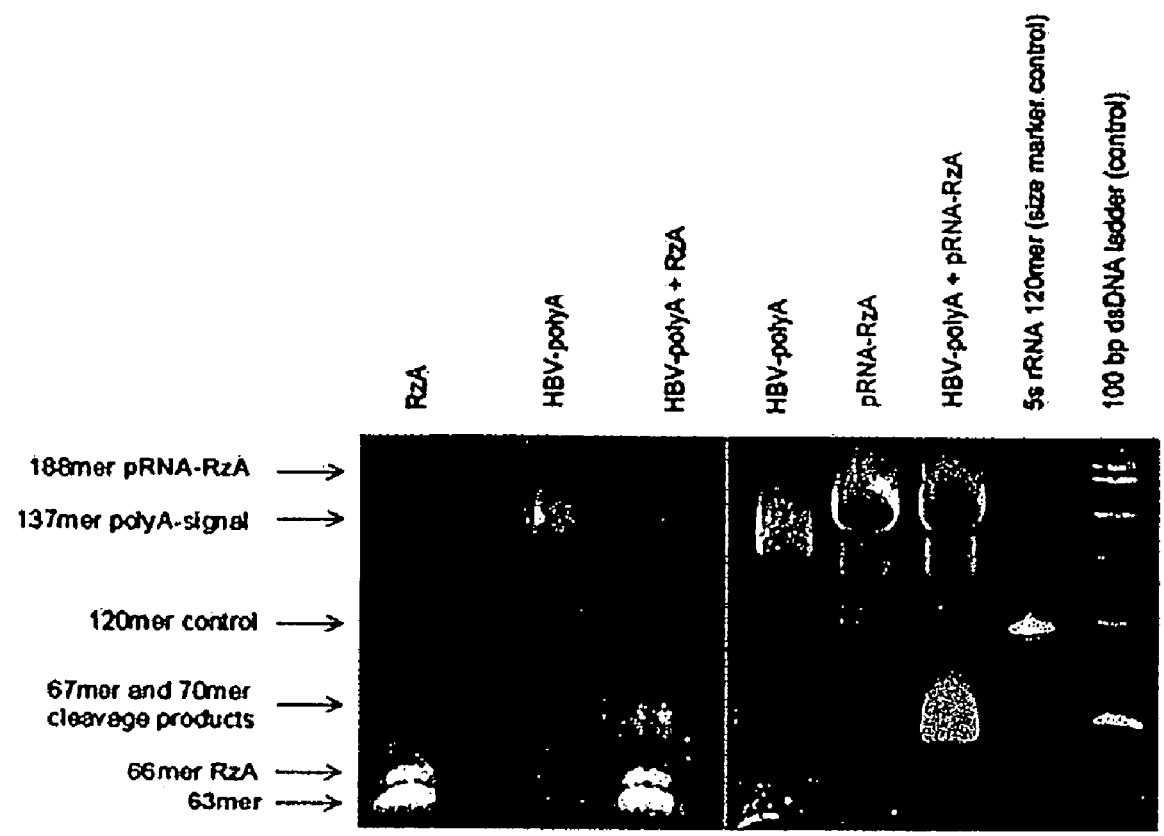
FIG. 14 depicts a denaturing urea gel evidencing successful cleavage of the substrate HBV-polyA into its expected 70mer and 67mer cleavage products.

Cleavage of HBV-polyA substrate by the functional chimera pRNA-RzA ribozyme is shown in FIG. 14. The ribozyme pRNA-RzA, which contains a pRNA moiety, was able to cleave the substrate HBV-polyA with nearly 100% efficiency. The predicted 67 base and 70 base cleavage products are seen as one band for the cleavage reaction that included both HBV-polyA and pRNA-RzA ribozyme. The lane labeled pRNA-RzA shows a control reaction that did not contain HBV-polyA, and the lane labeled HBV-polyA shows a control reaction that did not contain pRNA-RzA ribozyme.

The lane labeled RzA in FIG. 14 shows two bands. The upper band (66 nt) is the ribozyme that cleaves the HBV-polyA substrate. The lower band (63 nt) is a cis-cleaving ribozyme produced in the RzA ribozyme transcription reaction. The two ribozymes migrate closely on the gels. The lane labeled RzA-pRNA shows more than one band. The top band is the chimeric ribozyme pRNA-RzA. The lower band is the cleaved products as noted above. No un-cleaved substrate was seen.

In order to use equal molar concentrations of RzA and pRNA-RzA in cleavage reaction, a large mass of pRNA-RzA was used. The other materials shown between the chimeric ribozyme and the cleaved products are degraded chimera ribozyme due to the high RNA concentration in this gel and the large size of the chimeric ribozyme. Even a small percent of degradation resulted in visible degradation products. Due to the secondary structure and incomplete denaturation by urea, the migration rate of RNAs did not match perfectly with the size.

It was found that the hammerhead ribozyme including its two arms for HBV targeting was able to fold correctly while escorted by the pRNA. Comparison of the cleavage efficiency of the ribozyme with and without the pRNA vector revealed a significant difference. The ribozyme pRNA-RzA, which contains a pRNA moiety, was able to cleave the substrate HBV-polyA with nearly 100% efficiency. The chimeric ribozyme cleaved the polyA signal of HBV mRNA in vitro almost completely. However, the ribozyme RzA without the pRNA moiety cleaved the substrate with an efficiency much lower than 70% (not shown).

Example 5

Activity of pRNA-Ribozyme Chimera Against Hepatitis B Virus in Cell Culture

A plasmid pCRzA was obtained from Professor Guorong Qi in Shanghai. This plasmid contains sequences coding for a cis-acting hammerhead ribozyme flanked by two sequences targeting hepatitis B virus polyA signal. When this plasmid was co-transfected into HepG2 cells with the HBV genome, HBV RNA level was decreased, and hepatitis B virus replication was inhibited in a dose dependant fashion.

We constructed a plasmid pRNA-CRzA substantially in accordance with Example 3. In pRNA-CRzA, the hammerhead ribozyme and its flanking sequence were carried by the phi29 pRNA, generating a pRNA chimera.

The design of the pRNA-CRzA plasmid used for cell culture studies was basically the same as the one used for in vitro, except that the CMV promoter was used instead of the T7 promoter that was used for the in vitro studies (Table 1). Two versions of this ribozyme were tested: pRNA-RzA ribozyme, which contained a pRNA moiety, and RzA ribozyme, which did not. Both plasmids contain sequences coding for a hammerhead ribozyme targeting the HBV-polyA signal including the two cis-cleaving hammerhead ribozymes.

The tissue culture plasmid pRNA-CRzA encoding the chimera ribozyme was constructed by using XbaI and KpnI to remove the sequence encoding the unmodified ribozyme from the plasmid pCRzA that encoded the ribozyme targeting the HBV polyA signal (Feng et al., *Biol Chem* 382:655-60 (2001)). Then, a dsDNA fragment made by PCR that encoded the 188 nt chimeric ribozyme was ligated into the position of the plasmid pCRzA that had been double-digested with XbaI and KpnI (FIG. 15).

The HepG2 cells were maintained in Dulbecco's modified Eagle's medium (DMEM) supplemented with 10% fetal calf serum and antibiotics at 37° C. and 10% $CO_2$. Transient transfection was carried out with the method of calcium phosphate precipitation. In general, cells in 60-mm dishes were transient transfected with 1 μg of HBV expression plasmid p3.611 (Feng et al., *Biol Chem* 382:655-660 (2001)) and 5 μg of expression construct (CMV vector, pCRzA plasmid (Feng et al., *Biol Chem* 382:655-660 (2001)) or pRNA-RzA plasmid). 1 μg of pcDNA4LacZ carrying lacZ gene (Invitrogen) was also included in each transfection as internal control. β-galactosidase activity was detected to normalize the transfection efficiency among different dishes.

To analyze HBV viral RNA transcription, seventy-two hours after transfection, the cells were harvested and lysed in TRIZOL reagents (Gibcol-BRL) for total RNA extraction. For northern blot, 20 μg of denatured RNA was resolved in a 0.6M formaldehyde-1% agarose gel and transferred onto HYBOND N+ nylon membrane (Amersham). Probes were prepared by random priming with the 1.8 kb XbaI fragment of HBV (adr) from plasmid p3.6 II and [α-32P] dATP according to the supplier (Promega, Madison, Wis.). After hybridization with HBV probe, the blot was stripped and re-hybridized with a probe of GAPDH (glyceraldehyde-3-phosphate dehydrogenase) that served as an internal control for normalizing the level of total cell RNA.

To analyze e-antigen, seventy-two hours after transfection, cells were harvested and lysed in a buffer (1% NP-40, 50 mM Tris-HCl and 1 mM EDTA) at 37° C. for 10 minutes. Activity of β-galactosidase in cell lysate was determined to normalize the variation of transfection efficiency among different samples. The e-Ag in cell lysates and media was assayed with a commercial ELISA kit (Sino-American Co.) and normalized against β-galactosidase activity. The CMV vector, pCRzA, pRNA-RzA, and disabled ribozyme plasmid pCdRzA were transformed into HepG2 cells together with HBV expressing plasmid p3.6II and the β-galactosidae expressing plasmid pcDNA4LacZ serving as an internal control. See Table 2. The amount of CMV vector was arbitrarily taken as 1.

TABLE 2

Comparison of the e-antigen (e-Ag) level of HBV in medium and cytoplasm of HepG2 cells transfected with different plasmids.

| Plasmids | e-Ag in media | | e-Ag in cell lysate | | Number of experiments (n) |
|---|---|---|---|---|---|
| | $\overline{X}$ (Normalized) | S.D. | $\overline{X}$ (Normalized) | S.D. | |
| Vector | 1 | — | 1 | — | 3 |
| CrzA | 0.790 | 0.072 | 0.816 | 0.176 | 3 |
| pRNA-RzA | 0.503 | 0.055 | 0.563 | 0.153 | 3 |
| CdRzA | 0.830 | 0.052 | 0.760 | 0.052 | 3 |

The e-antigen assay was performed to investigate whether the pRNA could enhance the inhibition of HBV replication by hammerhead ribozyme. The e-Ag is expressed by translation from a start site upstream of the pre-core (pre-c) coding region, having a nearly identical amino acid sequence as the core antigen, while possessing different antigenicity due to the difference in location of protein expression. The e-Ag appears early during acute HBV infection and is suitable for antigen assay in cell culture.

Assay of e-Ag revealed that pRNA enhanced the inhibition effect of ribozyme by comparing the e-Ag level of cells transfected with plasmids pcRzA (expressing hammerhead ribozyme only), pRNA-RzA (expressing the chimeric ribozyme with pRNA vector), pCdRzA (expressing the disabled ribozyme), and vector only (Table 2). The inhibition by the catalytically inactive ribozyme may be due to an antisense mechanism that involves the hybridization of arm I and arm II to the complementary HBV sequences.

To evaluate the effect of pRNA-RzA ribozyme in cell cultures, ribozyme-expressing plasmids pCRzA, pRNA-RzA, pCdRzA or empty vector was co-transfected with HBV genome-expressing plasmid p3.6 II into hepatoma HepG2 cells. The p3.6II contains 1.2 copies of HBV (adr) genome and produces all viral RNA transcripts (3.5 Kb pre-core and pre-genomic RNA; 2.4 Kb Pre-S RNA, 2.1 kb S RNA and 0.8 Kb X RNA) in HepG2 cells without any additional factor. Total cellular RNA was extracted seventy-two hours post-transfection. After normalizing against β-galactosidase activity as an internal control, comparable amounts of RNA (the amount of RNA sample loaded in each lane can be evaluated by GAPDH level) were applied to gel and detected by Northern blotting with an HBV-specific DNA probe. The probe was used to detect the 3.5 Kb and 2.1/2.4 Kb viral RNA as indicated. The presence of pRNA-RzA ribozyme caused an obvious decrease in both 3.5 and 2.1/2.4 Kb HBV RNA level.

Figure 16:
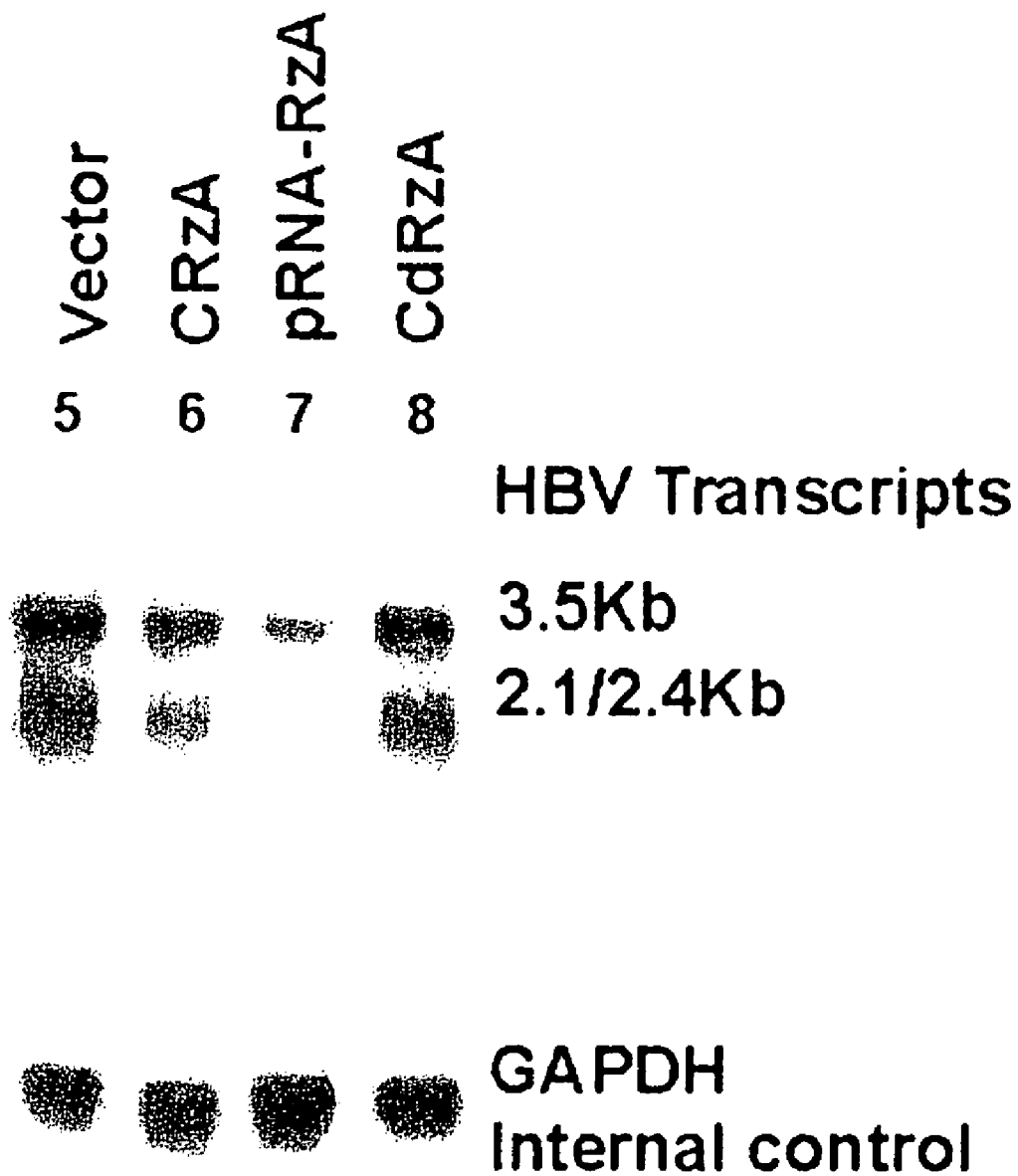
FIG. 16 depicts the effect of ribozymes on HBV RNA levels in HepG2 cells.

The inhibition by this modified ribozyme was more significant compared with the CRzA ribozyme especially in affecting 2.1/2.4 Kb viral RNA level. The disabled ribozyme CdRzA (encoded by plasmid pCdRzA) bearing one base mutation in Helix II was also used in parallel with CRzA ribozyme and pRNA-RzA ribozyme (FIG. 16).

Antigen assays and Northern blot have demonstrated that phi29 pRNA can chaperone and escort the hammerhead ribozyme to function in the cell, enhancing the cleavage efficiency and inhibition effect of the ribozyme on HBV. The mechanism for such increase in ribozyme activity is probably due to the fact that the pRNA can prevent the ribozyme from misfolding and protect the ribozyme from degradation by exonucleases present in cells. The pRNA molecule contains two independently functional domains: the procapsid binding domain and the DNA-translocation domain (FIG. 2(b)). It was demonstrated that exogenous RNA can be connected to the end of the pRNA without affecting pRNA folding. At least 120 nonspecific bases were extended from the 3' end of aptRNA without hindering the folding or function of the pRNA, indicating that the 117-base pRNA was folded independent of bases extended from its 3'-end. In addition, construction of biologically active circularly permuted pRNAs revealed that interruption of pRNA internal bases did not affect the global folding of the pRNA. The demonstration that the linking of the 3' and 5' ends of pRNA with variable lengths of nucleotide sequence, which did not affect the pRNA activity, is an indication that pRNA and the linking sequence fold independently.

These cell culture studies showed that the chimeric ribozyme was able to enhance the inhibition of HBV replication when compared with the ribozyme not escorted by pRNA, as demonstrated by Northern blot and e-antigen assays. pRNA could also carry another hammerhead ribozyme to cleave other RNA substrate. These studies show that a ribozyme could be placed between the 3' and 5' ends of the pRNA and will be able to fold without being influenced by the original pRNA sequence. These findings suggest that pRNA can be used as a vector for imparting stability to ribozymes, antisense, and other therapeutic RNA molecules in intracellular environments.

Example 6

Activity of pRNA-Ribozyme Chimera Against Cancer in Cell Culture

Growth and metastasis of solid tumors requires persistent angiogenesis. Angiogenesis is a important process by which new blood vessels are formed. The protein type 12 lipoxygenase (12-LOX) in platelets makes 12-HETE (12-hydroxy-5, 8,10,14-eicosatetraenoic acid) by adding $O_2$ to C-12 arachidonic acid. 12-LOX and its metabolites may be important factors in tumor angiogenesis. The application of this research could restrict tumor growth by preventing cancer cells from prompting blood vessels to grow in the surrounding tissue.

In vitro studies by Liu et al. have shown that this ribozyme, 12loxRz, efficiently cleaved the substrate (*Cancer Gene Ther.* 7:671-675 (2000)). Efficiency was increased when changing the reaction temperature from 37° C. to 50° C. Studies in cell culture showed that cells expressing the ribozyme from a plasmid had such a decreased level of 12-LOX mRNA that it was undetectable by Northern blotting. A control group of cells that only had a nonfunctional mutant ribozyme had only a slight decrease in the level of 12-LOX mRNA. This slight reduction in 12-LOX mRNA expression could have been the result of an antisense effect by the mutant ribozyme by merely binding to the 12-LOX mRNA without cleaving it. Cell extract was assayed for 12-LOX enzyme activity. Cells expressing ribozymes had 13% of 12-LOX enzyme activity after 6 months compared to parental cells. Cells expressing the mutant nonfunctional ribozyme had 80% of 12-LOX enzyme activity compared to parental cells (Liu et al., Cancer Gene Ther., 7:671-675, 2000). This demonstrates the activity of the ribozyme.

Figure 17:
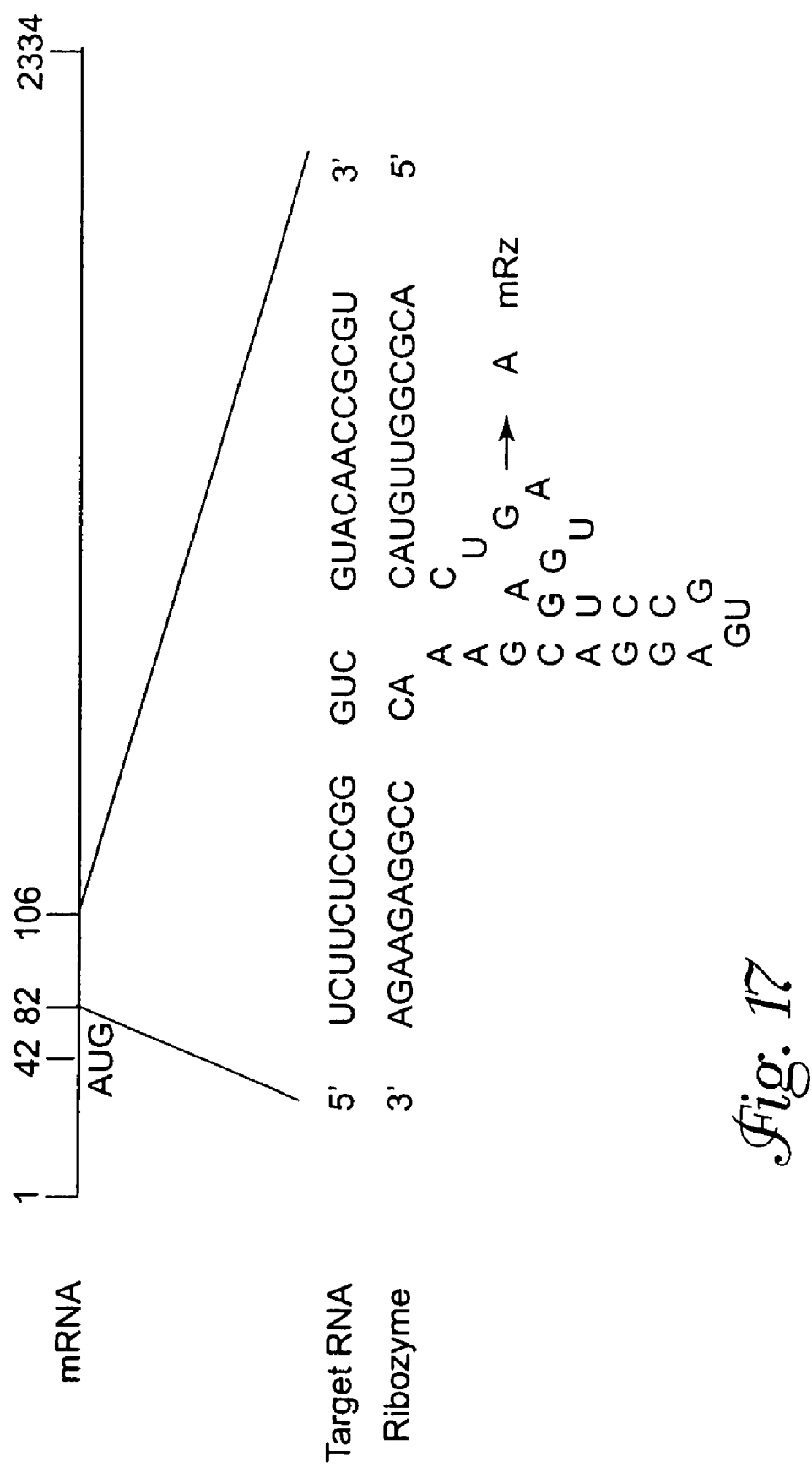
FIG. 17 depicts an anti-12-LOX ribozyme (SEQ ID NO:5) bound to substrate RNA (SEQ ID NO:6).

Platelet-type 12-lipoxygenase (12-lox) mRNA (FIG. 17) was selected as a target to test whether a chimera hammerhead ribozyme can function to suppress mRNA levels in human erythroleukemia (HEL) cells. We obtained the in vitro and tissue culture plasmids that encode the ribozyme from Professor Tien, Director of the National Key Lab of Virus Research in which the inventor Peixuan Guo is the Advisor and Visiting Professor. The hammerhead ribozyme was inserted into our pRNA essentially using the method described in Example 3. We created the chimerical ribozyme, 12loxRzpRNA, first constructing a dsDNA template in a two step PCR reaction from oligonucleotides encoding the T7 promoter and the 12loxRz inserted into the pRNA sequence. This template was subsequently transcribed to give the 12loxRzpRNA.

Experiments to test the activity of 12loxRzpRNA will be performed. For the in vitro experiments, the 12loxRz and a target RNA fragment of the 12-lox mRNA (the mRNA substrate) are produced from oligonucleotides essentially using the method described in Example 2. The 12loxRz and the substrate RNA are each transcribed from their own set of two hybridized DNA oligonucleotides. One encodes the negative sense T7 polymerase promoter and the substrate sequence or the 12loxRz sequence. The other oligonucleotide encodes the positive sense T7 promoter sequence. The RNA substrate is radio-labeled using calf intestine phosphatase (CIP) and then polynucleotide kinase (PNK) with $[\gamma^{32}P]$-ATP.

The cleavage efficiency of two ribozymes with and without the pRNA moiety will be evaluated both in vitro and cells (cell culture). For the in vitro study, we will compare the stability of the ribozymes resistance to pH, ion concentration, RNase and cell lysate. These are factors that affect the ribozyme stability and function in the cell.

HEL cells expressing 12-lox will be used for the cell culture experiments. An empty expression cassette or the 12loxRzpRNA in an expression cassette encoding the tRNA$^{val}$ promoter, the 12loxRzpRNA chimera, and the eukaryote polymerase III terminator sequence (5 T residues) will be delivered by transfection using electroporation. Expression of the 12loxRzpRNA chimera and 12-lox mRNA in the cells will be detected by northern blot. Nontransfected HEL cells will be used as a control. 12-LOX enzyme activity will be evaluated by the determination of whether there is a reduction in 12-HETE production in HEL cells.

For both the in vitro and cell culture experiments, a mutant 12loxRz and a mutant 12loxRzpRNA chimera control will be used as a second control. The mutant 12loxRz has one of its nucleotides in its conserved catalytic core domain substituted with another base, rendering the ribozyme unable to cleave the substrate RNA. The use of the non-catalytic mutant ribozymes as a second control is designed to reveal whether the native ribozyme is capable of inhibiting translation by binding to the RNA substrate (i.e., an antisense effect), as opposed to cleaving it.

SEQUENCE LISTING FREE TEXT 1 organism name: Bacteriophage phi29/PZA 2 circularly permuted pRNA from bacteriophage phi29 (short loop)

3 RNA chimera containing phi29 pRNA and hammerhead ribozyme

4 U7snRNA substrate 5 anti-12-Lox ribozyme

6 Lox substrate RNA 7 pRNA chimera 8 linking loop

9 U7 substrate

10 RzU7 hammerhead ribozyme 11, 33 circularly permuted Bacteriophage SF5' pRLNA chimera 12, 34 circularly permuted Bacteriophage B103 RNA chimera 13, 35 circularly permuted bacteriophage phi29 pRNA chimera 14, 36 circularly permuted Bacteriophage M2 nRNA chimera 15, 37 circularly permuted Bacteriophage GA1 pRNA chimera 16, 38 aptRNA 17 RNA chimera containing phi29 pRNA and hammerhead ribozyme 18 RzA hammerhead ribozyme 19-22 3' pRNA extension 23 hammerhead ribozyme 24 Hepatitis B virus polyA substrate 25 RNA chimera containing phi29 pRNA and hammerhead ribozyme 26 Wild-type pRNA with base pair change at base of stem structure.

The complete disclosures of all patents, patent applications including provisional patent applications, and publications, and electronically available material (e.g., GenBank amino acid and nucleotide sequence submissions) cited herein are incorporated by reference. The foregoing detailed description and examples have been provided for clarity of understanding only. No unnecessary limitations are to be understood therefrom. The invention is not limited to the exact details shown and described; many variations will be apparent to one skilled in the art and are intended to be included within the invention defined by the claims.

What is claimed is:

1. A pRNA chimera comprising:
   (a) a pRNA region; and
   (b) a spacer region comprising a biologically active RNA, the spacer region covalently linked at its 5' and 3' ends to the pRNA region, wherein the biologically active RNA specifically binds a pre-identified substrate;
   wherein the pRNA region comprises:
      (i) in the 5' to 3' direction beginning at the covalent linkage of the pRNA with the 3' end of the spacer region
         a first loop;
         a second loop; and
         a lower stem-loop structure comprising a bulge, a first stem section and a third loop;
      (ii) a second stem section interposed between the spacer region and the stem-loop structure;
      (iii) a third stem section interposed between the stem-loop structure and the first loop;
      (iv) a fourth stem section interposed between the first loop and the second loop; and further comprises
      (v) an opening defining 5' and 3' ends of the pRNA chimera.

2. The pRNA chimera of claim 1 wherein the biologically active RNA is selected from the group consisting of a ribozyme, a siRNA, an RNA aptamer, an antisense RNA and a peptide nucleic acid (PNA).

3. The pRNA chimera of claim 1 wherein
   the pRNA region comprises a circularly permuted pRNA of a bacteriophage selected from the group consisting of bacteriophage φ29, SF5', B103, PZA, M2, NF and GA1.

4. The pRNA chimera of claim 3 wherein the biologically active RNA is selected from the group consisting of a ribozyme, a siRNA, an RNA aptamer, an antisense RNA and a peptide nucleic acid (PNA).

5. A DNA molecule comprising a nucleotide sequence that encodes the pRNA chimera of claim 1.

6. A method for making a pRNA chimera comprising:
   providing a DNA encoding the pRNA chimera of claim 1; and
   transcribing the DNA in vitro to yield the pRNA chimera.

7. The method of claim 6 wherein the step of providing comprises generating the DNA by a polymerase chain reaction.

8. The method of claim 6 wherein the step of providing comprises (i) cloning the DNA into a plasmid; and (ii) replicating the plasmid.

9. A method for delivering a biologically active RNA to a cell comprising:
   introducing into the cell a DNA molecule comprising a nucleotide sequence that operably encodes the pRNA chimera of claim 1; and
   causing transcription of the DNA to yield the biologically active RNA.

10. The method of claim 9 wherein the biologically active RNA is selected from the group consisting of a ribozyme, a siRNA, an RNA aptamer, an antisense RNA and a peptide nucleic acid (PNA).

11. The method of claim 9 wherein the cell is present in a cell culture, a tissue, an organ or an organism.

12. The method of claim 9 wherein the cell is a mammalian cell.

13. The method of claim 12 wherein the cell is a human cell.

14. A pRNA chimera comprising:
   (a) a pRNA region; and
   (b) a spacer region comprising a biologically active RNA that specifically binds a pre-identified ligand or receptor, the spacer region covalently linked at its 5' and 3' ends to the pRNA region; wherein the pRNA region comprises:
      (i) in the 5' and 3' direction beginning at the covalent linkage of the pRNA with the 3' end of the spacer region
         a first loop;
         a second loop; and
         a lower stem-loop structure comprising a bulge, a first stem section and a third loop;
      (ii) a second stem section interposed between the spacer region and the stem-loop structure;
      (iii) a third stem section interposed between the stem-loop structure and the first loop;
      (iv) a fourth stem section interposed between the first loop and the second loop; and further comprises
      (v) an opening defining 5' and 3' ends of the pRNA chimera.

15. A pRNA chimera comprising:
   (a) a pRNA region; and
   (b) a spacer region comprising a biologically active RNA that comprises at least one of a specific binding activity and an enzymatic activity, the spacer region covalently linked at its 5' and 3' ends to the pRNA region;
   wherein the pRNA region comprises:
      (i) in the 5' and 3' direction beginning at the covalent linkage of the pRNA with the 3' end of the spacer region
         a first loop;
         a second loop; and
         a lower stem-loop structure comprising a bulge, a first stem section and a third loop;
      (ii) a second stem section interposed between the spacer region and the stem-loop structure;
      (iii) a third stem section interposed between the stem-loop structure and the first loop;
      (iv) a fourth stem section interposed between the first loop and the second loop; and further comprises
      (v) an opening defining 5' and 3' ends of the pRNA chimera.

16. The pRNA chimera of claim 1 wherein (i) the biologically active RNA comprises an aptamer and (ii) the pre-identified substrate comprises a cell surface receptor.

17. A pRNA chimera comprising:
   (a) a pRNA region; and
   (b) a spacer region comprising a biologically active RNA that does not comprise the nucleotide sequence UAAUACGACUCACUAUA as set forth in SEQ ID NO:8, the spacer region covalently linked at its 5' and 3' ends to the pRNA region, wherein the biologically active RNA specifically binds a pre-identified substrate;
   wherein the pRNA region comprises:
      (i) in the 5' to 3' direction beginning at the covalent linkage of the pRNA with the 3' end of the spacer region
         a first loop;
         a second loop; and
         a lower stem-loop structure comprising a bulge, a first stem section and a third loop;
      (ii) a second stem section interposed between the spacer region and the stem-loop structure;
      (iii) a third stem section interposed between the stem-loop structure and the first loop;

(iv) a fourth stem section interposed between the first loop and the second loop; and further comprises (v) an opening defining 5' and 3' ends of the pRNA chimera.

18. A pRNA chimera comprising:
(a) a pRNA region; and
(b) a spacer region comprising a biologically active RNA, the spacer region covalently linked at its 5' and 3' ends to the pRNA region, wherein the biologically active RNA binds a pre-identified substrate and comprises a polyribonucleotide selected from the group consisting of an RNA of at least 25-100, 46, 47, 63, 66, 94, 120, 168 and 188 nucleotides,
wherein the pRNA region comprises:
(i) in the 5' to 3' direction beginning at the covalent linkage of the pRNA with the 3' end of the spacer region a first loop;

a second loop; and a lower stem-loop structure comprising a bulge, a first stem section and a third loop;

(ii) a second stem section interposed between the spacer region and the stem-loop structure;

(iii) a third stem section interposed between the stem-loop structure and the first loop;

(iv) a fourth stem section interposed between the first loop and the second loop; and further comprises (v) an opening defining 5' and 3' ends of the pRNA chimera.

* * * * *

UNITED STATES PATENT AND TRADEMARK OFFICE
CERTIFICATE OF CORRECTION

PATENT NO. : 7,655,787 B2  Page 1 of 1
APPLICATION NO. : 10/373612
DATED : February 2, 2010
INVENTOR(S) : Peixuan Guo et al.

It is certified that error appears in the above-identified patent and that said Letters Patent is hereby corrected as shown below:

Item 56
"Guo, Peixuan, "Stoichiometry Quantification – Complex Biological System," Grant Abstract, Grant No. 5RO165060529-02 [online]. National Institute of Health – National Institute of General Medical Sciences, project dates May 1, 2000 to Apr. 30, 2003 [retrieved on Jul. 2, 2007]. Retrieved from the Internet: URL:http://crisp.cit.nih.gov/crisp/CRISP_LIB.getdoc?textkey=6387064&p_grant num=5R0lGM06 0529-02&p_query=&ticket=40535116&p_audit session_id-249250764&p_keywords=; 2 pgs" should read, --Guo, Peixuan, "Stoichometry Quantification – Complex Biological System," Grant Abstract, Grant No. 5RO1GM060529-02 [online]. National Institute of Health – National Institute of General Medical Sciences, project dates May 1, 2000 to Apr. 30, 2003 [retrieved on Jul. 2, 2007]. Retrieved from the Internet: URL: http://crisp.cit.nih.giv/crisp/CRISP_LIB.getdoc?textkey=6387064&p_grant_num=5R01GM060529-02&p_query=&ticket=40535116&p_audit_session_id=249250764&p_keywords=; 2pgs--.

Item 56
"Guo, Peixuan, "Structure/Fucntion of phi29 hexameric pRNA," Grant Abstract, Grant No. IRO1GM059944-01" should read, --Guo, Peixuan, "Structure/Function of phi29 hexameric pRNA," Grant Abstract, Grant No. 1RO1GM059944-01--.

Item 56
"Guo, Peixuan "Struture/Function of phi29 hexameric pRna," Grant Abstract, Grant No. 5R01GM059944-04 [online]. National Institute of Health – National Institute of General Medical Sciences, project dates Aug. 31, 1999 to Aug. 31, 2005" should read, --Guo, Peixuan "Structure/Function of phi29 hexameric pRna," Grant Abstract, Grant No. 5R01GM059944-04 [online]. National Institute of Health – National Institute of General Medical Sciences, project dates Aug. 1, 1999 to Aug. 31, 2005--.

Signed and Sealed this

Nineteenth Day of October, 2010

David J. Kappos
*Director of the United States Patent and Trademark Office*

UNITED STATES PATENT AND TRADEMARK OFFICE
CERTIFICATE OF CORRECTION

PATENT NO.      : 7,655,787 B2                                    Page 1 of 1
APPLICATION NO. : 10/373612
DATED           : February 2, 2010
INVENTOR(S)     : Guo et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 864 days.

Signed and Sealed this

Twenty-third Day of November, 2010

David J. Kappos
*Director of the United States Patent and Trademark Office*

SEQUENCE LISTING

<160> NUMBER OF SEQ ID NOS: 38

<210> SEQ ID NO 1
<211> LENGTH: 120

```
<212> TYPE: RNA
<213> ORGANISM: Bacteriophage phi29/PZA

<400> SEQUENCE: 1
ucaaugguac gguacuucca uugucaugug uauguugggg auuaaacccu gauugaguuc      60
agcccacaua cuuuguugau ugguugucaa ucauggcaaa agugcacgcu acuuugauaa     120

<210> SEQ ID NO 2
<211> LENGTH: 121
<212> TYPE: RNA
<213> ORGANISM: Artificial Sequence
<220> FEATURE:
<223> OTHER INFORMATION: Description of Artificial Sequence: Synthetic
      cpRNA (small loop) oligonucleotide

<400> SEQUENCE: 2
ggaaugguac gguacuucca uugucaugug uauguugggg auuaaacccu gauugaguuc      60
agcccacaua cuuuguugau ugguugucaa ucauggcaaa agugcacgcu acuuccuaa      120 a                                                                    121

<210> SEQ ID NO 3
<211> LENGTH: 167
<212> TYPE: RNA
<213> ORGANISM: Artificial Sequence
<220> FEATURE:
<223> OTHER INFORMATION: Description of Artificial Sequence: Synthetic
      pRNA chimera oligonucleotide

<400> SEQUENCE: 3
guugauuggu ugucaaucau ggcaaaagug cacgcuacuu ugaaaaacaa auucuaaaac      60
ugaugagucc gugaggacga aagcuguaac acaaaaucaa uggacggua cuuccauugu     120 caugugaug uugggauua aacccugauu gaguucagcc cacauac                   167

<210> SEQ ID NO 4
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide portion of U7 snRNA substrate

<400> SEQUENCE: 4
guguuacagc ucuuuuagaa uuug                                            24

<210> SEQ ID NO 5
<211> LENGTH: 46
<212> TYPE: RNA
<213> ORGANISM: Artificial Sequence
<220> FEATURE:
<223> OTHER INFORMATION: Description of Artificial Sequence: Synthetic
      anti-12-LOX-ribozyme oligonucleotide

<400> SEQUENCE: 5
acgcgguugu accugaugag uccgugagga cgaaacccgg agaaga                    46

<210> SEQ ID NO 6
<211> LENGTH: 25
<212> TYPE: RNA
<213> ORGANISM: Artificial Sequence
<220> FEATURE:
<223> OTHER INFORMATION: Description of Artificial Sequence: Synthetic
      substrate RNA oligonucleotide

<400> SEQUENCE: 6
```
ucuucuccgg gucguacaac cgcgu                                              25

<210> SEQ ID NO 7
<211> LENGTH: 28
<212> TYPE: RNA
<213> ORGANISM: Artificial Sequence
<220> FEATURE:
<223> OTHER INFORMATION: Description of Artificial Sequence: Synthetic
      pRNA chimera oligonucleotide
<220> FEATURE:
<221> NAME/KEY: modified_base
<222> LOCATION: (7)..(14)
<223> OTHER INFORMATION: any nucleotide base; this region may encompass
      4-8 nucleotides

<400> SEQUENCE: 7
guugaunnnn nnnngucaau cauggcaa                                           28

<210> SEQ ID NO 8
<211> LENGTH: 17
<212> TYPE: RNA
<213> ORGANISM: Artificial Sequence
<220> FEATURE:
<223> OTHER INFORMATION: Description of Artificial Sequence: Synthetic
      linking loop oligonucleotide

<400> SEQUENCE: 8
uaauacgacu cacuaua                                                       17

<210> SEQ ID NO 9
<211> LENGTH: 94
<212> TYPE: RNA
<213> ORGANISM: Artificial Sequence
<220> FEATURE:
<223> OTHER INFORMATION: Description of Artificial Sequence: Synthetic
      U7 template sequence

<400> SEQUENCE: 9
gggaaagcuu auaguguuac agcucuuuua gaauuugucu agcagguuuu cugacuucgg        60
ucggaaaacg ccuaacguug caugccugca gguc                                    94

<210> SEQ ID NO 10
<211> LENGTH: 47
<212> TYPE: RNA
<213> ORGANISM: Artificial Sequence
<220> FEATURE:
<223> OTHER INFORMATION: Description of Artificial Sequence: Synthetic
      RzU7 oligonucleotide

<400> SEQUENCE: 10
ggcaaauucu aaaacugaug aguccgugag gacgaaagcu guaacac                      47

<210> SEQ ID NO 11
<211> LENGTH: 44
<212> TYPE: RNA
<213> ORGANISM: Artificial Sequence
<220> FEATURE:
<223> OTHER INFORMATION: Description of Artificial Sequence: Synthetic
      circularly permuted SF5' pRNA chimera oligonucleotide

<400> SEQUENCE: 11
gggagcguaa aacacucuug cauuaaaaau augacugauu ucgc                         44

<210> SEQ ID NO 12
<211> LENGTH: 43
<212> TYPE: RNA

<213> ORGANISM: Artificial Sequence
<220> FEATURE:
<223> OTHER INFORMATION: Description of Artificial Sequence: Synthetic
     circularly permuted B103 pRNA oligonucleotide

<400> SEQUENCE: 12
ggggauugau agcccucuua cuaaaaguga uuguuucuuu guc                43

<210> SEQ ID NO 13
<211> LENGTH: 43
<212> TYPE: RNA
<213> ORGANISM: Artificial Sequence
<220> FEATURE:
<223> OTHER INFORMATION: Description of Artificial Sequence: Synthetic
     circularly permuted phi29/PZA pRNA chimera oligonucleotide

<400> SEQUENCE: 13
guugauuggu ugucaaucau ggcaaaagug cacgcuacuu uga                43

<210> SEQ ID NO 14
<211> LENGTH: 43
<212> TYPE: RNA
<213> ORGANISM: Artificial Sequence
<220> FEATURE:
<223> OTHER INFORMATION: Description of Artificial Sequence: Synthetic
     circularly permuted M2/NF pRNA chimera oligonucleotide

<400> SEQUENCE: 14
ggggauugau aacccucuua cuaaaaguga uuguuucuuu guc                43

<210> SEQ ID NO 15
<211> LENGTH: 42
<212> TYPE: RNA
<213> ORGANISM: Artificial Sequence
<220> FEATURE:
<223> OTHER INFORMATION: Description of Artificial Sequence: Synthetic
     circularly permuted GA1 pRNA chimera oligonucleotide

<400> SEQUENCE: 15
uguugcgugg uagcaauacu auauauacuc ucucucguuu ua                 42

<210> SEQ ID NO 16
<211> LENGTH: 43
<212> TYPE: RNA
<213> ORGANISM: Artificial Sequence
<220> FEATURE:
<223> OTHER INFORMATION: Description of Artificial Sequence: Synthetic
     circularly permuted aptamer pRNA oligonucleotide

<400> SEQUENCE: 16
guugauuggu ugucaaucau ggcaaaagug cacgcuacuu ucc                43

<210> SEQ ID NO 17
<211> LENGTH: 188
<212> TYPE: RNA
<213> ORGANISM: Artificial Sequence
<220> FEATURE:
<223> OTHER INFORMATION: Description of Artificial Sequence: Synthetic
     cis-cleaved pRNA-PZA oligonucleotide

<400> SEQUENCE: 17
gcuaguucua gaguugauug guugucaauc auggcaaaag ugcacgcuac uuugcaaaac     60
aaauucuuua cugaugaguc cgugaggacg aaacggguca aaagcaaugg uacgguacuu   120
ccauugucau uguaguguug gggauuaaac ccugauugag uucagcccac auacgguacc   180
ucgacguc                                                            188

<210> SEQ ID NO 18
<211> LENGTH: 66
<212> TYPE: RNA
<213> ORGANISM: Artificial Sequence
<220> FEATURE:
<223> OTHER INFORMATION: Description of Artificial Sequence: Synthetic
      RZA oligonucleotide

<400> SEQUENCE: 18
gcuaguucua gacaaauucu uuacugauga guccgugagg acgaaacggg ucgguaccuc        60
gacguc                                                                  66

<210> SEQ ID NO 19
<211> LENGTH: 10
<212> TYPE: RNA
<213> ORGANISM: Artificial Sequence
<220> FEATURE:
<223> OTHER INFORMATION: Description of Artificial Sequence: Synthetic
      3' overhang oligonucleotide

<400> SEQUENCE: 19
aagccgaauu                                                              10

<210> SEQ ID NO 20
<211> LENGTH: 59
<212> TYPE: RNA
<213> ORGANISM: Artificial Sequence
<220> FEATURE:
<223> OTHER INFORMATION: Description of Artificial Sequence: Synthetic
      3' overhang oligonucleotide

<400> SEQUENCE: 20
aagccgaauu ccagcacacu ggcggccguu acuaguggau ccgagcucgg uaccaagcu         59

<210> SEQ ID NO 21
<211> LENGTH: 54
<212> TYPE: RNA
<213> ORGANISM: Artificial Sequence
<220> FEATURE:
<223> OTHER INFORMATION: Description of Artificial Sequence: Synthetic
      3' overhang oligonucleotide

<400> SEQUENCE: 21
ccuuuuacau gcgacacaga cgaagcgcua aaacguggga uucugucg uuuu                54

<210> SEQ ID NO 22
<211> LENGTH: 120
<212> TYPE: RNA
<213> ORGANISM: Artificial Sequence
<220> FEATURE:
<223> OTHER INFORMATION: Description of Artificial Sequence: Synthetic
      3' overhang oligonucleotide

<400> SEQUENCE: 22
ucaaugguac gguacuucca uugucaugug uauguugggg auuaaacccu gauugaguuc        60
agcccacaua cuuuguugau ugguugucaa ucauggcaaa agugcacgcu acuuugauaa       120

<210> SEQ ID NO 23
<211> LENGTH: 40
<212> TYPE: RNA
<213> ORGANISM: Artificial Sequence
<220> FEATURE:
<223> OTHER INFORMATION: Description of Artificial Sequence: Synthetic
      hammerhead ribozyme oligonucleotide

<400> SEQUENCE: 23
caaauucuuu acugaugagu ccgugaggac gaaacggguc                                40

<210> SEQ ID NO 24
<211> LENGTH: 19
<212> TYPE: RNA
<213> ORGANISM: Artificial Sequence
<220> FEATURE:
<223> OTHER INFORMATION: Description of Artificial Sequence: Synthetic
      HBV polyA target oligonucleotide

<400> SEQUENCE: 24
gacccguaua aagaauuug                                                       19

<210> SEQ ID NO 25
<211> LENGTH: 162
<212> TYPE: RNA
<213> ORGANISM: Artificial Sequence
<220> FEATURE:
<223> OTHER INFORMATION: Description of Artificial Sequence: Synthetic
      ribozyme pRNA-RZA

<400> SEQUENCE: 25
guugauuggu ugucaaucau ggcaaaagug cacgcuacuu ugaaaacaa auucuuuacu          60 gaugaguccg ugaggacgaa acggguaaaa aucaauggua cgguacuucc auugucaugu        120
guauguuggg gauuaaaccc ugauugaguu cagcccacau ac                           162

<210> SEQ ID NO 26
<211> LENGTH: 119
<212> TYPE: RNA
<213> ORGANISM: Artificial Sequence
<220> FEATURE:
<223> OTHER INFORMATION: Description of Artificial Sequence: Synthetic
      pRNA dimer oligonucleotide

<400> SEQUENCE: 26
gcaaugguac gguacuucca uugucaugug uauguugggg auuaacgccu gauugaguuc          60
agcccacaua cuuuguugau uguccgucaa ucauggcaaa agugccgcua cuuugcuaa         119

<210> SEQ ID NO 27
<211> LENGTH: 117
<212> TYPE: RNA
<213> ORGANISM: Artificial Sequence
<220> FEATURE:
<223> OTHER INFORMATION: Description of Artificial Sequence: Synthetic
      pRNA oligonucleotide

<400> SEQUENCE: 27
ucaaugguac gguacuucca uugucaugug uauguugggg auuaaacccu gauugaguuc          60
agcccacaua cuuuguugau ugguugucaa ucauggcaaa agugcacgcu acuuga            117

<210> SEQ ID NO 28
<211> LENGTH: 114
<212> TYPE: RNA
<213> ORGANISM: Artificial Sequence
<220> FEATURE:
<223> OTHER INFORMATION: Description of Artificial Sequence: Synthetic
      circularly permuted pRNA oligonucleotide

<400> SEQUENCE: 28
gcaaugguac gguacuucca uugucaugug uauguugggg auuaaacccu gauugaguuc          60
agcccacaua cguugauugg uugucaauca uggcaaaagu gcacgcuacu uugc              114

<210> SEQ ID NO 29
<211> LENGTH: 135
<212> TYPE: RNA
<213> ORGANISM: Artificial Sequence
<220> FEATURE:
<223> OTHER INFORMATION: Description of Artificial Sequence: Synthetic
      circularly permuted pRNA oligonucleotide

<400> SEQUENCE: 29
ggaaugguac gguacuucca uugucaugug uauguugggg auuaaacccu gauugaguuc      60
agcccacaua cuuuguugau ugguugucaa ucauggcaaa agugcacgcu acuuuccuua     120
auacgacuca cuaua                                                      135

<210> SEQ ID NO 30
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
ttcctaaagg aatgg                                                       15

<210> SEQ ID NO 31
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
ttccttaata cgactcacta taggaatgg                                        29

<210> SEQ ID NO 32
<211> LENGTH: 55
<212> TYPE: RNA
<213> ORGANISM: Artificial Sequence
<220> FEATURE:
<223> OTHER INFORMATION: Description of Artificial Sequence: Synthetic
      circularly permuted SF5' pRNA chimera oligonucleotide
<220> FEATURE:
<221> NAME/KEY: modified_base
<222> LOCATION: (25)..(32)
<223> OTHER INFORMATION: any nucleotide base; this region may encompass
      4-8 nucleotides

<400> SEQUENCE: 32
uugucaugug uauguugggg auuannnnnn nncugauuga guucagccca cauac            55

<210> SEQ ID NO 33
<211> LENGTH: 68
<212> TYPE: RNA
<213> ORGANISM: Artificial Sequence
<220> FEATURE:
<223> OTHER INFORMATION: Description of Artificial Sequence: Synthetic
      circularly permuted SF5' pRNA chimera oligonucleotide

<400> SEQUENCE: 33
gugagacauc guauuuacua uaauguaugu gugucggguu guuucggau ugaguccgc         60 cgacagca                                                               68

<210> SEQ ID NO 34
<211> LENGTH: 72

```
<212> TYPE: RNA
<213> ORGANISM: Artificial Sequence
<220> FEATURE:
<223> OTHER INFORMATION: Description of Artificial Sequence: Synthetic
      circularly permuted B103 pRNA oligonucleotide

<400> SEQUENCE: 34
gacaaggugc aacacuuccu auaguauggu gcgugauugg gguauauccu gauugaguuc      60
agcccacacg cc                                                         72

<210> SEQ ID NO 35
<211> LENGTH: 71
<212> TYPE: RNA
<213> ORGANISM: Artificial Sequence
<220> FEATURE:
<223> OTHER INFORMATION: Description of Artificial Sequence: Synthetic
      circularly permuted phi29/PZA pRNA chimera oligonucleotide

<400> SEQUENCE: 35 ucaauggoac gguacuucca uugucaugug uauguugggg auuaaacccu gauugaguuc      60
agcccacaua c                                                          71

<210> SEQ ID NO 36
<211> LENGTH: 72
<212> TYPE: RNA
<213> ORGANISM: Artificial Sequence
<220> FEATURE:
<223> OTHER INFORMATION: Description of Artificial Sequence: Synthetic
      circularly permuted M2/NF pRNA chimera oligonucleotide

<400> SEQUENCE: 36
gacaaggugc aacacuuccu auaguauggc acaugauugg gguauauccu gauugaguuc      60
agcccacaug uc                                                         72

<210> SEQ ID NO 37
<211> LENGTH: 68
<212> TYPE: RNA
<213> ORGANISM: Artificial Sequence
<220> FEATURE:
<223> OTHER INFORMATION: Description of Artificial Sequence: Synthetic
      circularly permuted GA1 pRNA chimera oligonucleotide

<400> SEQUENCE: 37
uaaggcauug agguuaaaau auauaggcug ugcaacgggc auccuacugu aaaaaguacc      60
guugacag                                                              68

<210> SEQ ID NO 38
<211> LENGTH: 75
<212> TYPE: RNA
<213> ORGANISM: Artificial Sequence
<220> FEATURE:
<223> OTHER INFORMATION: Description of Artificial Sequence: Synthetic
      circularly permuted aptamer pRNA oligonucleotide

<400> SEQUENCE: 38 ggaauggoac gguacuucca uugucaugug uagggouggg aagaaacugu ggcacuucgg      60
ugccagcaac ccuac                                                      75
```